US012584168B2

(12) United States Patent
Clarke et al.

(10) Patent No.: US 12,584,168 B2
(45) **Date of Patent: *Mar. 24, 2026**

(54) SAMPLE PREPARATION METHOD

(71) Applicant: Oxford Nanopore Technologies PLC, Oxford (GB)

(72) Inventors: James Anthony Clarke, Oxford (GB); Marion Louise Crawford, Oxford (GB); James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 794 days.

This patent is subject to a terminal disclaimer.

(21) Appl. No.: 18/054,514

(22) Filed: Nov. 10, 2022

(65) Prior Publication Data

US 2023/0250474 A1 Aug. 10, 2023

Related U.S. Application Data

(63) Continuation of application No. 15/120,186, filed as application No. PCT/GB2015/050483 on Feb. 19, 2015, now Pat. No. 10,669,578.

(30) Foreign Application Priority Data

Feb. 21, 2014 (GB) ..................................... 1403096

(51) Int. Cl.
*C12Q 1/6869* (2018.01)

(52) U.S. Cl.
CPC .................................. *C12Q 1/6869* (2013.01)

(58) Field of Classification Search
CPC ............ C12Q 1/6869; C12Q 2525/117; C12Q 2565/518; C12Q 2565/631
See application file for complete search history.

(56) References Cited

U.S. PATENT DOCUMENTS 5,215,899 A 6/1993 Dattagupta
5,424,413 A 6/1995 Hogan et al.
5,561,043 A 10/1996 Cantor et al.
5,714,320 A 2/1998 Kool
5,777,078 A 7/1998 Bayley et al.
5,795,782 A 8/1998 Church et al.
5,817,771 A 10/1998 Bayley et al.
5,866,328 A 2/1999 Bensimon et al.
5,866,336 A 2/1999 Nazarenko et al.
5,985,834 A 11/1999 Engel et al.
6,015,714 A 1/2000 Baldarelli et al.
6,087,099 A 7/2000 Gupte et al.
6,123,819 A 9/2000 Peeters
6,127,166 A 10/2000 Bayley et al.
6,251,610 B1 6/2001 Gupte et al.
6,274,320 B1 8/2001 Rothberg et al.
6,362,002 B1 3/2002 Denison et al.
6,403,319 B1 6/2002 Lizardi et al.
6,426,231 B1 7/2002 Bayley et al.
6,451,563 B1 9/2002 Wittig et al.
6,451,593 B1 9/2002 Wittig et al.
6,465,193 B2 10/2002 Akeson et al.
6,498,023 B1 12/2002 Abarzua
6,627,067 B1 9/2003 Branton et al.
6,709,861 B2 3/2004 Mead et al.
6,787,308 B2 9/2004 Balasubramanian et al.
6,824,659 B2 11/2004 Bayley et al.
6,863,833 B1 3/2005 Bloom et al.
6,916,665 B2 7/2005 Bayley et al.
6,927,070 B1 8/2005 Bayley et al.
7,087,729 B1 8/2006 Prive
7,189,503 B2 3/2007 Akeson et al.
7,238,485 B2 7/2007 Akeson et al.
7,361,466 B2 4/2008 Korlach et al.
7,507,575 B2 3/2009 Bedingham et al.
7,700,281 B2 4/2010 Kubu et al.
7,745,116 B2 6/2010 Williams
8,105,846 B2 1/2012 Bayley et al.
8,143,030 B2 3/2012 Maxham et al.
8,153,375 B2 4/2012 Travers et al.
8,343,746 B2 1/2013 Rank et al.
8,383,369 B2 2/2013 Maxham et al.
8,628,940 B2 1/2014 Sorenson et al.
8,652,779 B2 2/2014 Turner et al.
8,785,211 B2 7/2014 Bayley et al.
8,822,160 B2 9/2014 Bayley et al.
8,889,348 B2 11/2014 Ju
9,057,102 B2 6/2015 Turner et al.
(Continued)

FOREIGN PATENT DOCUMENTS

CN 101495656 A 7/2009
CN 102245760 A 11/2011
(Continued)

OTHER PUBLICATIONS

International Preliminary Report on Patentability for Application PCT/GB2015/050483 mailed Aug. 23, 2016.
International Search Report and Written Opinion for Application PCT/GB2015/050483 mailed Jun. 8, 2015.
[No Author Listed], Multiplex sequencing. https://www.illumina.com/science/technology/next-generation-sequencing/multiplex-sequencing.html. Printed on Nov. 4, 2021. 1 page.
[No Author Listed], Single-molecule real-time sequencing. Wikipedia entry/ Sep. 19, 2021. Retrieved from https://en.wikipedia.org/w/index.php?title+Singlemolecule_real-time_sequencing&oldid=1045146197. Printed on Nov. 4, 2021. 10 pages.
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
(Continued)

*Primary Examiner* — Narayan K Bhat
(74) *Attorney, Agent, or Firm* — Wolf, Greenfield & Sacks, P.C.

(57) ABSTRACT

The invention relates to an improved method for characterising a template polynucleotide. The method involves using a polymerase to prepare a modified polynucleotide which makes it easier to characterise that the template polynucleotide.

17 Claims, 21 Drawing Sheets

Specification includes a Sequence Listing.

(56) References Cited

U.S. PATENT DOCUMENTS 9,116,118 B2 8/2015 Turner et al.
9,145,623 B2 9/2015 Kavanagh et al.
9,150,918 B2 10/2015 Turner et al.
9,542,527 B2 1/2017 Travers et al.
9,546,400 B2 1/2017 Turner et al.
9,551,023 B2 1/2017 Turner et al.
9,556,480 B2 1/2017 Turner et al.
9,582,640 B2 2/2017 Travers et al.
9,600,626 B2 3/2017 Travers et al.
9,670,526 B2 6/2017 Kokoris et al.
9,678,056 B2 6/2017 Turner et al.
9,738,929 B2 8/2017 Turner et al.
9,957,560 B2 5/2018 Brown et al.
10,131,944 B2 11/2018 Bernick et al.
10,221,450 B2 3/2019 Heron et al.
10,227,632 B2 3/2019 Jarvius
10,501,767 B2 12/2019 Stoddart et al.
10,570,440 B2 2/2020 White et al.
10,597,713 B2 3/2020 Brown et al.
10,669,578 B2 * 6/2020 Clarke ................ C12Q 1/6869
10,851,409 B2 12/2020 Brown et al.
11,155,860 B2 10/2021 White et al.
11,168,363 B2 11/2021 Brown et al.
11,186,857 B2 11/2021 Stoddart et al.
11,261,487 B2 3/2022 Brown et al.
11,268,139 B2 3/2022 Lu
11,352,664 B2 6/2022 Mckeown
11,390,904 B2 7/2022 White
11,459,606 B2 10/2022 Mckeown
11,542,551 B2 * 1/2023 Clarke ................ C12Q 1/6869
11,560,589 B2 1/2023 Heron et al.
2001/0039039 A1 11/2001 Weissman et al.
2002/0028458 A1 3/2002 Lexow
2002/0094526 A1 7/2002 Bayley et al.
2002/0098530 A1 7/2002 Pfeifer et al.
2002/0132350 A1 9/2002 Suzuki et al.
2002/0142331 A1 10/2002 Fu et al.
2002/0177701 A1 11/2002 Weissman et al.
2002/0197618 A1 12/2002 Sampson
2003/0044816 A1 3/2003 Denison et al.
2003/0059778 A1 3/2003 Berlin et al.
2003/0087232 A1 5/2003 Christians et al.
2003/0099951 A1 5/2003 Akeson et al.
2003/0108902 A1 6/2003 Abarzua
2003/0118595 A1 6/2003 Niemeyer et al.
2003/0165936 A1 9/2003 Rabbani et al.
2003/0166137 A1 9/2003 Zuker et al.
2003/0211502 A1 11/2003 Sauer et al.
2003/0215881 A1 11/2003 Bayley et al.
2004/0055901 A1 3/2004 Petersen et al.
2004/0214177 A1 10/2004 Bension
2004/0229315 A1 11/2004 Lee et al.
2005/0042633 A1 2/2005 Williams
2005/0053961 A1 3/2005 Akeson et al.
2005/0142559 A1 6/2005 Makrigiorgos
2005/0221316 A1 10/2005 Pedersen et al.
2005/0227239 A1 10/2005 Joyce
2005/0260655 A1 11/2005 Liu et al.
2006/0063171 A1 3/2006 Akeson et al.
2006/0086626 A1 4/2006 Joyce
2006/0141516 A1 6/2006 Kobold et al.
2006/0147935 A1 7/2006 Linnarsson
2006/0292611 A1 12/2006 Berka et al.
2007/0015182 A1 1/2007 Abarzua
2007/0020640 A1 1/2007 McCloskey
2007/0031857 A1 2/2007 Makarov et al.
2007/0122885 A1 5/2007 Reeves et al.
2007/0224613 A1 9/2007 Strathmann
2007/0269825 A1 11/2007 Wang et al.
2007/0287151 A1 12/2007 Linnarsson
2008/0108082 A1 5/2008 Rank et al.
2008/0166724 A1 7/2008 Gerber et al.
2008/0206252 A1 8/2008 Pennica et al.
2008/0311582 A1 12/2008 Bayley et al.
2009/0098612 A1 4/2009 Rhee et al.
2009/0191598 A1 7/2009 Ruan et al.
2009/0256116 A1 10/2009 Shumaker-Parry et al.
2009/0269771 A1 10/2009 Schroeder
2009/0280538 A1 11/2009 Patel et al.
2009/0298075 A1 12/2009 Travers et al.
2010/0003560 A1 1/2010 Shibata
2010/0035254 A1 2/2010 Williams
2010/0035260 A1 2/2010 Olasagasti et al.
2010/0075309 A1 3/2010 Maxham et al.
2010/0075327 A1 3/2010 Maxham et al.
2010/0075328 A1 3/2010 Bjornson et al.
2010/0092960 A1 4/2010 Fehr
2010/0120098 A1 5/2010 Grunenwald et al.
2010/0121582 A1 5/2010 Pan et al.
2010/0221212 A1 9/2010 Stagliano et al.
2010/0221716 A1 9/2010 Flusberg et al.
2010/0276588 A1 11/2010 Syms
2010/0331194 A1 12/2010 Turner et al.
2011/0019186 A1 1/2011 Himmelhaus et al.
2011/0124518 A1 5/2011 Cantor
2011/0136676 A1 6/2011 Greene
2011/0214991 A1 9/2011 Kim et al.
2011/0224106 A1 9/2011 Eshoo et al.
2011/0281768 A1 11/2011 Travers et al.
2011/0287435 A1 11/2011 Grunenwald et al.
2011/0311965 A1 12/2011 Maglia et al.
2012/0010085 A1 1/2012 Rava et al.
2012/0015821 A1 1/2012 Raymond
2012/0058468 A1 3/2012 Mckeown
2012/0100530 A1 4/2012 Moysey et al.
2012/0107802 A1 5/2012 Stoddart et al.
2012/0196279 A1 8/2012 Underwood et al.
2012/0244525 A1 9/2012 Hendrickson
2013/0017978 A1 1/2013 Kavanagh et al.
2013/0048499 A1 2/2013 Mayer et al.
2013/0078624 A1 3/2013 Holmes et al.
2013/0143802 A1 6/2013 Chilkoti
2013/0195908 A1 8/2013 Leonetti et al.
2013/0203123 A1 8/2013 Nelson et al.
2013/0327644 A1 12/2013 Turner et al.
2014/0134618 A1 5/2014 Kokoris et al.
2014/0134629 A1 5/2014 Turner et al.
2014/0186823 A1 7/2014 Clarke et al.
2014/0206842 A1 7/2014 Majeed et al.
2014/0262784 A1 9/2014 Clarke et al.
2014/0296089 A1 10/2014 Holmes et al.
2014/0308661 A1 10/2014 Holmes et al.
2015/0008126 A1 1/2015 Maglia et al.
2015/0045257 A1 2/2015 Kavanagh et al.
2015/0152492 A1 6/2015 Brown et al.
2015/0167075 A1 6/2015 Turner et al.
2015/0175663 A1 6/2015 Yokoi et al.
2015/0197796 A1 7/2015 White et al.
2015/0218629 A1 8/2015 Heron et al.
2015/0265994 A1 9/2015 Hyde et al.
2015/0285781 A1 10/2015 Heron et al.
2015/0307934 A1 10/2015 Turner et al.
2016/0010147 A1 1/2016 Heron et al.
2016/0010148 A1 1/2016 Turner et al.
2016/0011169 A1 1/2016 Turner et al.
2016/0194677 A1 7/2016 Stoddart et al.
2016/0257942 A1 9/2016 Bruce et al.
2016/0281159 A1 9/2016 Brown et al.
2016/0362739 A1 12/2016 Brown et al.
2017/0002406 A1 1/2017 Bowen et al.
2017/0067101 A1 3/2017 Clarke et al.
2017/0226503 A1 8/2017 Strachan et al.
2017/0240955 A1 8/2017 White
2017/0314062 A1 11/2017 Kokoris et al.
2017/0321266 A1 11/2017 Mckeown
2018/0030506 A1 2/2018 Fujioka
2018/0051277 A1 2/2018 Godfrey et al.
2018/0291440 A1 10/2018 Mckeown
2018/0291441 A1 10/2018 Brown et al.
2019/0194722 A1 6/2019 Stoddart et al.
2019/0211390 A1 7/2019 Heron et al.
2019/0376132 A1 12/2019 Mckeown
2020/0002761 A1 1/2020 Mckeown
2020/0024655 A1 1/2020 Brown et al.

(56) References Cited

U.S. PATENT DOCUMENTS

| | | | |
|---|---|---|---|
| 2020/0032248 | A1 | 1/2020 | White et al. |
| 2020/0109396 | A1 | 4/2020 | Tsai et al. |
| 2020/0131549 | A1 | 4/2020 | Stoddart et al. |
| 2020/0239950 | A1 | 7/2020 | Brown et al. |
| 2020/0291452 | A1 | 9/2020 | White |
| 2020/0318179 | A1 | 10/2020 | Clarke et al. |
| 2022/0127669 | A1 | 4/2022 | Brown et al. |
| 2022/0145383 | A1 | 5/2022 | White et al. |
| 2022/0186274 | A1 | 6/2022 | Stoddart et al. |
| 2023/0046363 | A1 | 2/2023 | White |
| 2023/0065890 | A1 | 3/2023 | Mckeown |

FOREIGN PATENT DOCUMENTS

| | | | |
|---|---|---|---|
| CN | 105209634 | A | 12/2015 |
| CN | 105705656 | A | 6/2016 |
| DE | 112016000293 | T5 | 9/2017 |
| EP | 2682460 | A1 | 1/2014 |
| EP | 3470529 | A1 | 4/2019 |
| GB | 2130219 | A | 5/1984 |
| GB | 2237390 | A | 5/1991 |
| GB | 2453377 | A | 4/2009 |
| JP | H11-137260 | A | 5/1999 |
| JP | 2012-506704 | A | 3/2012 |
| WO | WO 1994/23065 | | 10/1994 |
| WO | WO 1999/05167 | | 2/1999 |
| WO | WO 2000/28312 | A1 | 5/2000 |
| WO | WO 2001/40516 | A2 | 6/2001 |
| WO | WO 2001/42782 | A1 | 6/2001 |
| WO | WO 2001/59453 | A2 | 8/2001 |
| WO | WO 2002/42496 | A2 | 5/2002 |
| WO | WO 2003/095669 | A1 | 11/2003 |
| WO | WO 2005/056750 | A2 | 6/2005 |
| WO | WO 2005/068656 | A1 | 7/2005 |
| WO | WO 2005/118877 | A2 | 12/2005 |
| WO | WO 2005/124888 | A1 | 12/2005 |
| WO | WO 2006/020775 | A2 | 2/2006 |
| WO | WO 2006/028508 | A2 | 3/2006 |
| WO | WO 2006/100484 | A2 | 9/2006 |
| WO | WO 2007/057668 | A1 | 5/2007 |
| WO | WO 2007/075987 | A2 | 7/2007 |
| WO | WO 2007/084103 | A2 | 7/2007 |
| WO | WO 2007/146158 | A1 | 12/2007 |
| WO | WO 2008/045575 | A2 | 4/2008 |
| WO | WO 2008/083554 | A1 | 7/2008 |
| WO | WO 2008/102120 | A1 | 8/2008 |
| WO | WO 2008/102121 | A1 | 8/2008 |
| WO | WO 2008/124107 | A1 | 10/2008 |
| WO | WO 2009/035647 | A1 | 3/2009 |
| WO | WO 2009/044170 | A1 | 4/2009 |
| WO | WO 2009/077734 | A2 | 6/2009 |
| WO | WO 2009/120372 | A2 | 10/2009 |
| WO | WO 2009/120374 | A2 | 10/2009 |
| WO | WO 2010/004265 | A1 | 1/2010 |
| WO | WO 2010/004273 | A1 | 1/2010 |
| WO | WO 2010/030683 | A1 | 3/2010 |
| WO | WO 2010/034018 | A2 | 3/2010 |
| WO | WO 2010/048605 | A1 | 4/2010 |
| WO | WO 2010/051773 | A1 | 5/2010 |
| WO | WO 2010/086602 | A1 | 8/2010 |
| WO | WO 2010/086603 | A1 | 8/2010 |
| WO | WO 2010/086622 | A1 | 8/2010 |
| WO | WO 2010/094040 | A1 | 8/2010 |
| WO | WO 2010/109107 | A1 | 9/2010 |
| WO | WO 2010/109197 | A2 | 9/2010 |
| WO | WO 2010/122293 | A1 | 10/2010 |
| WO | WO 2010/146349 | A1 | 12/2010 |
| WO | WO 2011/067559 | A1 | 6/2011 |
| WO | WO 2012/033524 | A2 | 3/2012 |
| WO | WO 2012/061832 | A1 | 5/2012 |
| WO | WO 2012/083249 | A2 | 6/2012 |
| WO | WO 2012/098561 | A2 | 7/2012 |
| WO | WO 2012/098562 | A2 | 7/2012 |
| WO | WO 2012/103545 | A1 | 8/2012 |
| WO | WO 2012/107778 | A2 | 8/2012 |
| WO | WO 2012/164270 | A1 | 12/2012 |
| WO | WO 2013/014451 | A1 | 1/2013 |
| WO | WO 2013/041878 | A1 | 3/2013 |
| WO | WO 2013/057495 | A2 | 4/2013 |
| WO | WO 2013/098561 | A1 | 7/2013 |
| WO | WO 2013/098562 | A2 | 7/2013 |
| WO | WO 2013/131962 | A1 | 9/2013 |
| WO | WO 2013/153359 | A1 | 10/2013 |
| WO | WO 2013/185137 | A1 | 12/2013 |
| WO | WO 2014/013259 | A1 | 1/2014 |
| WO | WO 2014/013260 | A1 | 1/2014 |
| WO | WO 2014/013262 | A1 | 1/2014 |
| WO | WO 2014/064443 | A2 | 5/2014 |
| WO | WO 2014/064444 | A1 | 5/2014 |
| WO | WO 2014/108810 | A2 | 7/2014 |
| WO | WO 2014/135838 | A1 | 9/2014 |
| WO | WO 2014/153408 | A1 | 9/2014 |
| WO | WO 2015/022544 | A1 | 2/2015 |
| WO | WO 2015/031909 | A1 | 3/2015 |
| WO | WO 2015/055981 | A2 | 4/2015 |
| WO | WO 2015/056028 | A1 | 4/2015 |
| WO | WO 2015/110777 | A1 | 7/2015 |
| WO | WO 2015/110813 | A1 | 7/2015 |
| WO | WO 2015/189636 | A1 | 12/2015 |
| WO | WO 2015/200609 | A1 | 12/2015 |
| WO | WO 2016/003814 | A1 | 1/2016 |
| WO | WO 2016/022557 | A1 | 2/2016 |
| WO | WO 2016/028887 | A1 | 2/2016 |
| WO | WO 2016/034591 | A2 | 3/2016 |
| WO | WO 2016/055777 | A2 | 4/2016 |
| WO | WO 2016/059363 | A1 | 4/2016 |
| WO | WO 2017/215500 | A1 | 12/2017 |

OTHER PUBLICATIONS

Altschul et al., Basic local alignment search tool. J Mol Biol. Oct. 5, 1990;215(3):403-10. Altschul, A protein alignment scoring system sensitive at all evolutionary distances. J Mol Evol. Mar. 1993;36(3):290-300.

Altschul, A protein alignment scoring system sensitive at all evolutionary distances. J Mol Evol. Mar. 1993;36(3):290-300.

Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Avrameas, Coupling of enzymes to proteins with glutaraldehyde. Use of the conjugates for the detection of antigens and antibodies. Immunochemistry. Jan. 1969;6(1):43-52.

Bayley et al., Stochastic sensors inspired by biology. Nature. Sep. 13, 2001;413(6852):226-30.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Berger et al., Universal bases for hybridization, replication and chain termination. Nucleic Acids Res. Aug. 1, 2000;28(15):2911-4.

Bowie et al., Deciphering the message in protein sequences: tolerance to amino acid substitutions. Science. Mar. 16, 1990;247(4948):1306-10.

(56) References Cited

OTHER PUBLICATIONS

Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Cheley et al., Stochastic sensing of nanomolar inositol 1,4,5-trisphosphate with an engineered pore. Chem Biol. Jul. 2002;9(7):829-38.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Cudic et al., Binding of Nucleotides in Water by Phenathridinium Bis(intercaland) Receptor Molecules. J. Chem. Soc., Chem. Commun., pp. 1073-1075 (1995).
Cui et al., Maize Mu transposon and its application in reverse genetic research. Bulletin of Agricultural Science and Technology. Dec. 31, 2010;1:35-38.
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dong et al., Amplified detection of nucleic acid by G-quadruplex based hybridization chain reaction. Biosens Bioelectron. Oct.-Dec. 2012;38(1):258-63. doi: 10.1016/j.bios.2012.05.042. Epub Jun. 8, 2012.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., 1994;116:6081-6088.
El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.
Erie et al., A dumbbell-shaped, double-hairpin structure of DNA: a thermodynamic investigation. Biochemistry. Nov. 3, 1987;26(22):7150-9.
Faller et al., The structure of a mycobacterial outer-membrane channel. Science. Feb. 20, 2004;303(5661):1189-92. doi: 10.1126/science.1094114.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

(56) References Cited

OTHER PUBLICATIONS

Gill et al., Nucleic acid isothermal amplification technologies: a review. Nucleosides Nucleotides Nucleic Acids. Mar. 2008;27(3):224-43. doi: 10.1080/15257770701845204.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
He et al., The carboxyl-terminal domain of bacteriophage T7 single-stranded DNA-binding protein modulates DNA binding and interaction with T7 DNA polymerase. J Biol Chem. Aug. 8, 2003;278(32):29538-45. doi: 10.1074/jbc.M304318200. Epub May 24, 2003.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Heredia et al., In vitro double transposition for DNA identification. Anal Biochem. Apr. 1, 2010;399(1):78-83. doi:10.1016/j.ab.2009.11.030. Epub Nov. 26, 2009.
Hobbs et al., SSB protein limits RecOR binding onto single-stranded DNA. J Biol Chem. Apr. 13, 2007;282(15):11058-67. Epub Feb. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hollis et al., Structure of the gene 2.5 protein, a single-stranded DNA binding protein encoded by bacteriophage T7. Proc Natl Acad Sci U S A. Aug. 14, 2001;98(17):9557-62. doi: 10.1073/pnas.171317698. Epub Jul. 31, 2001.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82 {1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Hwang et al., Electrical behavior of droplet interface bilayer networks: experimental analysis and modeling. J Am Chem Soc. Sep. 26, 2007;129(38):11854-64. Epub Sep. 1, 2007.
Hyland et al., The DNA binding domain of the gene 2.5 single-stranded DNA-binding protein of bacteriophage T7. J Biol Chem. Feb. 28, 2003;278(9):7247-56. doi: 10.1074/jbc.M210605200. Epub Dec. 20, 2002.
Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kahvejian et al., Making single-molecule sequencing a reality. American Laboratory. Jan. 1, 2008;40(20):48-53. www.americanlaboratory.com/913-Technical-Articles/780-Making-Single-Molecule-Sequencing-a-Reality/. Last accessed Dec. 10, 2021.
Kalisch et al., Covalently linked sequencing primer linkers (splinkers) for sequence analysis of restriction fragments. Gene. 1986;44(2-3):263-70.
Kanan et al., Reaction discovery enabled by DNA-templated synthesis and in vitro selection. Nature. Sep. 30, 2004;431(7008):545-9.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Keyser, Controlling molecular transport through nanopores. J R Soc Interface. Oct. 7, 2011;8(63):1369-78. doi: 10.1098/rsif.2011.0222. Epub Jun. 29, 2011.
Khulbe et al., DNA translocation through a-hemolysin nanopores with potential application to macromolecular data storage. Journal Applied Physics, vol. 97(104317):1-7 (2005).
Kocalka et al., Rapid and efficient DNA strand cross-linking by click chemistry. Chembiochem. May 23, 2008;9(8):1280-5. doi:10.1002/cbic.200800006.
Kolb et al., Click Chemistry: Diverse Chemical Function from a Few Good Reactions. Angew Chem Int Ed Engl. Jun. 1, 2001;40(11):2004-2021.
Kovall et al., Toroidal structure of lambda-exonuclease. Science. Sep. 19, 1997;277(5333):1824-7.
Kozlov et al., Regulation of Single-stranded DNA Binding by the C Termini of *Esherichia coli* Single-stranded DNA-binding (SBB) Protein. J. Biol. Chem. May 28, 2010;285(22):17246-52.
Kuipers, Random mutagenesis by using mixtures of dNTP and dITP in PCR. Methods Mol Biol. 1996;57:351-6. doi: 10.1385/0-89603-332-5:351.
Langecker et al., Synthetic lipid membrane channels formed by designed DNA nanostructures. Science. Nov. 16, 2012;338(6109):932-6. doi: 10.1126/science.1225624.
Lazar et al., Transforming growth factor alpha: mutation of aspartic acid 47 and leucine 48 results in different biological activities. Mol Cell Biol. Mar. 1988;8(3):1247-52.
Li et al., DNA molecules and configurations in a solid-state nanopore microscope. Nat Mater. Sep. 2003;2(9):611-5. Epub Aug. 24, 2003.
Liang, Structure of outer membrane protein G by solution NMR spectroscopy. Proc Natl Acad Sci U S A. Oct. 9, 2007;104(41):16140-5. doi: 10.1073/pnas.0705466104. Epub Oct. 2, 2007.

(56) References Cited

OTHER PUBLICATIONS

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Locher et al., Transmembrane signaling across the ligand-gated FhuA receptor: crystal structures of free and ferrichrome-bound states reveal allosteric changes. Cell. Dec. 11, 1998;95(6):771-8. doi: 10.1016/s0092-8674(00)81700-6.
Lovett et al., Identification and purification of a single-stranded-DNA-specific exonuclease encoded by the recJ gene of *Escherichia coli*. Proc Natl Acad Sci U S A. Apr. 1989;86(8):2627-31.
Lovrinovic et al., Rapid synthesis of DNA-cysteine conjugates for expressed protein ligation. Biochem Biophys Res Commun. Sep. 30, 2005;335(3):943-8.
Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas.0800741105. Epub Jun. 30, 2008.
Luo et al., Influence of polymer-pore interactions on translocation. Phys Rev Lett. Oct. 5, 2007;99(14):148102. Epub Oct. 1, 2007.
Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
Maglia et al., Analysis of single nucleic acid molecules with protein nanopores. Methods Enzymol. 2010;475:591-623. doi: 10.1016/S0076-6879(10)75022-9.
Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.
Manosas et al., Magnetic tweezers for the study of DNA tracking motors. Methods Enzymol. 2010;475:297-320. doi: 10.1016/S0076-6879(10)75013-8.
Martin et al., Nanoscale protein pores modified with PAMAM dendrimers. J Am Chem Soc. Aug. 8, 2007;129(31):9640-9. Epub Jul. 18, 2007.
Martînez et al., The mRNA cap structure stimulates rate of poly(A) removal and amplifies processivity of degradation. J Biol Chem. Jul. 27, 2001;276(30):27923-9. Epub May 18, 2001.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.
Matson et al., The gene 4 protein of bacteriophage T7. Characterization of helicase activity. J Biol Chem. Nov. 25, 1983;258(22):14017-24.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.
Miner et al., Molecular barcodes detect redundancy and contamination in hairpin-bisulfite PCR. Nucleic Acids Res. 2004; 32(17): e135. EPub Sep. 30, 2004. doi: 10.1093/nar/gnh132.
Mitchel et al., Heteroduplex DNA position defines the roles of the Sgs1, Srs2, and Mph1 helicases in promoting distinct recombination outcomes. PLoS Genet. 2013;9(3):e1003340. doi: 10.1371/journal.pgen.1003340. Epub Mar. 14, 2013.
Mitchell et al., Chemical tags facilitate the sensing of individual DNA strands with nanopores. Angew Chem Int Ed Engl. 2008;47(30):5565-8. doi:10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Mol et al., Structure and function of the multifunctional DNA-repair enzyme exonuclease III. Nature. Mar. 23, 1995;374(6520):381-6.
Montal et al., Formation of bimolecular membranes from lipid monolayers and a study of their electrical properties. Proc Natl Acad Sci U S A. Dec. 1972;69(12):3561-6.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakai et al., Handoff from recombinase to replisome: insights from transposition. Proc Natl Acad Sci U S A. Jul. 17, 2001;98(15):8247-54. doi: 10.1073/pnas.111007898.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niemeyer et al., DNA-directed assembly of bienzymic complexes from in vivo biotinylated NAD(P)H:FMN oxidoreductase and luciferase. Chembiochem. Mar. 1, 2002;3(2-3):242-5.
Nikolov et al., Behavior of giant vesicles with anchored DNA molecules. Biophys J. Jun. 15, 2007;92(12):4356-68. Epub Mar. 23, 2007.
North et al., Host factors that promote transpososome disassembly and the PriA-PriC pathway for restart primosome assembly. Mol Microbiol. Jun. 2005;56(6):1601-16.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
Paner et al., Studies of DNA dumbbells. III. Theoretical analysis of optical melting curves of dumbbells with a 16 base-pair duplex stem and Tn end loops (n = 2, 3, 4, 6, 8, 10, 14). Biopolymers. Jul. 1992;32(7):881-92.
Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.
Pettersson et al., Generations of sequencing technologies. Genomics. Feb. 2009;93(2):105-11. doi: 10.1016/j.ygeno.2008.10.003. Epub Nov. 21, 20081.
Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.
Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.
Rezende et al., Essential amino acid residues in the single-stranded DNA-binding protein of bacteriophage T7. Identification of the dimer interface. J Biol Chem. Dec. 27, 2002;277(52):50643-53. doi: 10.1074/jbc.M207359200. Epub Oct. 12, 2002.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.

(56) References Cited

OTHER PUBLICATIONS

Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Schneider et al., DNA sequencing with nanopores. Nat Biotechnol. Apr. 10, 2012;30(4):326-8. doi: 10.1038/nbt.2181.
Seeman, Nucleic acid junctions and lattices. J Theor Biol. Nov. 21, 1982;99(2):237-47.
Seo et al., Click chemistry to construct fluorescent oligonucleotides for DNA sequencing. J Org Chem. Jan. 24, 2003;68(2):609-12.
Seol et al., Stretching of homopolymeric RNA reveals single-stranded helices and base-stacking. Phys Rev Lett. Apr. 13, 2007;98(15):158103. Epub Apr. 12, 2007.
Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.
Shendure et al., Overview of DNA sequencing strategies. Curr Protoc Mol Biol. Jan. 2008;Chapter 7:Unit 7.1. doi: 10.1002/0471142727.mb0701s81.
Shin et al., Kinetics of a reversible covalent-bond-forming reaction observed at the single-molecule level. Angew Chem Int Ed Engl. Oct. 4, 2002;41(19):3707-9; 3523.
Singleton et al., Structure and mechanism of helicases and nucleic acid translocases. Annu Rev Biochem. 2007;76:23-50. doi: 10.1146/annurev.biochem.76.052305.115300.
Skipper et al., DNA transposon-based gene vehicles—scenes from an evolutionary drive. J Biomed Sci. Dec. 9, 2013;20(1):92. doi: 10.1186/1423-0127-20-92.
Smeets et al., Salt dependence of ion transport and DNA translocation through solid-state nanopores. Nano Lett. Jan. 2006;6(1):89-95.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
Song et al., Structure of staphylococcal alpha-hemolysin, a heptameric transmembrane pore. Science. Dec. 13, 1996;274(5294):1859-66.
Spee et al., Efficient random mutagenesis method with adjustable mutation frequency by use of PCR and dITP. Nucleic Acids Res. Feb. 11, 1993;21(3):777-8. doi: 10.1093/nar/21.3.777.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Tadey et al., Capillary electrophoretic separation of nucleotide isomers via complexation with cyclodextrin and borate. J Chromatogr B Biomed Appl. Jul. 15, 1994;657(2):365-72.
Thomas et al., Processivity of DNA exonucleases. J Biol Chem. Jan. 26, 1978;253(2):424-9.
Tohda et al., "Channel Mimetic Sensing Membranes for Nucleotides Based on Multitopic Hydrogen Bonding," Israel Journal of Chemistry, vol. 37:267-275 (1997).
Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tung et al., Preparation and applications of peptide-oligonucleotide conjugates. Bioconjug Chem. Sep.-Oct. 2000;11(5):605-18.
United States District Court for the District of Delaware Order. *Pacific Biosciences of California, Inc.* v. *Oxford Nanopore Technolgoies, Inc.* Civil Action No. 17-275-RGA. Nov. 9, 2017.
Van De Goor, Nanopore Detection: Threading DNA Through a Tiny Hole. PharmaGenomics, vol. 4 (3):28-30 (2004).
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., A simple and reproducible method for directed evolution: combination of random mutation with dITP and DNA fragmentation with endonuclease V. Mol Biotechnol. Jan. 2013;53(1):49-54. doi: 10.1007/s12033-012-9516-9.
Wang et al., Bioconjugation by copper(I)-catalyzed azide-alkyne [3 + 2] cycloaddition. J Am Chem Soc. Mar. 19, 2003;125(11):3192-3.
Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
Xie et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus thermophilus HB8 and its core domain. Nucleic Acids Res. Nov. 15, 2001;29(22):4617-24.
Yamashita et al., Crystal structures of the OmpF porin: function in a colicin translocon. Embo J. Aug. 6, 2008;27(15):2171-80. doi: 10.1038/emboj.2008.137. Epub Jul. 17, 2008.

* cited by examiner

SAMPLE PREPARATION METHOD

RELATED APPLICATIONS

This Application is a continuation of U.S. application Ser. No. 16/855,096, filed Apr. 22, 2020, which is continuation of U.S. application Ser. No. 15/120,186, filed Aug. 19, 2016, which is a national stage filing under 35 U.S.C. § 371 of International Patent Application No. PCT/GB2015/050483, which has an international filing date of Feb. 19, 2015, and claims foreign priority benefits under 35 U.S.C. § 119(a)-(d) or 35 U.S.C. § 365(b) of British Application No. 1403096.9, filed Feb. 21, 2014, the contents of each of which are herein incorporated by reference in their entireties.

REFERENCE TO AN ELECTRONIC SEQUENCE LISTING

The contents of the electronic sequence listing (O036670039US02-SEQ-CBD.xml; Size: 87,557 bytes; and Date of Creation: Nov. 10, 2022) is herein incorporated by reference in its entirety.

FIELD OF THE INVENTION

The invention relates to an improved method for characterising a template polynucleotide. The method involves using a polymerase to prepare a modified polynucleotide which makes it easier to characterise than the template polynucleotide.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

SUMMARY OF THE INVENTION

The inventors have surprisingly demonstrated that it is possible to modify a template polynucleotide to produce a modified polynucleotide which provides different information from the original template polynucleotide when it is characterized using a transmembrane pore, such as by strand sequencing. Subsequent characterisation of the modified polynucleotide using a transmembrane pore allows the character of the template polynucleotide to be more easily determined.

The improved method uses a polymerase and a population of free nucleotides which are capable of hybridising to the template polynucleotide. The polymerase uses the template polynucleotide as a template to form a modified polynucleotide from the population of free nucleotides. The identity of the free nucleotides is chosen such that the polymerase replaces one or more of the nucleotide species in the template polynucleotide with a different nucleotide species when forming the modified polynucleotide. For instance, the polymerase may replace deoxyguanosine monophosphate (dGMP) in the template polynucleotide with deoxyinosine monophosphate (dIMP) in the modified polynucleotide.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the template polynucleotide with different nucleotide species in the modified nucleotide, the modified polynucleotide contains k-mers which differ from those in the template polynucleotide. The different k-mers in the modified polynucleotide are capable of producing different current measurements from the k-mers in the template polynucleotide and so the modified polynucleotide provides different information from the template polynucleotide. The additional information from the modified polynucleotide can make it easier to characterise the template polynucleotide. In some instances, the modified polynucleotide itself may be easier to characterise. For instance, the modified polynucleotide may be designed to include k-mers with an increased separation or a clear separation between their current measurements or k-mers which have a decreased noise. The information from the modified polynucleotide can also be combined with information from the template polynucleotide to improve the overall accuracy of characterisation.

Accordingly, the invention provides a method of characterising a template polynucleotide, comprising:

a) contacting the template polynucleotide with a polymerase and a population of free nucleotides under conditions in which the polymerase forms a modified polynucleotide using the template polynucleotide as a template, wherein the polymerase replaces one or more of the nucleotide species in the template polynucleotide with a different nucleotide species when forming the modified polynucleotide;

b) contacting the modified polynucleotide with a transmembrane pore such that the modified polynucleotide moves through the pore; and c) taking one or more measurements as the modified polynucleotide moves with respect to the pore wherein the measurements are indicative of one or more characteristics of the modified polynucleotide and thereby characterising the template polynucleotide. The polymerase preferably does not form a complementary polynucleotide if the template polynucleotide is RNA.

The invention also provides a kit for characterising a template polynucleotide comprising (a) a polymerase and (b) a population of free nucleotides comprising a nucleotide species which differs from one or more of the nucleotide species in the template polynucleotide, wherein the polymerase is capable of forming a modified polynucleotide from the free nucleotides using the template polynucleotide as a template and wherein the polymerase is capable of replacing one or more of the nucleotide species in the template polynucleotide with the different nucleotide species.

The invention further provides a method of characterising a homopolynucleotide, comprising:

a) contacting the homopolynucleotide with a polymerase and a population of free nucleotides under conditions in which the polymerase forms a modified polynucleotide using the homopolynucleotide as a template, wherein the modified polynucleotide is not the reverse complement of the homopolynucleotide;

b) contacting the modified polynucleotide with a transmembrane pore such that the modified polynucleotide moves through the pore; and c) taking one or more measurements as the modified polynucleotide moves with respect to the pore wherein the measurements are indicative of one or more characteristics of the modified polynucleotide and thereby characterising the homopolynucleotide.

DESCRIPTION OF THE SEQUENCE LISTING

Figure 1:
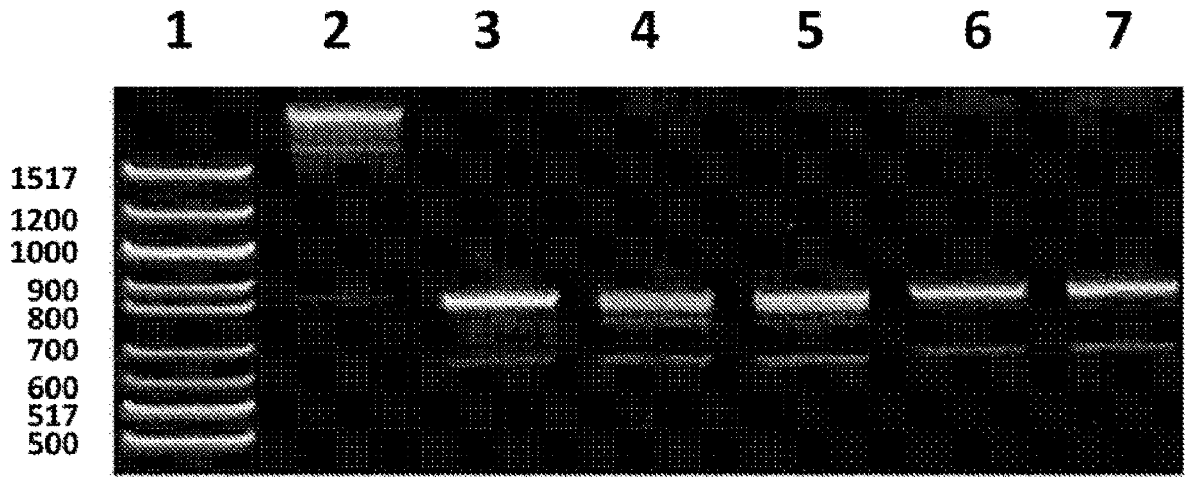
FIG. 1 shows a PAGE of a number of DNA samples produced using the method outlined in Example 1. Lane 1 corresponds to a DNA ladder (masses of the bands are shown on the left-hand side of the gel (1517, 1200, 1000, 900, 800, 700, 600, 517 and 500 bps)). Lane 2 shows the ssDNA control strand (SEQ ID NO: 34 attached at its 3' end to four iSpC3 spacers which are attached at the opposite end to SEQ ID NO: 41). Lane 3 shows the dsDNA control (SEQ ID NO: 34 is attached at its 3' end to four iSpC3 spacers which are attached at the opposite end to the 5' end of SEQ ID NO: 38). Lane 4 shows the dsDNA produced by providing the following dNTP's—dATP, dTTP, dGTP and dCTP. Lane 5 shows the dsDNA sample produced by providing the following dNTP's—dATP, dCTP, dGTP and 5-propynyl-2'-deoxyuridine-5'-triphosphate. Lane 6 shows the dsDNA sample produced by providing the following dNTP's—dATP, dCTP, dTTP and 6-thio-2'-deoxyguanosine-5'-triphosphate. Lane 7 shows the dsDNA sample produced by providing the following dNTP's—dATP, dCTP, 5-propynyl-2'-deoxyuridine-5'-triphosphate and 6-thio-2'-deoxyguanosine-5'-triphosphate
Figure 2:
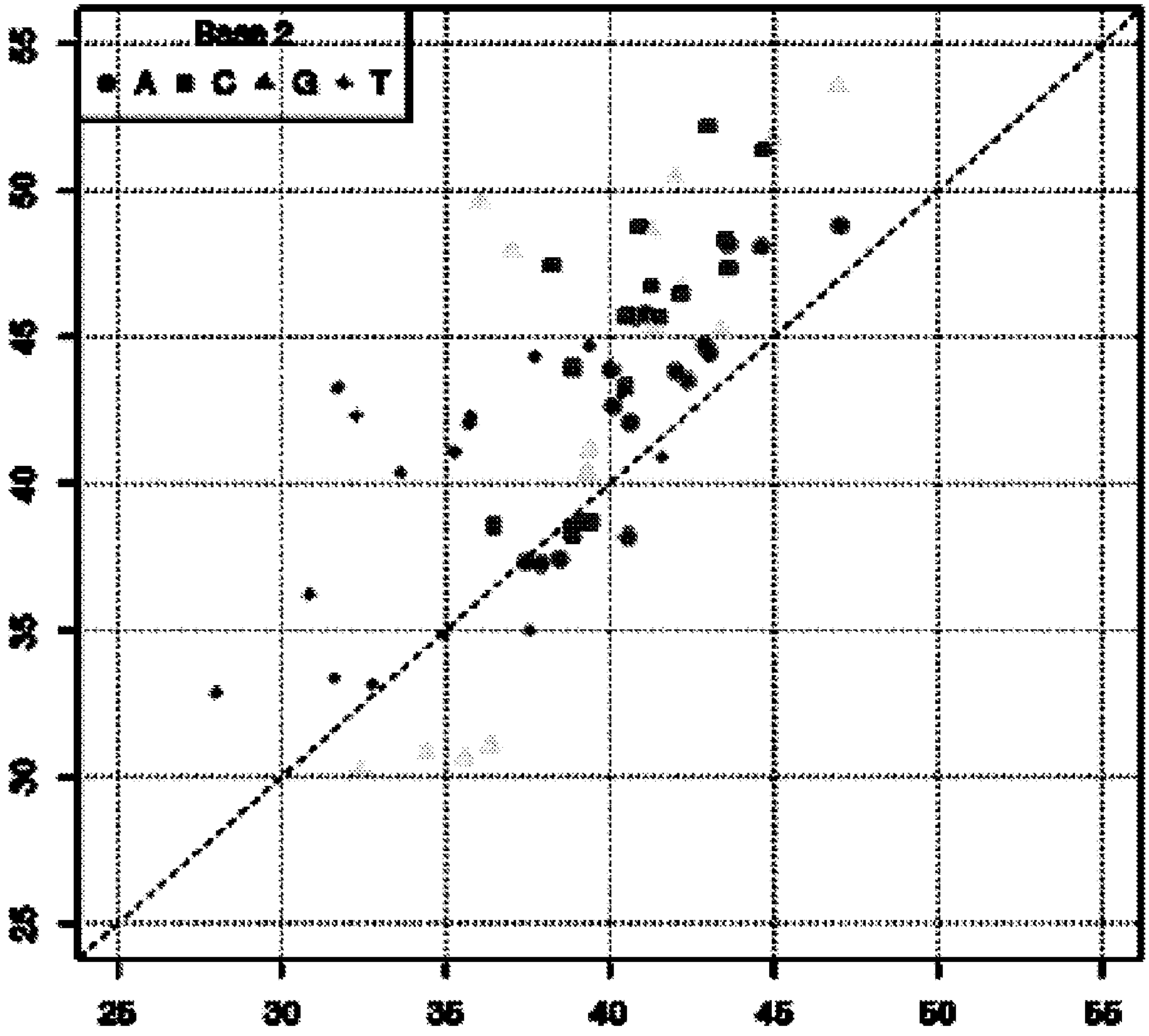
FIG. 2 shows a diagonal dot plot for the modified DNA construct which was made up of C, A, G and 5-propynyl-2'-deoxyuridine-5'-triphosphate. The diagonal dot plot displays the current level for each base combination in the modified strand plotted against its equivalent in an unmodified strand, such that the large changes in the current-sequence relationship are represented by large displacements from the diagonal.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N ((α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3'direction (neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows the amino acid sequence for the Klenow fragment.

SEQ ID NO: 27 shows the polynucleotide sequence, used in Example 1, for a 600 bp fragment of lambda DNA. This sequence shows the sense sequence of dsDNA.

SEQ ID NO: 28 shows the polynucleotide sequence of a primer used in Example 1.

SEQ ID NO: 29 shows the polynucleotide sequence of a primer used in Example 1.

SEQ ID NO: 30 shows the polynucleotide sequence used in Example 1. SEQ ID NO: 30 is attached at its 5 end to 28 iSpC3 spacers which are attached at the opposite end to two thymines. SEQ ID NO: 30 is attached at the 3' end to four iSpC3 spacers which are attached at the opposite end to SEQ ID NO: 31. SEQID NO: 30 is attached in another polynucleotide sequence to four iSpC3 spacers which are attached at the opposite end to SEQ ID NO: 33.

SEQ ID NO: 31 shows the polynucleotide sequence used in Example 1 and 6. In Example 1 SEQ ID NO: 31 is attached at the 3' end to four iSpC3 spacers which are attached at the opposite end to SEQ ID NO: 30.

SEQ ID NO: 32 shows the polynucleotide sequence of a primer used in Example 1. The 5' end of the sequence contains a phosphate group.

SEQ ID NO: 33 shows a polynucleotide sequence used in Example 1. SEQ ID NO: 33 is attached at its 5' end to four iSpC3 spacers which are attached at the opposite end to SEQ ID NO: 30.

SEQ ID NO: 34 shows the polynucleotide sequence used in Examples 2-5. SEQ ID NO: 34 is attached at its 3' to four iSpC3 spacers which are attached at the opposite end to the 5' end of SEQ ID NO: 38.

SEQ ID NO: 35 shows a polynucleotide sequence used in Example 6.

SEQ ID NO: 36 shows a polynucleotide sequence used in Example 6 and 7.

SEQ ID NO: 37 shows a polynucleotide sequence used in Example 6.

SEQ ID NO: 38 shows a polynucleotide sequence used in Examples 2-5. SEQ ID NO: 38 is attached to four iSpC3 spacers which are attached at the opposite end to the 3' end of SEQ ID NO: 35.

SEQ ID NO: 39 shows a polynucleotide sequence used in Example 2. SEQ ID NO: 39 is attached at its 3' end to four iSpC3 spacers which are attached at the opposite end to the 5' end of SEQ ID NO: 40.

SEQ ID NO: 40 shows a polynucleotide sequence used in Example 2. SEQ ID NO: 40 is attached at its 5' end to four uracil bases and four iSpC3 spacers which were attached at the opposite end to the 3' end of SEQ ID NO: 39.

SEQ ID NO: 41 shows a polynucleotide sequence used in Example 1.

SEQ ID NO: 42 shows a polynucleotide sequence used in Examples 1-8. Attached to the 3' end of SEQ ID NO: 42 is six iSp18 spacer which are attached at the opposite end to two thymines and a 3' cholesterol TEG.

SEQ ID NO: 43 shows a polynucleotide sequence used in Example 7. The 5' end of the sequence contains a phosphate group. SEQ ID NO: 44 shows a polynucleotide sequence used in Example 7. The 5' end of the sequence contains a phosphate group.

SEQ ID NO: 45 shows a polynucleotide sequence used in Examples 6 and 7.

SEQ ID NO: 46 shows a polynucleotide sequence used in Examples 6 and 7.

SEQ ID NO: 47 shows a polynucleotide sequence used in Example 6.

SEQ ID NO: 48 shows a polynucleotide sequence used in Example 6.

SEQ ID NO: 49 shows a polynucleotide sequence used in Example 6.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms “a”, “an”, and “the” include plural referents unless the content clearly dictates otherwise. Thus, for example, reference to “a polynucleotide” includes “polynucleotides”, reference to “a polymerase” includes two or more such polymerase, reference to “a transmembrane pore” includes two or more such pores, and the like.

All publications, patents and patent applications cited herein, whether supra or infra, are hereby incorporated by reference in their entirety.

Method of the Invention

The present invention provides a method of characterising, such as sequencing, a template polynucleotide. The template polynucleotide is the polynucleotide that will ultimately be characterised, or sequenced, in accordance with the invention. This is discussed in more detail below.

An important component of sequencing polynucleotides using strand sequencing is the discrimination of polymer units made up of k nucleotides where k is a positive integer (i.e. ‘k-mers’). In the past, to achieve k-mer discrimination the polynucleotide has been passed through a transmembrane pore, such as a mutant of hemolysin. This has provided current signatures that have been shown to be sequence dependent. It has also been shown that a large number of nucleotides (i.e. a high value of k) contribute to the observed current, making a direct relationship between observed current and polynucleotide sequence challenging. In addition, it has been observed that when polynucleotides are moved through a pore, some current states show high variance. It has also been shown that some mutant pores exhibit higher variance than others.

Pores produced from mutated MspA monomers may display an increased current range, which makes it easier to discriminate between different k-mers, and/or a reduced variance of states, which increases the signal-to-noise ratio. In addition, the number of nucleotides contributing to the current (i.e. the value of k) as the polynucleotide moves through pores constructed from the MspA mutants is decreased. This makes it easier to identify a direct relationship between the observed current as the polynucleotide moves through the pore and the polynucleotide sequence. The signals generated using such pores may still be quite complex and so it remains challenging to sequence certain polynucleotides.

The method involves the formation of a modified polynucleotide. The modified polynucleotide includes one or more modified k-mers which provide different current measurements from the k-mers in the template polynucleotide. The one or more modified k-mers preferably have an increased separation or a clear separation from the k-mers in the template polynucleotide and/or the other k-mers in the modified polynucleotide. The one or more modified k-mers preferably have a decreased (or lower) noise than the k-mers in the template polynucleotide and/or the other k-mers in the template polynucleotide. In some embodiments, the modified polynucleotide comprises one or more k-mers that are easier to characterise (for instance because of an increased or clear separation or decreased noise), but also one or more k-mers which are more difficult to characterise (for instance because of a decreased or lack of separation or increased noise).

The modified polynucleotide provides different information from the template polynucleotide, especially when using strand sequencing. The modified polynucleotide is preferably easier to characterise than the template polynucleotide, especially using strand sequencing. The modified polynucleotide is characterised in order to facilitate the characterisation of the template polynucleotide. Although it is not part of the method of the invention, the template polynucleotide may itself be characterised by contacting the template polynucleotide with a transmembrane pore such that it moves through the pore and by taking one or more measurements as the template polynucleotide moves with respect to the pore wherein the measurements are indicative of one or more characteristics of the template polynucleotide. The information about the character of the template polynucleotide itself may then be used in conjunction with the different information derived from the modified polynucleotide in accordance with the invention to more easily characterise the template polynucleotide.

The method of the invention is particularly advantageous for strand sequencing because the modified polynucleotide provides a different signal from the signal provided if the template polynucleotide is itself sequenced. This different information can be used to facilitate the sequencing of the template polynucleotide, especially if the template polynucleotide has itself undergone strand sequencing.

The method of the invention also has other advantages. For instance, the one or more different nucleotide species in the modified polynucleotide may also be designed to facilitate the addition of one or more chemical groups to the modified polynucleotide.

Template Polynucleotide

The method of the invention involves the modification of a template polynucleotide for characterisation. The template polynucleotide is the polynucleotide that will ultimately be characterised, or sequenced, in accordance with the invention. It may also be called the target polynucleotide or the polynucleotide of interest.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the template polynucleotide can be oxidized or methylated. One or more nucleotides in the template polynucleotide may be damaged. For instance, the polynucleotide may comprise a pyrimidine dimer. Such dimers are typically associated with damage by ultraviolet light and are the primary cause of skin melanomas. One or more nucleotides in the template polynucleotide may be modified, for instance with a label or a tag. Suitable labels are described below. The template polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the template polynucleotide may be attached to each other in any manner. The nucleotides are typically attached by their sugar and phosphate groups as in nucleic acids. The nucleotides may be connected via their nucleobases as in pyrimidine dimers.

The template polynucleotide may be single stranded or double stranded. At least a portion of the polynucleotide is preferably double stranded.

The template polynucleotide can be a nucleic acid, such as deoxyribonucleic acid (DNA) or ribonucleic acid (RNA). The template polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA), bridged nucleic acid (BNA) or other synthetic polymers with nucleotide side chains.

The template polynucleotide is preferably DNA and the nucleotide species in the DNA preferably include deoxyadenosine monophosphate (dAMP), deoxyguanosine monophosphate (dGMP), deoxythymidine monophosphate (dTMP), deoxycytidine monophosphate (dCMP) and deoxymethylcytidine monophosphate.

Alternatively, the template polynucleotide is preferably RNA and the nucleotide species in the RNA preferably include adenosine monophosphate (AMP), guanosine monophosphate (GMP), uridine monophosphate (UMP), cytidine monophosphate (CMP) and 5-methylcytidine monophosphate.

The template polynucleotide can be any length. For example, the template polynucleotide can be at least 10, at least 50, at least 100, at least 150, at least 200, at least 250, at least 300, at least 400 or at least 500 nucleotide pairs in length. The template polynucleotide can be 1000 or more nucleotide pairs, 5000 or more nucleotide pairs in length or 100000 or more nucleotide pairs in length.

The template polynucleotide is typically present in any suitable sample. The invention is typically carried out on a sample that is known to contain or suspected to contain the template polynucleotide. Alternatively, the invention may be carried out on a sample to confirm the identity of one or more template polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Polymerase

The template polynucleotide is contacted with a polymerase. The polymerase may be any of those discussed below with reference to the polynucleotide binding protein. The polymerase is preferably Klenow or 9o North.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 9o North. A primer or a 3' hairpin is typically used as the nucleation point for polymerase extension.

Population of Free Nucleotides and Replacing Nucleotide Species

The template polynucleotide is contacted with a population of free nucleotides. The polymerase uses the free nucleotides to form the modified polynucleotide based on the template polynucleotide. The identities of the free nucleotides in the population determine the composition of the modified polynucleotide.

Many of the examples of different nucleotide species given below refer to their monophosphate form. This is because nucleotides contained in polynucleotides (such as the modified polynucleotide) are typically in their monophosphate form. When contacted with the polymerase, the free nucleotides in the population may be in their diphosphate form or triphosphate form or may comprise more than three phosphates, such as four or five phosphates. As a result, any of the nucleotides discussed below may have more than one phosphate when in their free form in the population. The different nucleotide species in the Examples are described with reference to their form in the population of free nucleotides, i.e. as triphosphates.

Each free nucleotide in the population is capable of hybridising or binding to one or more of the nucleotide species in the template polynucleotide. Each free nucleotide in the population is typically capable of specifically hybridising or specifically binding to (i.e. complementing) one or more of the nucleotide species in the template polynucleotide. A nucleotide specifically hybridises or specifically binds to (i.e. complements) a nucleotide in the template polynucleotide if it hybridises or binds more strongly to the nucleotide than to the other nucleotides in the template nucleotide. This allows the polymerase to use complementarity (i.e. base pairing) to form the modified polynucleotide using the template polynucleotide. Typically, each free nucleotide specifically hybridises or specifically binds to (i.e. complements) one of the nucleotides in the template polynucleotide. In some embodiments, a different nucleotide species used in the invention is capable of specifically hybridising or specifically binding to (i.e. complementing) more than one nucleotide species in the template polynucleotide. Universal nucleotides that are useful in these embodiments are discussed in more detail below.

Each different nucleotide species is capable of specifically hybridising or specifically binding to (i.e. complementing) the nucleotide species in the template polynucleotide which is complementary to the nucleotide species it is replacing. For instance, for a DNA template, the different nucleotide species being used to replace dAMP is capable of specifically hybridising or specifically binding to (i.e. complementing) dTMP. Each different nucleotide species used in the method typically hybridises or binds less strongly to those nucleotide species in the template polynucleotide which not are complementary to the nucleotide species it is replacing. For instance, for a DNA template, the different nucleotide species being used to replace dAMP is typically capable of hybridising or binding to dTMP more strongly than it hybridises or binds to dAMP, dGMP or dCMP. A skilled person can design suitable populations of free nucleotides. In some embodiments, the same different nucleotide species is used to replace different nucleotides species in the template polynucleotide. In such embodiments, the different nucleotide species is capable of specifically hybridising or specifically binding to (i.e. complementing) two or more nucleotide species in the template polynucleotide. This means that the different nucleotide species binds more strongly to the two or more nucleotide species it is replacing than the other nucleotides in the template polynucleotide. Universal nucleotides that are useful in these embodiments are discussed in more detail below.

Each free nucleotide is capable of being handled by the polymerase and incorporated into the modified polynucleotide.

The identities of the free nucleotides are such that the polymerase replaces one or more of the nucleotide species in the template polynucleotide with a different nucleotide species when forming the modified polynucleotide. For instance, the polymerase may replace all instances of dGMP in the template polynucleotide with deoxyinosine monophosphate (dIMP) or a modified version of dAMP in the modified polynucleotide. The one or more nucleotide species in the template polynucleotide that are being replaced do not typically appear in the modified polynucleotide.

The method of the invention is illustrated below.

```
Template ...ATGCATGCA...

Modified ...XACGXACGX...
```

In the illustration above, both strands are DNA. The template polynucleotide is shown on the top. The modified nucleotide is shown on the bottom. The polymerase has replaced the nucleotide species T (i.e. dTMP) with a different nucleotide species X in the modified polynucleotide. The different nucleotide species may be any of those discussed below. In order to do this, the template polynucleotide is contacted with a polymerase and a population of A, X, G and C. The polymerase is capable of handling X and inserting X at positions where T should appear in the modified polynucleotide, i.e. at positions where A (the nucleotide complementary to T) is present in the template polynucleotide.

One or more of the free nucleotides in the population are nucleotides which differ from the one or more nucleotide species being replaced. These are used to replace the one or more nucleotide species and are discussed in more detail below. The remaining nucleotides in the population are typically nucleotides present in the template polynucleotide. These may be any of the nucleotides discussed above.

Any number of nucleotide species in the template polynucleotide may be replaced with a different nucleotide species. For instance, the polymerase may replace two, three, four, five, six, seven, eight or more of the nucleotide species in the template polynucleotide with a different nucleotide when forming the modified polynucleotide. Wild-type DNA, such as human DNA, may contain more than four nucleotide species (i.e. more than just dAMP, dTMP, dGMP and dCMP) because of the plurality of naturally occurring nucleotide modifications. The polymerase may replace all of the nucleotide species in the template polynucleotide with a different nucleotide when forming the modified polynucleotide. For instance, the polymerase may replace dAMP, dTMP, dGMP and dCMP with modified versions of themselves, such as modified versions each comprising a halogen atom. This can be achieved for template DNA by contacting the DNA with a polymerase and a population of free nucleotides containing the modified versions of dAMP, dTMP, dGMP and dCMP.

In some preferred embodiments, the polymerase replaces each of the two or more nucleotide species in the template polynucleotide with a distinct nucleotide. In other words, each nucleotide species is replaced with distinct nucleotide. For instance, the polymerase may replace dAMP with a modified version of dAMP and replace dTMP with modified version of dTMP. This can be achieved for template DNA by contacting the DNA with a polymerase and a population of free nucleotides containing the modified version of dAMP, the modified version of dTMP, dGMP and dCMP. Alternatively, the polymerase may replace dAMP with a modified version of dAMP and replace dGMP with deoxyinosine monophosphate (dIMP). This can be achieved for template DNA by contacting the DNA with a polymerase and a population of free nucleotides containing the modified version of dAMP, dIMP, dGMP and dCMP.

In other preferred embodiments, the polymerase replaces each of the two or more nucleotide species in the template polynucleotide with the same nucleotide. For instance, the polymerase may replace dCMP and dTMP with dPMP (2'-Deoxy-P-nucleoside monophosphate). This can be achieved for template DNA by contacting the DNA with a polymerase and a population of free dPMP, dGMP and dCMP.

It is clear from the discussion above that the modified polynucleotide differs from the reverse complement of the template polynucleotide.

If the template polynucleotide is DNA, the polymerase may replace deoxycytidine monophosphate (dCMP) with deoxymethylcytidine monophosphate. If the template polynucleotide is DNA, the polymerase preferably does not only replace deoxymethylcytidine monophosphate with deoxycytidine monophosphate (dCMP).

If the template polynucleotide is RNA, the polymerase preferably replaces cytidine monophosphate (CMP) with methylcytidine monophosphate.

Different Nucleotide Species

The one or more different nucleotide species are typically chosen to provide the information of interest from the modified polynucleotide. For instance, T k-mers (i.e. k-mers in which the central nucleotide is thymine-based, such as TTA, GTC, GTG and CTA) typically have the lowest current states. Modified versions of T nucleotides may be introduced into the modified polynucleotide to reduce the current states further and thereby increase the total current range seen when the modified polynucleotides moves through the pore.

G k-mers (i.e. k-mers in which the central nucleotide is guanine-based, such as TGA, GGC, TGT and CGA) tend to be strongly influenced by other nucleotides in the k-mer and so modifying the G nucleotides in the modified polynucleotide may help them to have more independent current positions.

Replacing two nucleotide species with the same different nucleotide species may facilitate characterisation because it is then only necessary to map 3-nucleotide k-mers in the modified polynucleotide. However, such modifications do reduce the information provided by the modified polynucleotide and so it is typically necessary to also characterise the template polynucleotide itself (for instance using strand sequencing) to obtain full information about the template polynucleotide.

Replacing one or more nucleotide species with abasic nucleotides results in characteristic current spikes. This allows the clear highlighting of the positions of the one or more nucleotide species in the template polynucleotide.

Replacing all cytosine (C)-based nucleotides in the template polynucleotide with methyl-C (meC)-based nucleotides in the modified polynucleotide allows the building of a GTAmeC model from which the characteristics of meC containing k-mers may be determined. Such characteristics can then be used to distinguish these k-mers from normal C k-mers in the template polynucleotide.

If the template polynucleotide is DNA, the different nucleotide species in the modified polynucleotide preferably comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the template polynucleotide is RNA, the different nucleotide species in the modified polynucleotide preferably comprises a nucleobase which differs from adenine, guanine, uracil, cytosine or methylcytosine and/or comprises a nucleoside which differs from adenosine, guanosine, uridine, cytidine or methylcytidine. The different nucleobase and/or nucleoside is/are capable of complementing one or more of the nucleotides in the template polynucleotide. Commercially available nucleosides include, but are not limited to, 2,6-Diaminopurine-2'-deoxyriboside, 2-Aminopurine-2'-deoxyriboside, 2,6-Diaminopurine-riboside, 2-Aminopurine-riboside, Pseudouridine, Puromycin, 2,6-Diaminopurine-2'-O-methylriboside, 2-Aminopurine-2'-O-methylriboside and Aracytidine. The different nucleotide species may comprise any of these nucleosides.

The different nucleotide species may be a universal nucleotide. A universal nucleotide is one which will hybridise or bind to some degree to all of the nucleotides in the template polynucleotide. A universal nucleotide is preferably one which will hybridise or bind to some degree to nucleotides comprising the nucleosides adenosine (A), thymine (T), uracil (U), guanine (G) and cytosine (C). The universal nucleotide may hybridise or bind more strongly to some nucleotides than to others. For instance, a universal nucleotide (I) comprising the nucleoside, 2'-deoxyinosine, will show a preferential order of pairing of I-C>I-A>I-G approximately=I-T. The polymerase will replace a nucleotide species with a universal nucleotide if the universal nucleotide takes the place of the nucleotide species in the population. For instance, the polymerase will replace dGMP with a universal nucleotide, if it is contacted with a population of free dAMP, dTMP, dCMP and the universal nucleotide.

The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The different nucleotide species preferably comprises a chemical atom or group absent from the nucleotide species it is replacing. The chemical group is preferably a propynyl group, a thio group, an oxo group, a methyl group, a hydroxymethyl group, a formyl group, a carboxy group, a carbonyl group, a benzyl group, a propargyl group or a propargylamine group. The chemical group or atom may be or may comprise a fluorescent molecule, biotin, digoxigenin, DNP (dinitrophenol), a photo-labile group, an alkyne, DBCO, azide, free amino group, a redox dye, a mercury atom or a selenium atom.

Commercially available nucleosides comprising chemical groups which are absent from naturally-occurring nucleosides include, but are not limited to, 6-Thio-2'-deoxyguanosine, 7-Deaza-2'-deoxyadenosine, 7-Deaza-2'-deoxyguanosine, 7-Deaza-2'-deoxyxanthosine, 7-Deaza-8-aza-2'-deoxyadenosine, 8-5'(5'S)-Cyclo-2'-deoxyadenosine, 8-Amino-2'-deoxyadenosine, 8-Amino-2'-deoxyguanosine, 8-Deuterated-2'-deoxyguanosine, 8-Oxo-2'-deoxyadenosine, 8-Oxo-2'-deoxyguanosine, Etheno-2'-deoxyadenosine, N6-Methyl-2'-deoxyadenosine, 06-Methyl-2'-deoxyguanosine, O6-Phenyl-2'deoxyinosine, 2'-Deoxypseudouridine, 2-Thiothymidine, 4-Thio-2'-deoxyuridine, 4-Thiothymidine, 5' Aminothymidine, 5-(1-Pyrenylethynyl)-2'-deoxyuridine, 5-(C2-EDTA)-2'-deoxyuridine, 5-(Carboxy)vinyl-2'-deoxyuridine, 5,6-Dihydro-2'-deoxyuridine, 5.6-Dihydrothymidine, 5-Bromo-2'-deoxycytidine, 5-Bromo-2'-deoxyuridine, 5-Carboxy-2'-deoxycytidine, 5-Fluoro-2'-deoxyuridine, 5-Formyl-2'-deoxycytidine, 5-Hydroxy-2'-deoxycytidine, 5-Hydroxy-2'-deoxyuridine, 5-Hydroxymethyl-2'-deoxycytidine, 5-Hydroxymethyl-2'-deoxyuridine, 5-Iodo-2'-deoxycytidine, 5-Iodo-2'-deoxyuridine, 5-Methyl-2'-deoxycytidine, 5-Methyl-2'-deoxyisocytidine, 5-Propynyl-2'-deoxycytidine, 5-Propynyl-2'-deoxyuridine, 6-O-(TMP)-5-F-2'-deoxyuridine, C4-(1,2,4-Triazol-1-yl)-2'-deoxyuridine, C8-Alkyne-thymidine, dT-Ferrocene, N4-Ethyl-2'-deoxycytidine, 04-Methylthymidine, Pyrrolo-2'-deoxycytidine, Thymidine Glycol, 4-Thiouridine, 5-Methylcytidine, 5-Methyluridine, Pyrrolocytidine, 3-Deaza-5-Aza-2'-O-methylcytidine, 5-Fluoro-2'-O-Methyluridine, 5-Fluoro-4-O-TMP-2'-O-Methyluridine, 5-Methyl-2'-0-Methylcytidine, 5-Methyl-2'-O-Methylthymidine, 2',3'-Dideoxyadenosine, 2',3'-Dideoxycytidine, 2',3'-Dideoxyguanosine, 2',3'-Dideoxythymidine, 3'-Deoxyadenosine, 3'-Deoxycytidine, 3'-Deoxyguanosine, 3'-Deoxythymidine and 5'-O-Methylthymidine. The different nucleotide species may comprise any of these nucleosides. The different nucleotide species is preferably one of those in Table 2. The different nucleotide species is most preferably 2'-fluoro-2'-deoxyadenosine or 5-carboxy-2'-deoxycytidine.

Alternatively, the different nucleotide species preferably lacks a chemical group or atom present in the nucleotide species it is replacing.

The different nucleotide species preferably has an altered electronegativity compared with the one or more nucleotides being replaced. The different nucleotide species having an altered electronegativity preferably comprises a halogen atom. The halogen atom may be attached to any position on the different nucleotide species, such as the nucleobase and/or the sugar. The halogen atom is preferably fluorine (F), chlorine (Cl), bromine (Br) or iodine (I). The halogen atom is most preferably F or I.

Commercially available nucleosides comprising a halogen include, but are not limited to, 8-Bromo-2'-deoxyadenosine, 8-Bromo-2'-deoxyguanosine, 5-Bromouridine, 5-Iodouridine, 5-Bromouridine, 5-Iodouridine, 5'-Iodothymidine and 5-Bromo-2'-O-methyluridine. The different nucleotide species may comprise any of these nucleosides.

Any of the nucleotides mentioned in the Examples may also be used in the method of the invention.

Template RNA

If the template polynucleotide is RNA, the polymerase preferably does not form a complementary polynucleotide, such as complementary DNA. The invention does not concern any of the methods of characterising a method of characterising a target RNA disclosed in International Application No. PCT/GB2014/053121.

Selective Removal of Nucleobases

Step a) of the method preferably further comprises selectively removing the nucleobases from the one or more different nucleotides species in the modified polynucleotide. This results in abasic nucleotides in the modified polynucleotide. An abasic nucleotide is a nucleotide that lacks a nucleobase. The abasic nucleotide typically contains a sugar and at least one phosphate group. The sugar is typically a pentose sugar, such as ribose and deoxyribose. The abasic nucleotide is typically an abasic ribonucleotide or an abasic deoxyribonucleotide. The abasic nucleotide typically contains a monophosphate, diphosphate or triphosphate. Phosphates may be attached on the 5' or 3' side of an abasic nucleotide.

The nucleobases may be selectively removed using any method known in the art. For instance, certain DNA repair proteins, such as human alkyladenine DNA glycosylase (hAAG), are capable of selectively removing 3-methyl adenine, 7-methyl guanine, 1, N6-ethenoadenine and hypoxanthine from nucleotides. Also, dUMP can be selectively removed using uracil DNA glycosylase.

Selective Modification of the One or More Different Nucleotides

Step a) of the method preferably further comprises selectively modifying the one or more different nucleotides species in the modified polynucleotide. Further modification can also be used to produce different k-mers with different current measurements. Further modification may also be used to label the modified polynucleotide or link it to another molecule or surface.

The one or more different nucleotide species may be selectively modified using any of the chemical groups or atoms discussed above. For instance, dPMP may be selectively modified to include a halogen atom.

The one or more different nucleotide species may be selectively modified by glycosylation or pegylation.

Single Stranded Template Polynucleotide

The template polynucleotide may be single stranded. A primer may be annealed to the template polynucleotide and used as a nucleation site for formation of the modified polynucleotide by the polymerase. Once the modified polynucleotide is formed, the template and modified polynucleotides may be linked using a hairpin adaptor. For instance, a hairpin adaptor may be ligated to the two hybridised polynucleotides.

If the template polynucleotide is single stranded, the method preferably further comprises before step a) ligating a hairpin adaptor to one end of the template polynucleotide such that in step a) the ligated hairpin adaptor acts as a primer for formation of the modified polynucleotide by the polymerase such that the modified and template polynucleotides are ligated by the hairpin adaptor.

Suitable hairpin adaptors can be designed using methods known in the art. The hairpin loop may be any length. The hairpin loop is typically 50 or fewer bases, such as 40 or fewer bases, 30 or fewer bases, 20 or fewer bases or 10 or fewer bases, in length. The hairpin loop is preferably from about 1 to 50, from 2 to 40 or from 6 to 30 bases in length. Longer lengths of the hairpin loop, such as from 15 to 50 bases, are preferred if the loop is involved in the differential selectability of the adaptor. Similarly, shorter lengths of the hairpin loop, such as from 1 to 5 bases, are preferred if the loop is not involved in the selectable binding as discussed below.

The hairpin adaptor may be ligated to either end of the template polynucleotide, i.e. the 5' or the 3' end. The hairpin adaptor may be ligated to the template polynucleotide using any method knows in the art. The hairpin adaptor may be ligated using a ligase, such as T4 DNA ligase, *E. coli* DNA ligase, Taq DNA ligase, Tma DNA ligase and 9°N DNA ligase.

The hairpin adaptor preferably comprises a selectable binding moiety. This allows the template polynucleotide and the modified polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a nucleic acid sequence, antibodies, antibody fragments, such as Fab and ScSv, antigens, nucleic acid binding proteins, poly histidine tails and GST tags. The most preferred selective binding moieties are biotin and a selectable nucleic acid sequence. Biotin specifically binds to a surface coated with avidins. Selectable nucleic acid sequences specifically bind (i.e. hybridize) to a surface coated with homologus sequences. Alternatively, selectable nucleic acid sequences specifically bind to a surface coated with nucleic acid binding proteins.

The hairpin adaptor and/or the selectable binding moiety may comprise a region that can be cut, nicked, cleaved or hydrolysed. Such a region can be designed to allow the modified polynucleotide and temple polynucleotide (which may be attached together via the hairpin adaptor) to be removed from the surface to which it is bound following purification or isolation. It can also be designed to allow the modified polynucleotide to be separated from the template polynucleotide. Suitable regions are known in the art. Suitable regions include, but are not limited to, an RNA region, a region comprising desthiobiotin and streptavidin, a disulphide bond and a photocleavable region.

If the template polynucleotide is single stranded, the method preferably further comprises before step a) ligating a first hairpin adaptor to one end of the template polynucleotide such that in step a) the first ligated hairpin adaptor acts as a primer for formation of the modified polynucleotide by the polymerase such that the modified and template polynucleotides are ligated by the first hairpin adaptor and after step (a) but before step (b) ligating a second hairpin adaptor to the end of the template polynucleotide or the modified polynucleotide not ligated to the first hairpin adaptor, contacting the resulting construct with a polymerase and population of free nucleotides under conditions in which the polymerase forms a new polynucleotide using the template polynucleotide and the modified polynucleotide as templates to produce a double stranded construct in which the two strands are linked by the second hairpin adaptor. The population of free nucleotides in this embodiment may be any of the nucleotides discussed above, including the nucleotides in the template polynucleotide, DNA or RNA nucleotides or the different nucleotide species. The double stranded construct may then be characterised in accordance with the invention. The information in the single stranded template polynucleotide is not only doubled by the formation of the modified polynucleotide but also doubled again by the formation of the new polynucleotide.

Double Stranded Template Polynucleotide

The template polynucleotide may be double stranded. A hairpin adaptor which does not link the two strands may be ligated to one end of the double stranded template polynucleotide, i.e. to one end of one of the strands of the double stranded template polynucleotide. The hairpin adaptor may then be used as the nucleation site for primer extension.

If the template polynucleotide is double stranded, the method preferably further comprises before step (a) ligating a first hairpin adaptor to one end of the template polynucleotide and separating the two strands of the template polynucleotide to form a single stranded template polynucleotide construct. The single stranded template polynucleotide construct may then be used as a template to form the modified polynucleotide in accordance with the invention.

Suitable hairpins can be designed as described above. The hairpin loops may be any length as described above. The first hairpin adaptor may be ligated to either end of the template polynucleotide, i.e. the 5' or the 3' end, and the second hairpin adaptor is ligated to the other end. The hairpin adaptors may be ligated to the template polynucleotide as discussed above.

The two strands of the template polynucleotide may be separated using any method known in the art. For instance, they may be separated by a polynucleotide binding protein or using conditions which favour dehybridsation (examples of conditions which favour dehybridisation include, but are not limited to, high temperature, high pH and the addition of agents that can disrupt hydrogen bonding or base pairing, such as formamide and urea). The polymerase preferably simultaneously separates the two strands of the template polynucleotide and uses the strands as templates to form the modified polynucleotide.

The method preferably further comprises before step a) ligating a second hairpin adaptor to one end of the single stranded template polynucleotide construct such that in step (a) the ligated hairpin adaptor acts as a primer for formation of the modified polynucleotide by the polymerase such that the modified polynucleotide and the single stranded polynucleotide construct are ligated by the second hairpin adaptor.

The second hairpin may be any of the hairpins discussed above.

The second hairpin adaptor further comprises a region at which the hairpin can be cut, nicked, cleaved or hydrolysed and the method further comprises before step (c) cutting the second hairpin adaptor to open the circular polynucleotide construct and produce a double stranded polynucleotide. Suitable regions are discussed above.

The first or second hairpin adaptor preferably comprises a selectable binding moiety as discussed above.

Leader Sequence

Before step b), the method preferably comprises attaching to the modified polynucleotide a leader sequence which preferentially threads into the pore. The leader sequence facilitates the method of the invention. The leader sequence is designed to preferentially thread into the transmembrane pore and thereby facilitate the movement of target polynucleotide through the pore. The leader sequence typically comprises a polymer. The polymer is preferably negatively charged. The polymer is preferably a polynucleotide, such as DNA or RNA, a modified polynucleotide (such as abasic DNA), PNA, LNA, BNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises one or more spacers.

The leader sequence can be any length, but is typically 10 to 150 nucleotides in length, such as from 20 to 150 nucleotides in length. The length of the leader typically depends on the transmembrane pore used in the method.

Characterisation

Step b) comprises contacting the modified polynucleotide with a transmembrane pore such that the modified polynucleotide moves through the pore. The modified polynucleotide and the template polynucleotide may be contacted with a transmembrane pore such they both move through the pore.

Steps b) and c) of the method are preferably carried out with a potential applied across the pore. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5. In some instances, the current passing through the pore as the polynucleotide moves with respect to the pore is used to determine the sequence of the modified polynucleotide. This is strand sequencing. If the modified polynucleotide is sequenced, the sequence of the template polynucleotide may then be reconstructed.

The whole or only part of the modified polynucleotide and/or template polynucleotide may be characterized, for instance sequenced, using this method. The length of the template polynucleotide is discussed above. The modified polynucleotide(s) will be substantially the same length.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The modified polynucleotide and/or template polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the pore. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the pore. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

Suitable methods of coupling are disclosed in International Application No. PCT/GB12/05119 1 (published as WO 2012/164270) and UK Application No. 1406155.0.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane R barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin (the sequence of one monomer or subunit of α-hemolysin-NN is shown in SEQ ID NO: 4), anthrax toxin and leukocidins, and outer membrane proteins/porins of bacteria, such as *Mycobacterium smegmatis* porin (Msp), for example MspA MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215: 403-10. Software for performing BLAST analyses is publicly available through the National Center for Biotechnology Information (ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. Any of the proteins described herein, such as the transmembrane protein pores, may be made synthetically or by recombinant means. For example, the pore may be synthesized by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

The pore may also be produced using D-amino acids. For instance, the pore or construct may comprise a mixture of L-amino acids and D-amino acids. This is conventional in the art for producing such proteins or peptides.

The method of the invention involves measuring one or more characteristics of the modified polynucleotide(s) or template polynucleotide. The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19): 7702-7, Lieberman K R et al, J Am Chem Soc. 2010; 132(50): 17961-72, and International Application WO-2000/28312. Alternatively, electrical measurements may be made using a multi-channel system, for example as described in International Application WO-2009/077734 and International Application WO-2011/067559.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Step b) preferably further comprises contacting the modified polynucleotide with a polynucleotide binding protein such that the protein controls the movement of the modified polynucleotide through the pore. More preferably, the method comprises (a) contacting the modified polynucleotide with a transmembrane pore and a polynucleotide binding protein such that the polynucleotide moves through the pore and the protein controls the movement of the polynucleotide through the pore and (b) measuring the current passing through the pore as the polynucleotide moves with respect to the pore wherein the current is indicative of one or more characteristics of the polynucleotide and thereby characterising the modified polynucleotide.

In some instances, both the template and modified polynucleotides move through the pore, such as when they are ligated to one another. Step b) preferably further comprises contacting the modified polynucleotide and the template polynucleotide with a polynucleotide binding protein such that the protein controls the movement of both polynucleotides through the pore. More preferably, the method comprises (a) contacting the modified polynucleotide and the template polynucleotide with a transmembrane pore and a polynucleotide binding protein such that both polynucleotides move through the pore and the protein controls the movement of the polynucleotides through the pore and (b) measuring the current passing through the pore as the polynucleotides move with respect to the pore wherein the current is indicative of one or more characteristics of the polynucleotides and thereby characterising the template polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17) and variants thereof. Three subunits comprising the sequence shown in SEQ ID NO: 15 or a variant thereof interact to form a trimer exonuclease. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Mhu (SEQ ID NO: 20), TraI Eco (SEQ ID NO: 21), XPD Mbu (SEQ ID NO: 22) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925; PCT/GB2013/051924, PCT/GB2013/051928 and PCT/GB2014/052736.

The helicase preferably comprises the sequence shown in SEQ ID NO: 25 (Trwc Cba) or as variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 8 comprises E94C/A360C and then (ΔM1)G1G2 (i.e. deletion of M1 and then addition G1 and G2).

Any number of helicases may be moved past the one or more spacers in accordance with the invention. For instance, 1, 2, 3, 4, 5, 6, 7, 8, 9, 10 or more helicases may be moved past the one or more spacers. In some embodiments, different numbers of helicases may be moved past each spacer. For instance, if two helicases are stalled using two separate spacers, one helicase (the first helicase) may be moved past the first spacer, but two helicases (the first and second helicases) may be moved past the second spacer.

The method of the invention preferably comprises moving two or more, such as three or more or four or more, stalled helicases past one or more spacers. The two or more helicases are typically the same helicases. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925; PCT/GB2013/051924; PCT/GB2013/051928; and PCT/GB2014/052736.

A variant of SEQ ID NOs: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature.

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

The method of characterising a modified or a template polynucleotide preferably involves contacting the polynucleotide with a pore and a polynucleotide binding protein derived from a helicase. Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the bilayer. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the bilayer.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Steps b) and c) of the method are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Helicase(s) and Molecular Brake(s)

In a preferred embodiment, the method comprises:

(i) providing the/each polynucleotide with one or more helicases and one or more molecular brakes attached to the/each polynucleotide;

(b) contacting the/each polynucleotide with a transmembrane pore and applying a potential across the pore such that the one or more helicases and the one or more molecular brakes are brought together and both control the movement of at least one strand of the/each polynucleotide through the pore;

(c) taking one or more measurements as the/each polynucleotide moves with respect to the pore wherein the measurements are indicative of one or more characteristics of the polynucleotide and thereby characterising the modified or template polynucleotide.

This type of method is discussed in detail in the International Application No. PCT/GB2014/052737.

Kits

The present invention also provides a kit for characterising a template polynucleotide. The kit comprises (a) a polymerase and (b) a population of free nucleotides comprising a nucleotide species which differs from one or more of the nucleotide species in the template polynucleotide. The polymerase is capable of forming a modified polynucleotide from the free nucleotides using the template polynucleotide as a template. The polymerase is capable of replacing one or more of the nucleotide species in the template polynucleotide with the different nucleotide species.

The kit preferably further comprises a hairpin loop and/or a leader sequence which is capable of preferentially threading into a transmembrane pore. The kit preferably further comprises a transmembrane pore. The kit preferably further comprises a polynucleotide binding protein.

Any of the embodiments discussed above with reference to the method of the invention equally apply to the kits. The kit may further comprise the components of a membrane, such as the components of an amphiphilic layer or a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

Homopolynucleotide Method

The invention also provides a method of characterising a homopolynucleotide. A homopolynucleotide is a polynucleotide composed of only one nucleotide species. The homopolynucleotide may comprise any of the nucleotide species discussed above. Homopolynucleotides include, but are not limited, to poly(A), poly(dA), poly(U), poly(dU), poly(C), poly(dC), poly(G), poly(dG), poly(T) and poly (dT). Homopolynucleotides are difficult to characterise using a pore, such as in strand sequencing, because the presence of a single nucleotide species results in a constant current signal as the homopolynucleotide passes through the pore. The method of the invention avoids this issue as discussed below, The homopolynucleotide may be any length. The homopolynucleotide may be from 2 to 100 nucleotides in length, such as from 5 to 50 or from 10 to 40 nucleotides in length. The homopolynucleotide may form part of a longer template polynucleotide.

The homopolynucleotide is contacted with a population of free nucleotides. The polymerase uses the free nucleotides to form the modified polynucleotide based on the homopolynucleotide. The identities of the free nucleotides in the population determine the composition of the modified polynucleotide.

Each free nucleotide in the population is capable of hybridising or binding to the nucleotide species in the homopolynucleotide. Each free nucleotide in the population is typically capable of specifically hybridising or specifically binding to (i.e. complementing) the nucleotide species in the template polynucleotide. This allows the polymerase to use complementarity (i.e. base pairing) to form the modified polynucleotide using the homopolynucleotide.

Each free nucleotide is capable of being handled by the polymerase and incorporated into the modified polynucleotide.

The modified polynucleotide is not the reverse complement of the homopolynucleotide. The polymerase when forming the modified polynucleotide randomly replaces some of the instances of the nucleotide species that is complementary to the nucleotide species in the homopolynucleotide with a different nucleotide species. For instance, the polymerase may replace some instances of dTMP with a modified version of dTMP in the modified polynucleotide when using a poly(dAMP) homopolynucleotide as a template.

The random replacement of some instances of the nucleotide species results in a modified polynucleotide which provides a variable current signal as it passes though the pore. This allows the homopolynucleotide to be more easily characterised.

The different nucleotide species is preferably a modified version of the nucleotide species being replaced. It may be modified in any of the way discussed above.

The method of the invention is illustrated below.

```
Homo      ...AAAAAAAAA...

Modified ...XTTXXTTTX...
```

In the illustration above, both strands are based on DNA. The homopolynucleotide is shown on the top and is poly (dAMP). The modified nucleotide is shown on the bottom. The polymerase has randomly replaced some of the nucleotide species T (i.e. dTMP) with a different nucleotide species X in the modified polynucleotide. The different nucleotide species X may be any of those discussed above. X is preferably a modified version of T. It may be modified in any of the ways discussed above. In order to do this, the template polynucleotide is contacted with a polymerase and a population of T and X. The polymerase is capable of handling X and randomly inserting X at positions where T should appear in the modified polynucleotide.

Any number of instances of the nucleotide species may be replaced with a different nucleotide species. For instance, the polymerase may replace at least 5%, at least 10%, at least 20%, at least 30%, at least 40%, at least 50%, at least 60%, at least 70% or at least 80% of the nucleotide species with a different nucleotide species. The polymerase typically does not replace all of the nucleotide species with a different nucleotide species. The number of instances of the nucleotide species replaced with a different nucleotide species is typically dependent on the relative strengths of hybridisation or binding to the homopolynucleotide of the different nucleotide species and the nucleotide species being replaced and/or the ratio of the different nucleotide species and the nucleotide species being replaced in the population of free nucleotides.

In some preferred embodiments, the polymerase when forming the modified polynucleotide randomly replaces some of the instances of the nucleotide species that is complementary to the nucleotide species in the homopolynucleotide with a first different nucleotide species and randomly replaces other instances of the nucleotide species that is complementary to the nucleotide species in the homopolynucleotide with a second different nucleotide species. In other words, different instances of the nucleotide species are replaced with distinct nucleotide. For instance, the polymerase may replace some instances of dTMP with a modified version of dTMP, such as dTMP lacking a native chemical group, and replace other instances of dTMP with different modified version of dTMP, such as dTMP modified with a halogen atom. This can be achieved for template DNA by contacting the DNA with a polymerase and a population of free nucleotides containing dTMP, the modified version of dTMP and the different modified version of dTMP. Some instances of the nucleotide species may not be replaced.

This embodiment is illustrated below.

```
Homo      ...AAAAAAAAA...

Modified ...XTXYXTYTX...
```

In the illustration above, both strands are based on DNA. The homopolynucleotide is shown on the top and is poly (dAMP). The modified nucleotide is shown on the bottom. The polymerase has randomly replaced some of the nucleotide species T (i.e. dTMP) with two different nucleotide species X and Y in the modified polynucleotide. The different nucleotide species X and Y may be any of those discussed above. X and Y are preferably different modified versions of T. They may be modified in any of the ways discussed above. In order to do this, the template polynucleotide is contacted with a polymerase and a population of T, X and Y. The polymerase is capable of handling X and Y and inserting them at positions where T should appear in the modified polynucleotide. The relative number of T, X and Y in the modified polynucleotide is typically dependent on the relative strengths of hybridisation or binding of T, X and Y to the homopolynucleotide and/or the ratio of T, X and Y in the population of free nucleotides.

Alternatively, all instances of the nucleotide species in template polynucleotide may be replaced, either with the first different nucleotide species or the second nucleotide species. This embodiment is illustrated below using the same key as above.

```
Homo      ...AAAAAAAAA...

Modified ...XYXYXYYXX...
```

In order to do this, the template polynucleotide is contacted with a polymerase and a population of X and Y. The relative number of X and Y in the modified polynucleotide is typically dependent on the relative strengths of hybridisation or binding of X and Y to the homopolynucleotide and/or the ratio of X and Y in the population of free nucleotides.

The modified polynucleotide formed using the homopolynucleotide as a template then is contacted with a transmembrane pore such that the modified polynucleotide moves through the pore. One or more measurements are then taken as the modified polynucleotide moves with respect to the pore wherein the measurements are indicative of one or more characteristics of the modified polynucleotide and thereby characterising the homopolynucleotide. Any of the embodiments discussed above are applicable to these steps.

The following Examples illustrate the invention.

EXAMPLES

Example 1

This example describes how 600 bp strands of DNA were made by filling in ssDNA from a 5' leader and tether site and a 3' hairpin, using Klenow (SEQ ID NO: 26) and dNTPs (when at least one of the dNTPs was a different nucleotide species from dAMP, dGMP, dTMP and dCMP).

Materials and Methods

1.1 Preparation of ssDNA Sample

The 600 bp ssDNA fragment of Lambda DNA sample (SEQ ID NO: 33 which is attached at the 5' end to four iSpC3 spacers which are attached at the opposite end to SEQ ID NO: 30) needed for step 1.2 was produced using the following method. A 600 bp fragment of lambda (SEQ ID NO: 27 shows the sense sequence of dsDNA) was amplified using LongAmp™ Taq DNA polymerase (NEB, catalog No: M0323S) with the following primers SEQ ID NO: 28 and SEQ ID NO: 29. Reactions were cycled as follows; 94° C. for 30 secs, (94° C. for 15secs, 57° C. for 30 secs, 65° C. for 1 min)30, 65° C. 5 mins. The 600 bp fragment was run on a 5% TBE PAGE gel and PAGE purified, eluting in nuclease free water.

A second round of PCR was then carried out using the first round product as template, LongAmp™ Taq DNA polymerase (NEB, catalog No: M0323S) and the following primers (primer 1=SEQ ID NO: 30 is attached at its 5 end to 28 iSpC3 spacers which are attached at the opposite end to two thymines and at its 3' end to four iSpC3 spacers which are attached at the opposite end to SEQ ID NO: 31 and primer 2=SEQ ID NO: 32).

After PCR the product was then subjected to lambda exonuclease (NEB, catalog No. M0262S) digestion for 1 hour at 37° C. After digestion the product was run on a 5% TBE PAGE gel and the ssDNA purified from the gel (SEQ ID NO: 33 which is attached at the 5' end to four iSpC3 spacers which are attached at the opposite end to SEQ ID NO: 30), eluting in nuclease free water.

1.2 Preparation of Modified DNA Sample

The modified ssDNA sample was made via the following method outlined in the Table 1 and the paragraphs below. The example in the table substituted dGTP with 6-thio-2'-deoxyguanosine-5'-triphosphate, however, any of the dNTP's can be substituted for a different nucleotide species using the below procedure.

TABLE 1

| Component | Volume | Final Concentration |
|---|---|---|
| 600 bp ssDNA fragment of Lambda DNA (SEQ ID NO: 33 which is attached at the 5' end to four iSpC3 spacers which are attached at the opposite end to SEQ ID NO: 30), 500 nM | 20 μL | 100 ml |
| NEBuffer2 (10 x) | 10 μL | N/A |
| DTT (100 mMD) | 1 μL | 1 mM |
| dCTP, dTTP, dATP | 2 μL | 200 μM |
| 6-thio-2'-deoxyguanosine-5'-triphosphate | 2 μL | 200 μM |
| Klenow exo^ (SEQ ID NO: 26) | 2.5 μL | 25 U |
| $nH_2O$ | 62.5 μL | N/A |

The above reaction mixture was incubated at 37° C. for 60 minutes. A 15 μL sample was added to $RecJ_f$ (purchased from New England Biolabs™) and incubated for 1 hour at 37° C. before it was run on a 5% TBE PAGE at 140 V for 55 minutes. An example of a PAGE gel is shown in FIG. 1. Lane 5 shows a gel of the modified DNA where dTTP had been replaced with 5-propynyl-2'-deoxyuridine-5'-triphosphate in the sample preparation procedure described previously in table 1. Lane 6 shows a gel of the modified DNA where dGTP had been replaced with 6-thio-2'-deoxyguanosine-5'-triphosphate in the sample preparation procedure described in table 1. Lane 7 shows a gel of the modified DNA where dTTP and dGTP were replaced with 5-propynyl-2'-deoxyuridine-5'-triphosphate and 6-thio-2'-deoxyguanosine-5'-triphosphate respectively in the sample preparation procedure described previously in table 1. The band produced by the modified 600 bp fragment ran at the same position as the 600 bp control (lane 3), illustrating that the sample preparation had been successful.

The reaction mixture was then purified using SPRI beads (150 μL) and eluted in nuclease free water (40 μL). The sample was quantified using the Nanodrop and the concentration adjusted to 100 nM. The DNA sample (SEQ ID NO: 34 which is attached at the 3' end to four iSpC3 spacers which are attached at the opposite end to the 5' end of SEQ ID NO: 38 shows the non-modified sequence, where in this example all G's are substituted for 6-thio-2'-deoxyguanosine-5'-triphosphate) (100 nM) was then incubated with tether (SEQ ID NO: 42, 100 nM.), 5× annealing buffer and nuclease free water and heated at 55° C. for 2 minutes and the cooled to 18° C. at 2° C. per minute.

Example 2

This example describes how a Trwc Cba (SEQ ID NO: 25) enzyme controlled the movement of modified polynucleotides through a single MspA nanopore (MS(B1-G75S/G77S/L88N/Q126R)8 MspA (MspA-B2C) (SEQ ID NO: 2 with mutations G75S/G77S/L88N/Q126R).

Materials and Methods

Prior to setting up the experiment, the modified DNA construct (SEQ ID NO: 34 which is attached at the 3' end to four iSpC3 spacers which are attached at the opposite end to the 5' end of SEQ ID NO: 38 where at least one of C, T, A or G was replaced with a different nucleotide triphosphate species in step 1.2 of Example 1; also including tether sequence SEQ ID NO: 42, final concentration 0.5 nM) and TrwC Cba (1 μM) were pre-incubated together for at least an hour at 23° C. in buffer (50 mM CAPS/NaOH, pH 10.0+100 mM NaCl).

Electrical measurements were acquired at 15° C. (by placing the experimental system on a cooler plate) from single MspA nanopores (MspA-B2C) inserted in block co-polymer in buffer (625 mM KCl, 100 mM HEPES, 75 mM Potassium Ferrocyanide (II), 25 mM Potassium ferricyanide (III), pH 8). After achieving a single pore inserted in the block co-polymer, then buffer (1 mL, 625 mM KCl, 100 mM HEPES, 75 mM Potassium Ferrocyanide (II), 25 mM Potassium ferricyanide (III), pH 8) was flowed through the system to remove any excess MspA nanopores (MspA-B2C). $MgCl_2$ (10 mM final concentration) and dTTP (5 mM final concentration) were mixed together with buffer (625 mM KCl, 100 mM HEPES, 75 mM Potassium Ferrocyanide (II), 25 mM Potassium ferricyanide (III), pH 8) and then added to the modified DNA construct (0.5 nM final concentration), TrwC Cba (1 µM final concentration) buffer (50 mM CAPS/NaOH, pH 10.0+100 mM NaCl) pre-mix. The pre-mix was then added to the single nanopore experimental system. Experiments were carried out for two hours following a potential flip process (120 mV with potential flips down of −100 mV for 2 seconds then 0 mV for 2 seconds every 20 minutes) and helicase-controlled DNA movement was monitored.

Results and Discussion

Helicase controlled DNA movement was observed for the modified DNA constructs tested (labelled construct Z in table 2 below, which corresponds to SEQ ID NO: 34 which is attached at the 3' end to four iSpC3 spacers which are attached at the opposite end to the 5' end of SEQ ID NO: 38 where at least one of C, T, A or G was replaced with a different nucleotide tri-phosphate species in step 1.2 of Example 1; also including tether sequence SEQ ID NO: 42). A list of other tested modified polynucleotides which were investigated is provided at the end of this example (for example entries 2-4 the buffer used was 600 mM KCl, 25 mM potassium phosphate, 75 mM potassium ferrocyanide (II), 25 mM potassium ferricyanide, pH 8.0 and the potential flip protocol used was 120 mV with potential flips down of −100 mV for 2 seconds then 0 mV for 2 seconds every 10 minutes). Table 2 below highlights a number of examples which were investigated.

TABLE 2

| Experiment No. | Base replaced in step 1.2 in construct Z | Modified Nucleotide tri-phosphate Species used in step 1.2 | Chemical Structure | FIG. No. |
|---|---|---|---|---|
| 1 | T | 5-propynyl-2'-deoxyuridine-5'-triphosphate | 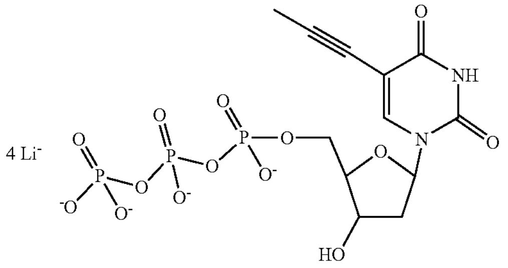 | 2 and 3 |
| 2 | A | 2'-fluoro-2'-deoxyadenosine-5'-triphosphate | 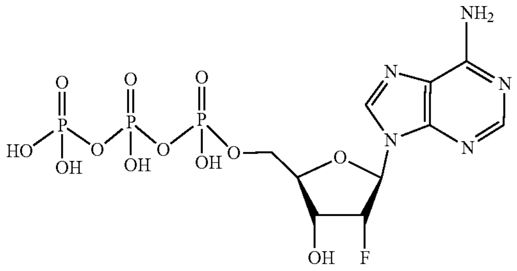 | 4 |
| 3 | A | 2-fluoro-adenosine-5'triphosphate | 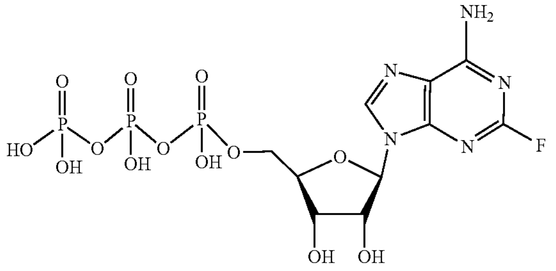 | 5 |

TABLE 2-continued

| Experiment No. | Base replaced in step 1.2 in construct Z | Modified Nucleotide tri-phosphate Species used in step 1.2 | Chemical Structure | FIG. No. |
|---|---|---|---|---|
| 4 | G | 7-deaza-7-iodo-2'-deoxy-guanosme-5'triphosphate | 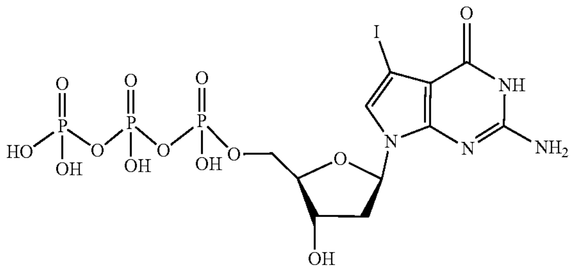 | 6 |
| 5 | G | 2'-fluoro-2' deoxyguanosine-5'-triphosphate | 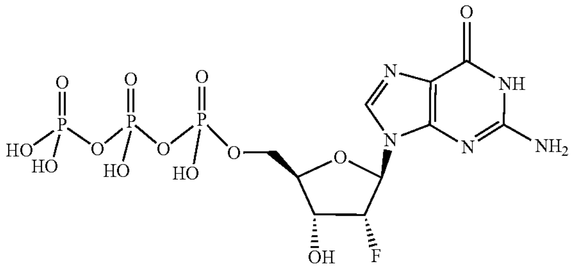 [SMILES: Nc1nc2c(ncn2[C@@H]2O[C@H](COP(=O)(O)OP(=O)(O)OP(=O)(O)O)[C@@H](O)[C@H]2F)c(=O)[nH]1] | 7 |
| 6 | C | 5-formyl-2' deoxycytidine-5'-triphosphate | 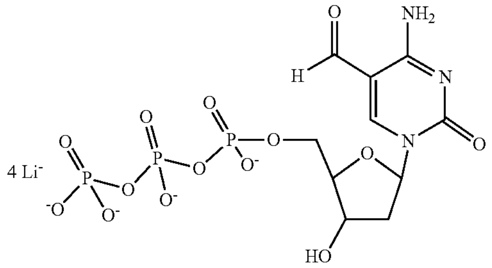 | 8 |

Figure 3:
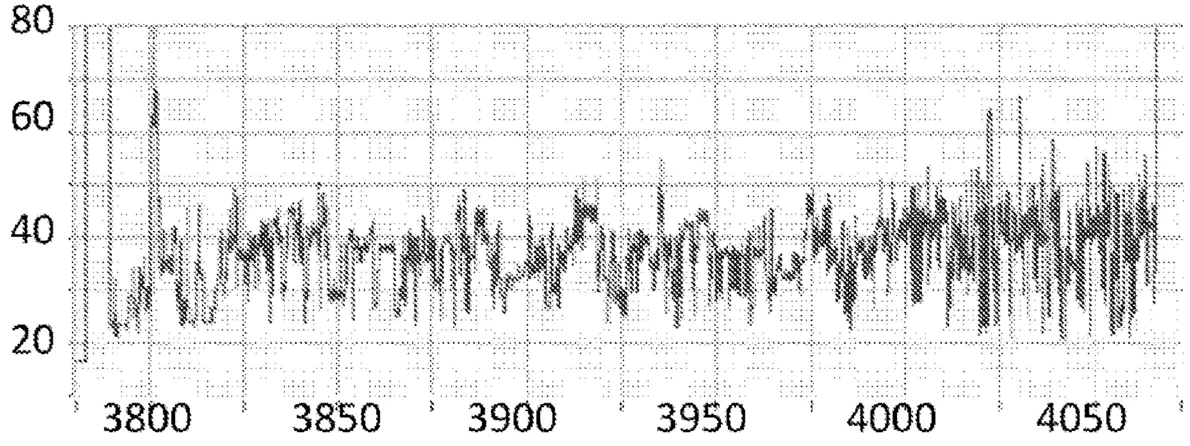
FIG. 3 shows an example current trace (y-axis label=Current (pA), x-axis label=Time (s)) of when a helicase (TrwC Cba (SEQ ID NO: 25) controlled the translocation of the modified DNA construct (SEQ ID NO: 34 which is attached at the 3' end to four iSpC3 spacers which are attached at the opposite end to the 5' end of SEQ ID NO: 38 where T was replaced with 5-propynyl-2'-deoxyuridine-5'-triphosphate in step 1.2 of Example 1; also including tether sequence SEQ ID NO: 42, 0.5 nM) through a nanopore (MS(B1-G75S/G77S/L88N/Q126R)8 MspA (MspA-B2C) (SEQ ID NO: 2 with mutations G75S/G77S/L88N/Q126R)). The lower current trace is a zoomed in region of the trace above.
Figure 3:
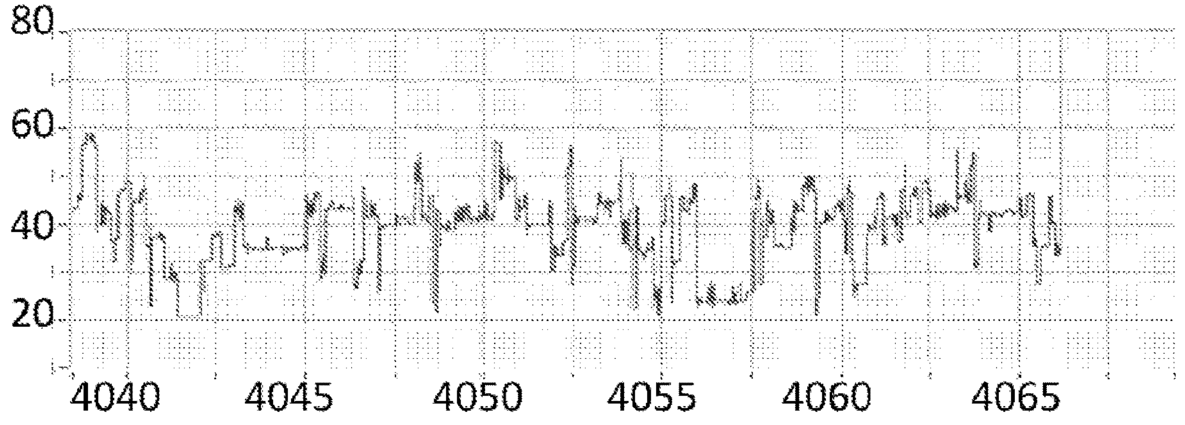
Figure 4:
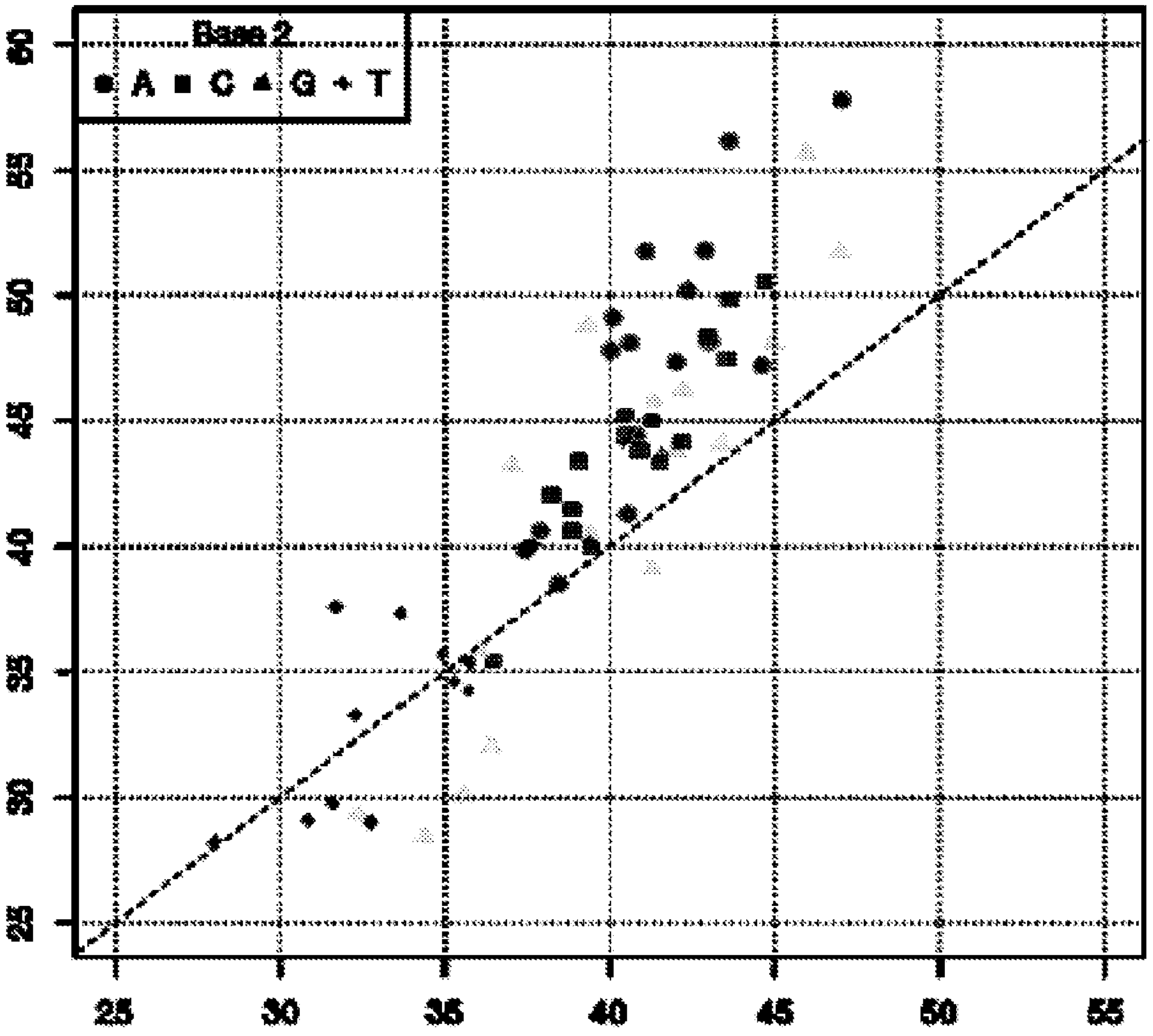
FIG. 4 shows a diagonal dot plot for the modified DNA construct which was made up of C, T, G and 2'-fluoro-2'-deoxyadenosine-5'-triphosphate. The diagonal dot plot displays the current level for each base combination in the modified strand plotted against its equivalent in an unmodified strand, such that the large changes in the current-sequence relationship are represented by large displacements from the diagonal.
Figure 5:
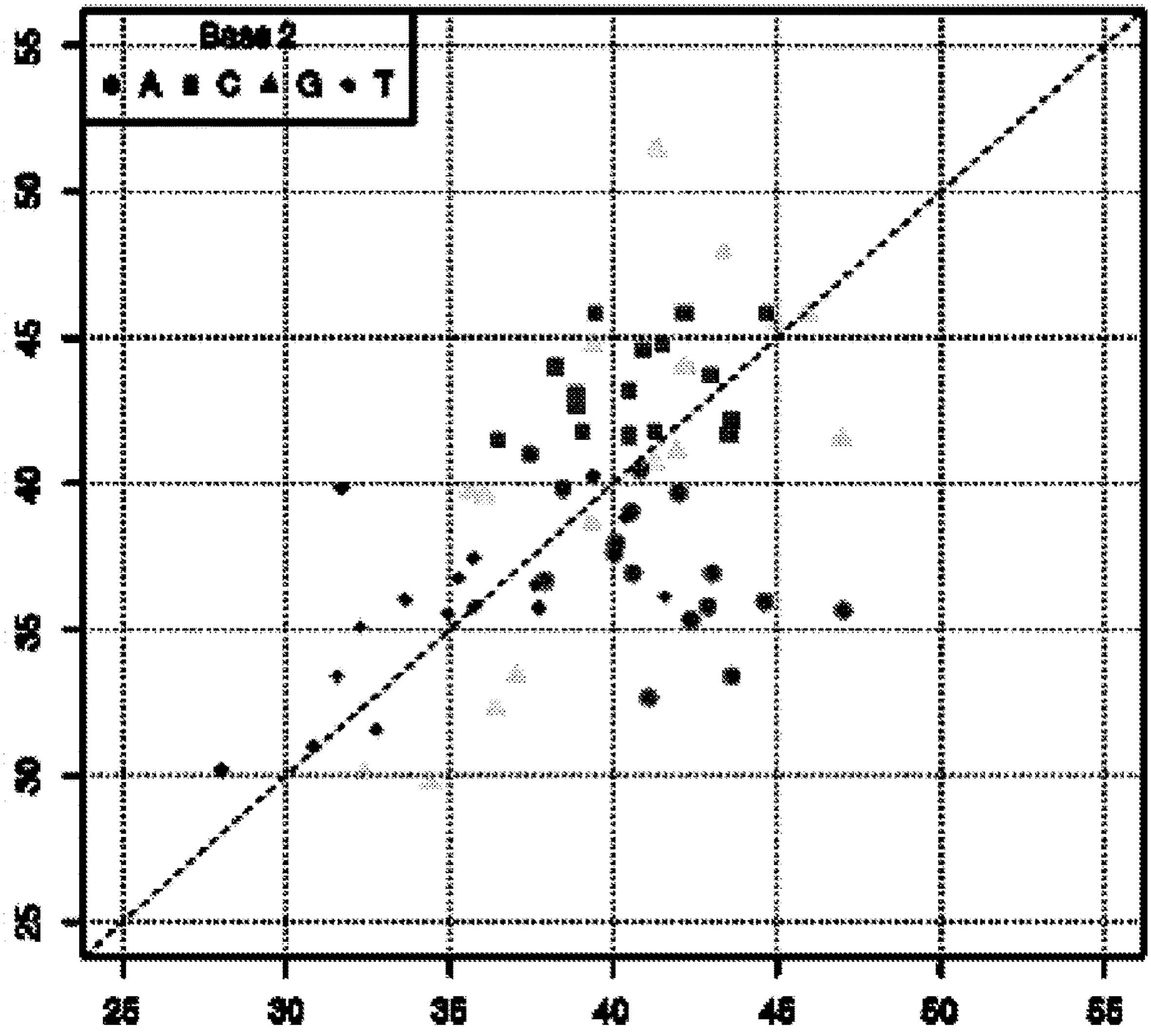
FIG. 5 shows a diagonal dot plot for the modified DNA construct which was made up of C, T, G and 2-fluoro-adenosine-5'triphosphate. The diagonal dot plot displays the current level for each base combination in the modified strand plotted against its equivalent in an unmodified strand, such that the large changes in the current-sequence relationship are represented by large displacements from the diagonal.
Figure 6:
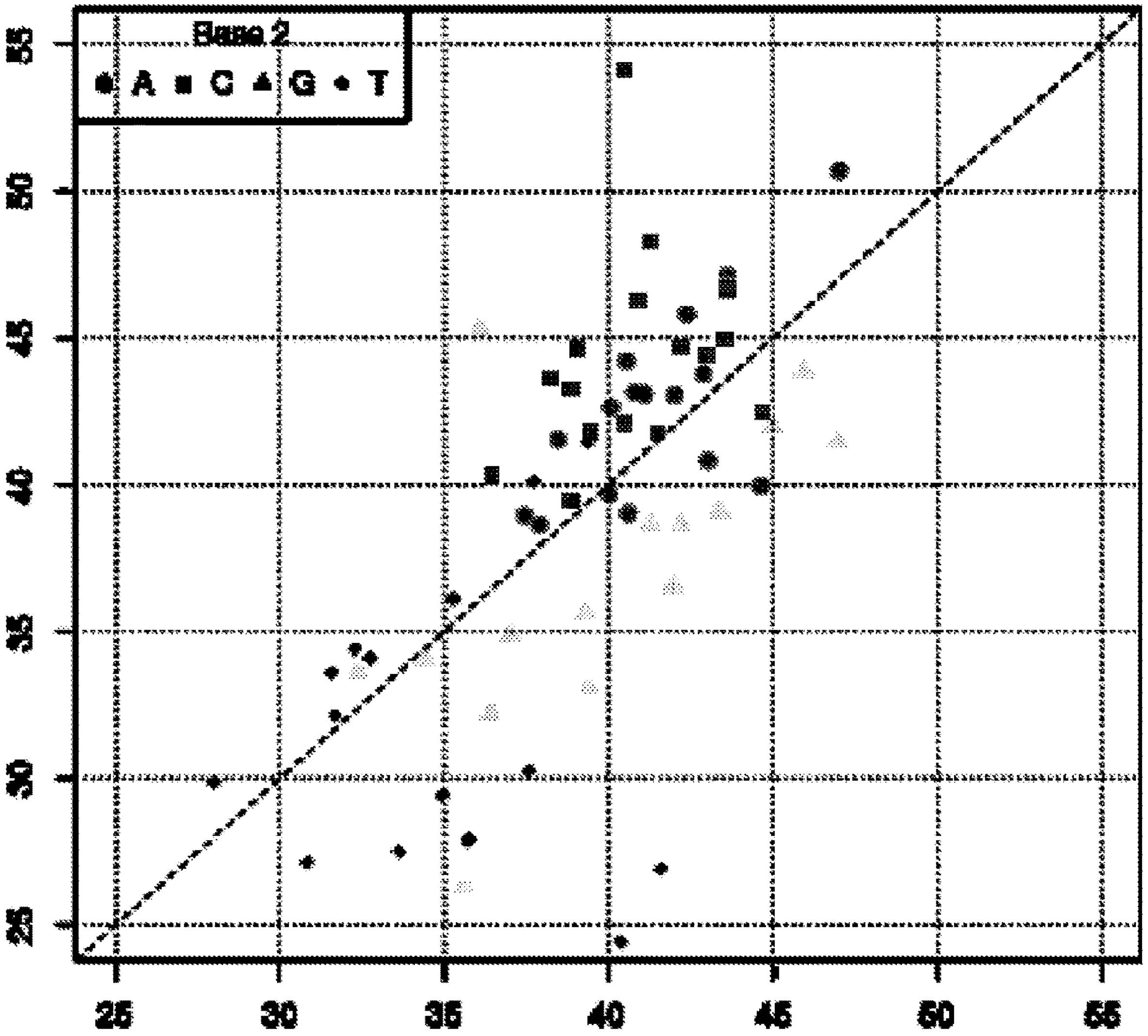
FIG. 6 shows a diagonal dot plot for the modified DNA construct which was made up of C, T, A and 7-deaza-7-iodo-2'-deoxy-guanosine-5'triphosphate. The diagonal dot plot displays the current level for each base combination in the modified strand plotted against its equivalent in an unmodified strand, such that the large changes in the current-sequence relationship are represented by large displacements from the diagonal.
Figure 7:
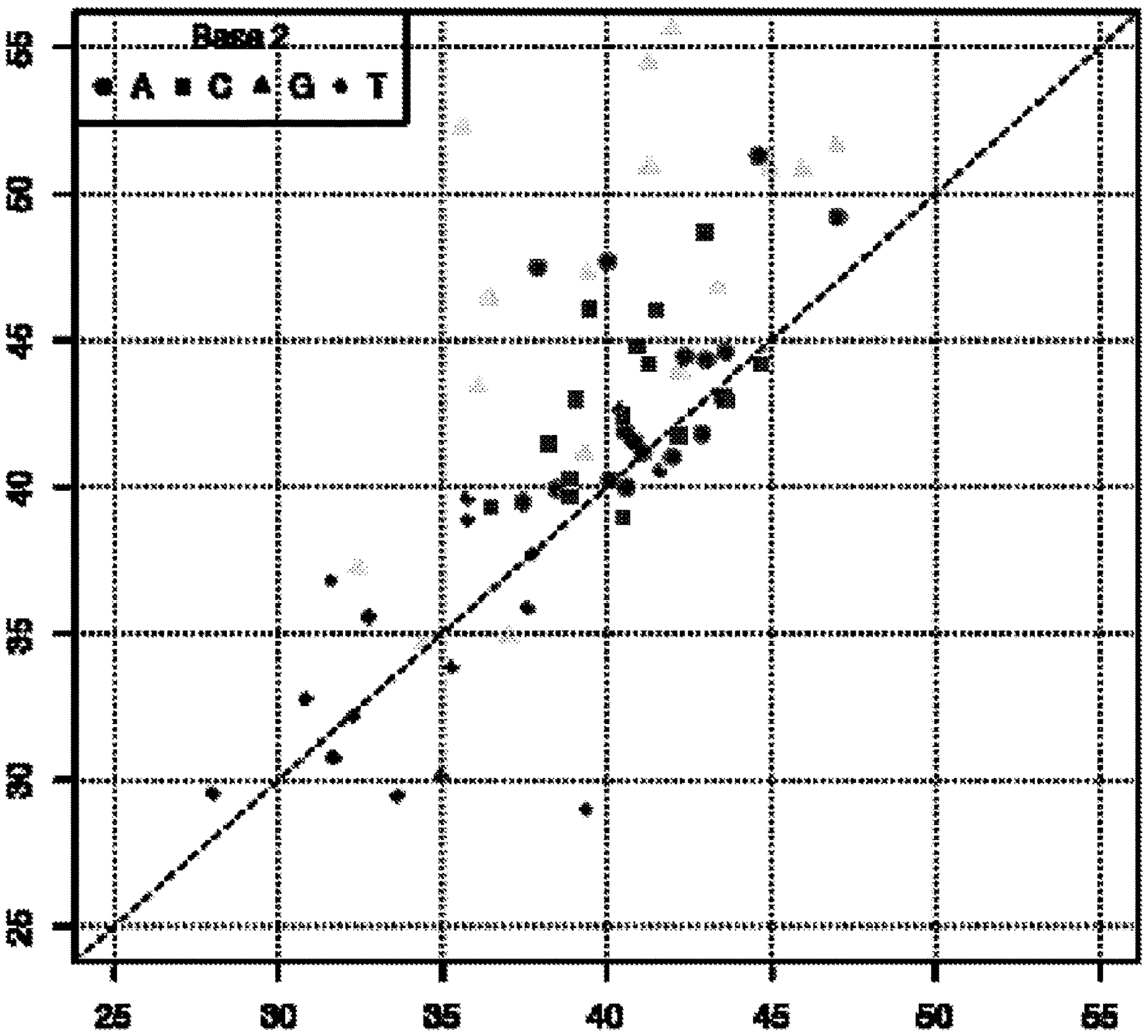
FIG. 7 shows a diagonal dot plot for the modified DNA construct which was made up of C, T, A and 2'-fluoro-2'deoxyguanosine-5'-triphosphate. The diagonal dot plot displays the current level for each base combination in the modified strand plotted against its equivalent in an unmodified strand, such that the large changes in the current-sequence relationship are represented by large displacements from the diagonal.
Figure 8:
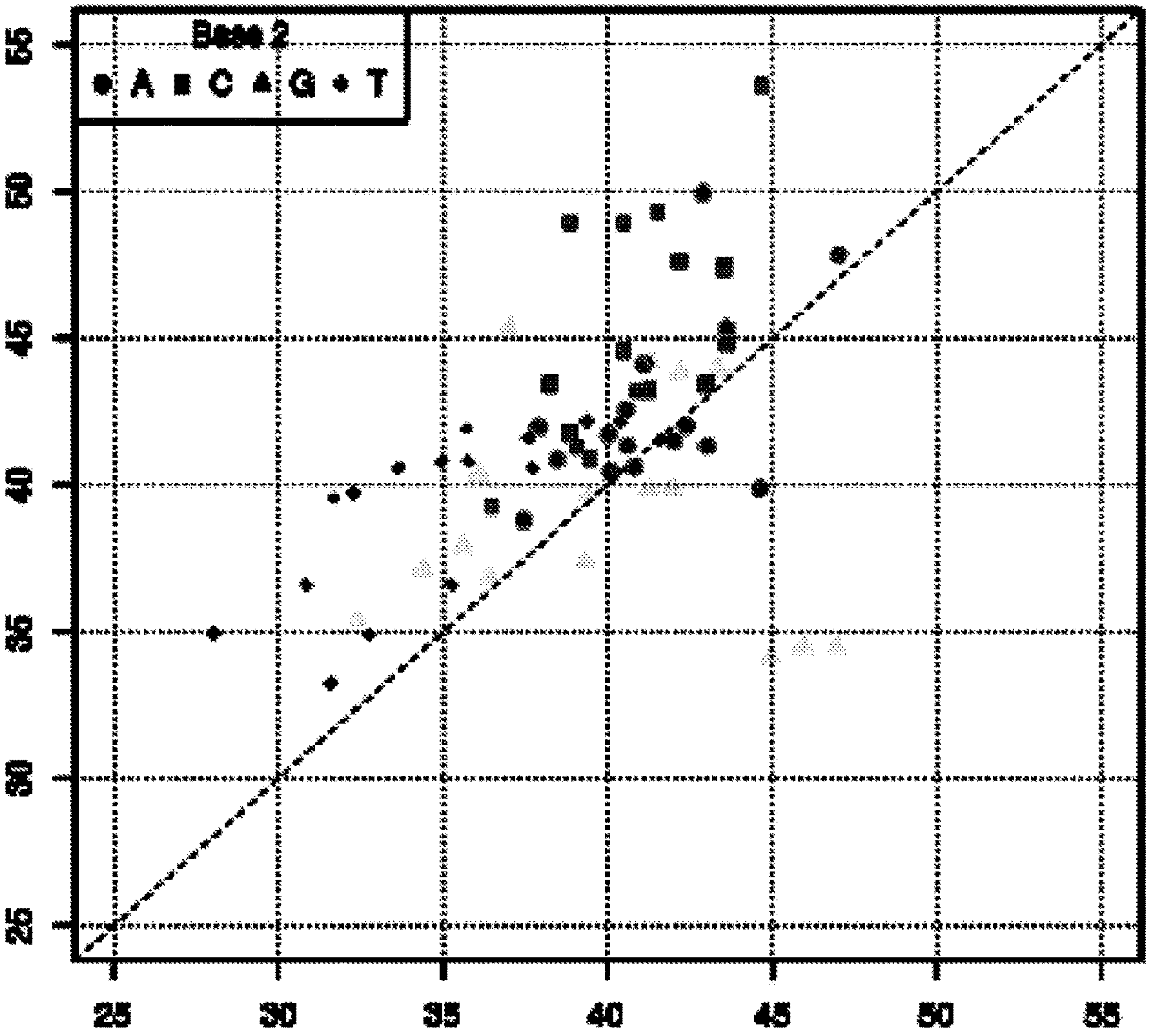
FIG. 8 shows a diagonal dot plot for the modified DNA construct which was made up of G, T, A and 5-formyl-2'deoxycytidine-5'-triphosphate. The diagonal dot plot displays the current level for each base combination in the modified strand plotted against its equivalent in an unmodified strand, such that the large changes in the current-sequence relationship are represented by large displacements from the diagonal.

The diagonal dot plots shown in FIGS. 2 and 4-8 display the current level for each base combination in the modified strand plotted against its equivalent in an unmodified strand, such that large changes in the current-sequence relationship were represented by large displacements from the diagonal. FIG. 3 shows an example of helicase controlled DNA movement for experiment number 1 in table 2.

When data from a modified template was obtained, the strands were mapped to the known sequence and used to train a new base-calling model where each "kmer" or base combination had a characteristic current level. These kmer current levels were plotted on the vertical axis, against their unmodified equivalents on the horizontal axis. The shape of the point denoted the central base of the combination. In this way the relationship between measured current signal and sequence for a particular set of modifications was described. A modified template which showed a very different current-sequence relationship showed points which moved away from the diagonal, whereas one with little change showed points arranged close to the diagonal. Depending on the specific modification(s) used, the changes observed were either due to specific sets of kmers, or a more general spread.

Modifications which demonstrated large or distinct changes from the standard model were of especial interest as they were used in combination with the standard to provide more information about the sequence. It was clear from exemplary FIGS. 2 and 4-8 that the introduction of different nucleotides species into the modified polynucleotide produced distinct changes in the standard model.

The following different nucleotide species were also tested in the same experimental system described above—5-Carboxy-2'-deoxycytidine-5'-Triphosphate, 5-Propynyl-2'-deoxycytidine-5'-Triphosphate, 5-Fluoro-2'-deoxyuridine-5'-Triphosphate, 2-Thiothymidine-5'-Triphosphate, 5-Bromo-2'-deoxycytidine-5'-Triphosphate, 5-Iodo-2'-deoxycytidine-5'-Triphosphate, 5-trifluoromethyl-2'deoxy-Uridine-5'-triphosphate, 5-Iodo-2'-deoxyuridine-5'-Triphosphate, 5-Bromo-2'-deoxyuridine-5'-Triphosphate, 7-deaza-7-bromo-2'-deoxy-adenosine-5'-triphosphate, 7-deaza-7-iodo-2'-deoxy-adenosine-5'-triphosphate, 7-deaza-7-iodo-2'-deoxy-guanosine-5'-triphosphate, 6-Thio-2'-deoxyguanosine-5'-Triphosphate, alpha-Thiophosphate-deoxythymidine-5'-triphosphate, alpha-Thiophosphate-deoxyadenosine-5'-triphosphate, 5-Fluoro-2-deoxycytidine-5'-triphosphate, 2'-fluoro-2'-deoxy-uridine-5'-triphosphate, 2'-fluoro-2-deoxyuridine-5'-triphosphate, 2'-fluoro-2'-deoxy-cytidine-5'-triphosphate.

The following different nucleotide species were also tested in an experiment similar to that described above but using a strand which was 200 bp in length (SEQ ID NO: 39 is attached at its 3' end to four iSpC3 spacers which are attached at the opposite end to the 5' end of SEQ ID NO: 40 where at least one of C, T, A or G was replaced with a different nucleotide triphosphate species in step 1.2 of Example 1; also including tether sequence SEQ ID NO: 42)-inosine (2'deoxyinosine-5'-triphosphate), 7-Deaza-2'-deoxyguanosine-5'-Triphosphate, abasic (replacing either G or T), glycosylated hydroxymethylated deoxycytidine replaced hmC post polymerase incorporation, 2'-Deoxy-P-nucleoside-5'-Triphosphate (dP), zebularine(2'deoxyebularine-5'-triphosphate), 5-Hydroxymethyl-2'-deoxyuridine-5'-Triphosphate, $N^4$-Methyl-2'-deoxycytidine-5'-Triphosphate, 5-Methyl-2'-deoxycytidine-5'-Triphosphate, 7-Deaza-2'-deoxyadenosine-5'-Triphosphate, 2-Amino-2'-deoxyadenosine-5'-Triphosphate, $N^6$-Methyl-2'-deoxyadenosine-5'-Triphosphate, 2-Aminopurine-2'-deoxyriboside-Triphosphate, 2'-Deoxyuridine-5'-Triphosphate, backbone of the strand changed to LNA, N6-benzyl-2'-deoxyadenosine-5'-triphosphate, 5-Amino-propargyl-2'-deoxyuridine 5'-triphosphate coupled to Cy5, 5-Propynyl-2'-deoxyuridine-5'-Triphosphate, 5-Hydroxymethyl-2'-deoxyuridine-5'-Triphosphate, 6-Aza-2'-deoxyuridine-5'-Triphosphate, 6-Thio-2'-deoxyguanosine-5'-Triphosphate, 5-Formyl-2'-deoxycytidine-5'-Triphosphate, 5-Carboxy-2'-deoxycytidine-5'-Triphosphate and 2-Thio-2'-deoxycytidine-5'-Triphosphate.

Example 3

This example describes how a Trwc Cba (SEQ ID NO: 25) enzyme controlled the movement of modified polynucleotides through a single MspA nanopore (MspA-B2C). The nucleotide species (A and G) in the template polynucleotide were replaced with different nucleotide species (7-deaza-7-iodo-2'-deoxy-adenosine-5'-triphosphate and 7-deaza-7-iodo-2'-deoxy-guanosine-5'-triphosphate) in the modified polynucleotide.

Materials and Methods

The experimental pre-mix was prepared using the same method as described in Example 2 above except the modified DNA construct (SEQ ID NO: 34 which is attached at the 3' end to four iSpC3 spacers which are attached at the opposite end to the 5' end of SEQ ID NO: 38 where A and G were replaced with 7-deaza-7-iodo-2'-deoxy-adenosine-5'-triphosphate and 7-deaza-7-iodo-2'-deoxy-guanosine-5'-triphosphate respectively in step 1.2 of Example 1; also including tether sequence SEQ ID NO: 42, final concentration 0.5 nM) was produced using different nucleotide triphosphate species (C, T, 7-deaza-7-iodo-2'-deoxy-adenosine-5'-triphosphate and 7-deaza-7-iodo-2'-deoxy-guanosine-5'-triphosphate).

The electrical measurements were acquired and helicase-controlled DNA movement monitored using the same method as described in Example 2 above except that the experimental buffer used was (600 mM KCl, 25 mM potassium phosphate, 75 mM potassium ferrocyanide, 25 mM potassium ferricyanide, pH 8.0) and a slightly different potential flip process (120 mV with potential flips down of −100 mV for 2 seconds then 0 mV for 2 seconds 10 minutes) was applied.

Results and Discussion

Helicase controlled DNA movement was observed for the modified DNA construct tested (SEQ ID NO: 34 which is attached at the 3' end to four iSpC3 spacers which are attached at the opposite end to the 5' end of SEQ ID NO: 38 where A and G were replaced with 7-deaza-7-iodo-2'-deoxy-adenosine-5'-triphosphate and 7-deaza-7-iodo-2'-deoxy-guanosine-5'-triphosphate respectively in step 1.2 of Example 1; also including tether sequence SEQ ID NO: 42). A list of other tested modified polynucleotides which were investigated is provided at the end of this example.

Figure 9:
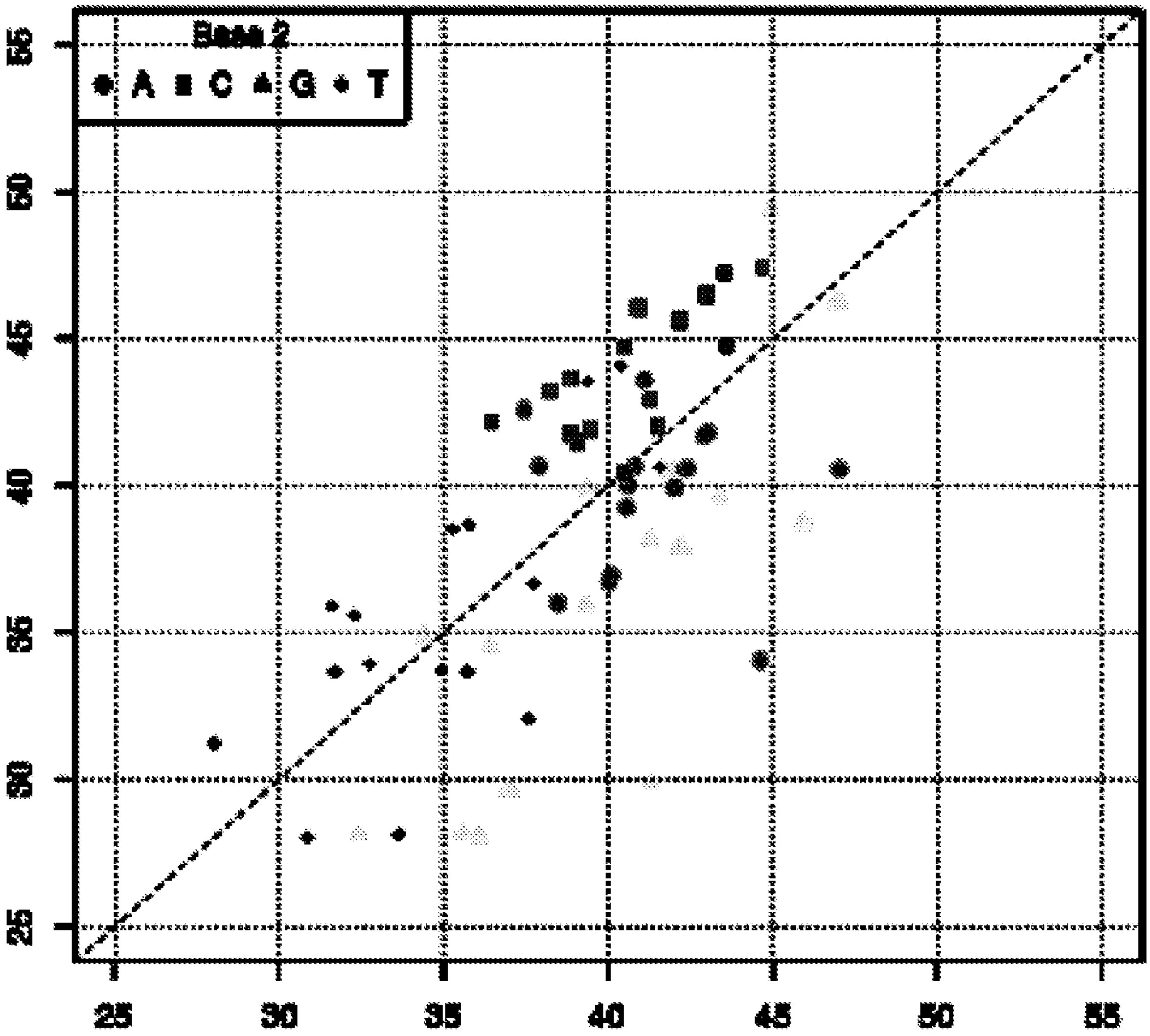
FIG. 9 shows a diagonal dot plot for the modified DNA construct which was made up of C, T, 7-deaza-7-iodo-2'-deoxy-adenosine-5'-triphosphate and 7-deaza-7-iodo-2'-deoxy-guanosine-5'-triphosphate. The diagonal dot plot displays the current level for each base combination in the modified strand plotted against its equivalent in an unmodified strand, such that the large changes in the current-sequence relationship are represented by large displacements from the diagonal.
Figure 10:
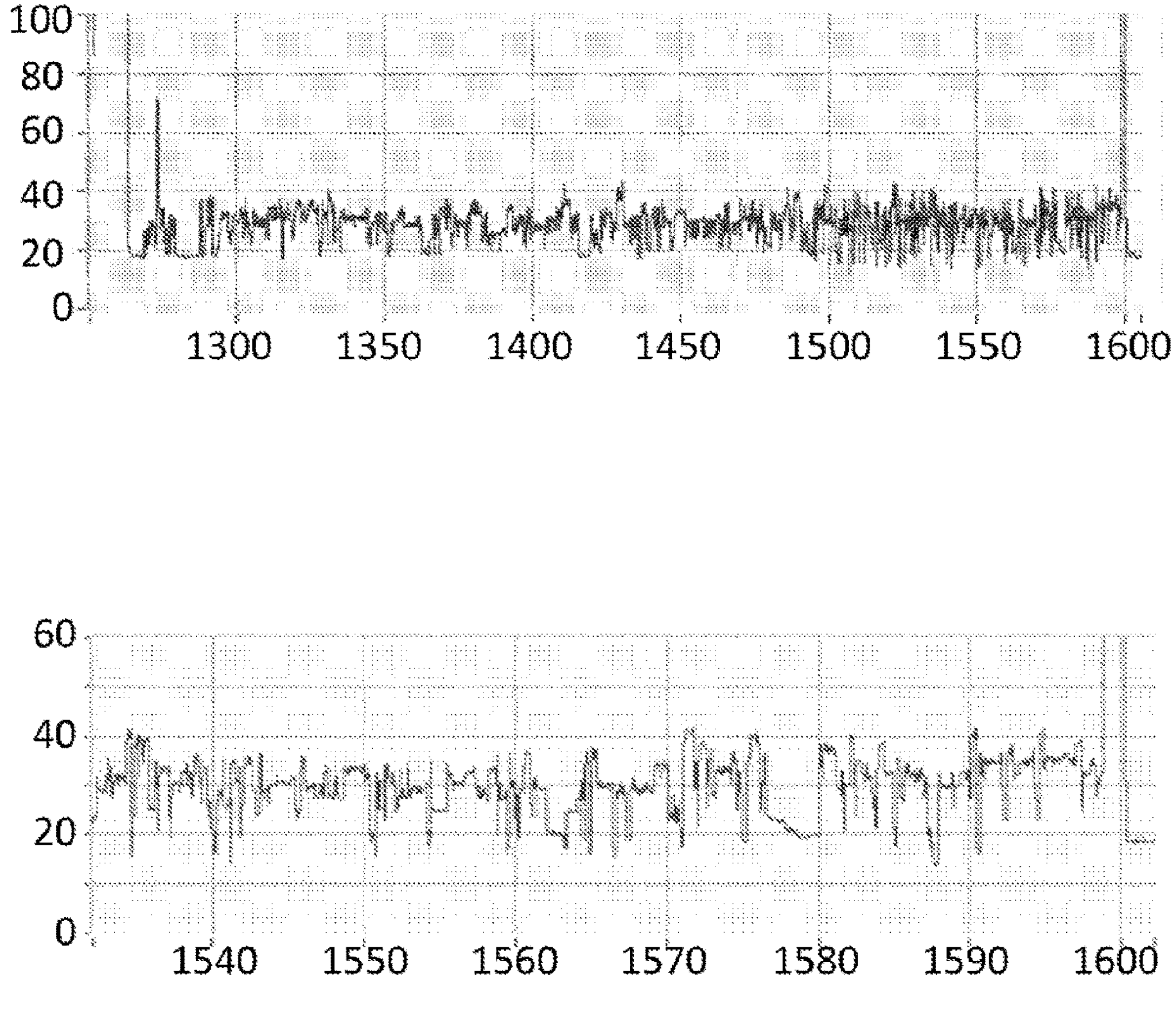
FIG. 10 shows an example current trace (y-axis label=Current (pA), x-axis label=Time (s)) of when a helicase (TrwC Cba (SEQ ID NO: 25) controlled the translocation of the modified DNA construct (SEQ ID NO: 34 which is attached at the 3' end to four iSpC3 spacers which are attached at the opposite end to the 5' end of SEQ ID NO: 38 where A and G were replaced with 7-deaza-7-iodo-2'-deoxy-adenosine-5'-triphosphate and 7-deaza-7-iodo-2'-deoxy-guanosine-5'-triphosphate respectively in step 1.2 of Example 1; also including tether sequence SEQ ID NO: 42, 0.5 nM) through a nanopore (MspA-B2C). The lower current trace is a zoomed in region of the trace above.

The diagonal dot plot shown in FIG. 9 displays the current level for each base combination in the modified strand plotted against its equivalent in an unmodified strand, such that large changes in the current-sequence relationship were represented by large displacements from the diagonal. FIG. 10 shows an example of helicase controlled DNA movement of the modified strand (SEQ ID NO: 34 which is attached at the 3' end to four iSpC3 spacers which are attached at the opposite end to the 5' end of SEQ ID NO: 38 where A and G were replaced with 7-deaza-7-iodo-2'-deoxy-adenosine-5'-triphosphate and 7-deaza-7-iodo-2'-deoxy-guanosine-5'-triphosphate respectively in step 1.2 of Example 1; also including tether sequence SEQ ID NO: 42).

The modifications tested in this example (7-deaza-7-iodo-2'-deoxy-adenosine-5'-triphosphate and 7-deaza-7-iodo-2'-deoxy-guanosine-5'-triphosphate) demonstrated that distinct changes from the standard model (see FIG. 9) were observed when more than one nucleotide species was replaced with a different nucleotide species.

The following different nucleotide species combinations were also tested in the same experimental system described above—(5-Propynyl-2'-deoxycytidine-5'-Triphosphate and 5-Propynyl-2'-deoxyuridine-5'-Triphosphate), (5-Propynyl-2'-deoxyuridine-5'-Triphosphate and 5-Carboxy-2'-deoxycytidine-5'-Triphosphate), (5-Propynyl-2'-deoxyuridine-5'-Triphosphate and 7-Deaza-2'-deoxyguanosine-5'-Triphosphate), (5-Propynyl-2'-deoxyuridine-5'-Triphosphate and 5-Formyl-2'-deoxycytidine-5'-Triphosphate), (5-Propynyl-2'-deoxycytidine-5'-Triphosphate and 2-Amino-2'-deoxyadenosine-5'-Triphosphate), (2'-fluoro-2'-deoxyadenosine-5'-triphosphate and 5-trifluoromethyl-2'deoxy-Uridine-5'-triphosphate), (5-Propynyl-2'-deoxyuridine-5'-Triphosphate and 2'-fluoro-2'-deoxyadenosine-5'-triphosphate), (2'-fluoro-2'-deoxyadenosine-5'-triphosphate and 7-deaza-7-iodo-2-deoxyguanosine-5'-triphosphate), (5-Iodo-2'-deoxycytidine-5'-Triphosphate and 7-deaza-7-iodo-2-deoxyguanosine-5'-triphosphate), (5-Fluoro-2-deoxycytidine-5'-triphosphate and 7-deaza-7-iodo-2-deoxyguanosine-5'-triphosphate), (5-Fluoro-2-deoxycytidine-5'-triphosphate and 5-Iodo-2'-deoxyuridine-5'-Triphosphate), (5-Fluoro-2-deoxycytidine-5'-triphosphate and 5-Propynyl-2'-deoxyuridine-5'-Triphosphate), (2-fluoro-adenosine-5'-triphosphate and 5-Iodo-2'-deoxyuridine-5'-Triphosphate), (2'-fluoro-2'-deoxyadenosine-5'-triphosphate and 5-Iodo-2'-deoxyuridine-5'-Triphosphate), (2-fluoro-adenosine-5'-triphosphate and 5-Propynyl-2'-deoxyuridine-5'-Triphosphate), (5-Propynyl-2'-deoxyuridine-5'-Triphosphate and 7-deaza-7-iodo-2-deoxyguanosine), (5-Iodo-2'-deoxyuridine-5'-Triphosphate and 7-deaza-7-iodo-2-deoxyguanosine-5'-triphosphate), (5-Bromo-2'-deoxyuridine-5'-Triphosphate and 7-deaza-7-iodo-2-deoxyguanosine-5'-triphosphate), (2-fluoro-adenosine-5'-triphosphate and 5-Bromo-2'-deoxyuridine-5'-Triphosphate), (2'-fluoro-2'deoxyguanosine-5'-triphosphate and 5-Bromo-2'-deoxyuridine-5'-Triphosphate), (2'-fluoro-2'deoxyguanosine-5'-triphosphate and 5-Iodo-2'-deoxyuridine-5'-Triphosphate), (2'-fluoro-2'deoxyguanosine-5'-triphosphate and 2-fluoro-adenosine-5'-triphosphate), (2'-fluoro-2'deoxyguanosine-5'-triphosphate and 5-Bromo-2'-deoxyuridine-5'-Triphosphate) and (2'-fluoro- 2'deoxyguanosine-5'-triphosphate and 5-Iodo-2'-deoxyuridine-5'-Triphosphate).

Example 4

This example describes how a Trwc Cba (SEQ ID NO: 25) enzyme controlled the movement of modified polynucleotides through a single MspA nanopore (MspA-B2C). The nucleotide species (C, T and A) in the template polynucleotide were replaced with different nucleotide species (5-Propynyl-2'-deoxycytidine-5'-Triphosphate, 5-propynyl-2'-deoxyuridine-5'-triphosphate and 2-aminopurine-2'-deoxyriboside-triphosphate).

Materials and Methods

The experimental pre-mix was prepared using the same method as described in Example 2 above except the modified DNA construct (SEQ ID NO: 34 which is attached at the 3' end to four iSpC3 spacers which are attached at the opposite end to the 5' end of SEQ ID NO: 38 where C, T and A were replaced with 5-Propynyl-2'-deoxycytidine-5'-Triphosphate, 5-propynyl-2'-deoxyuridine-5'-triphosphate and 2-aminopurine-2'-deoxyriboside-triphosphate respectively in step 1.2 of Example 1; also including tether sequence SEQ ID NO: 42, final concentration 0.5 nM) was produced using different nucleotide species (7-deaza-7-iodo-2'-deoxy-adenosine-5'-triphosphate and 7-deaza-7-iodo-2'-deoxy-guanosine-5'-triphosphate).

The electrical measurements were acquired and helicase-controlled DNA movement monitored using the same method as described in Example 2 above except that the experimental buffer used was (600 mM KCl, 25 mM potassium phosphate, 75 mM potassium ferrocyanide, 25 mM potassium ferricyanide, pH 8.0) and a slightly different potential flip process (120 mV with potential flips down of −100 mV for 2 seconds then 0 mV for 2 seconds 10 minutes) was applied.

Results and Discussion

Helicase controlled DNA movement was observed for the modified DNA construct tested (SEQ ID NO: 34 which is attached at the 3' end to four iSpC3 spacers which are attached at the opposite end to the 5' end of SEQ ID NO: 38 where C, T and A were replaced with 5-Propynyl-2'-deoxycytidine-5'-Triphosphate, 5-propynyl-2'-deoxyuridine-5'-triphosphate and 2-aminopurine-2'-deoxyriboside-triphosphate respectively in step 1.2 of Example 1; also including tether sequence SEQ ID NO: 42). A list of other tested modified polynucleotides which were investigated is provided at the end of this example.

Figure 11:
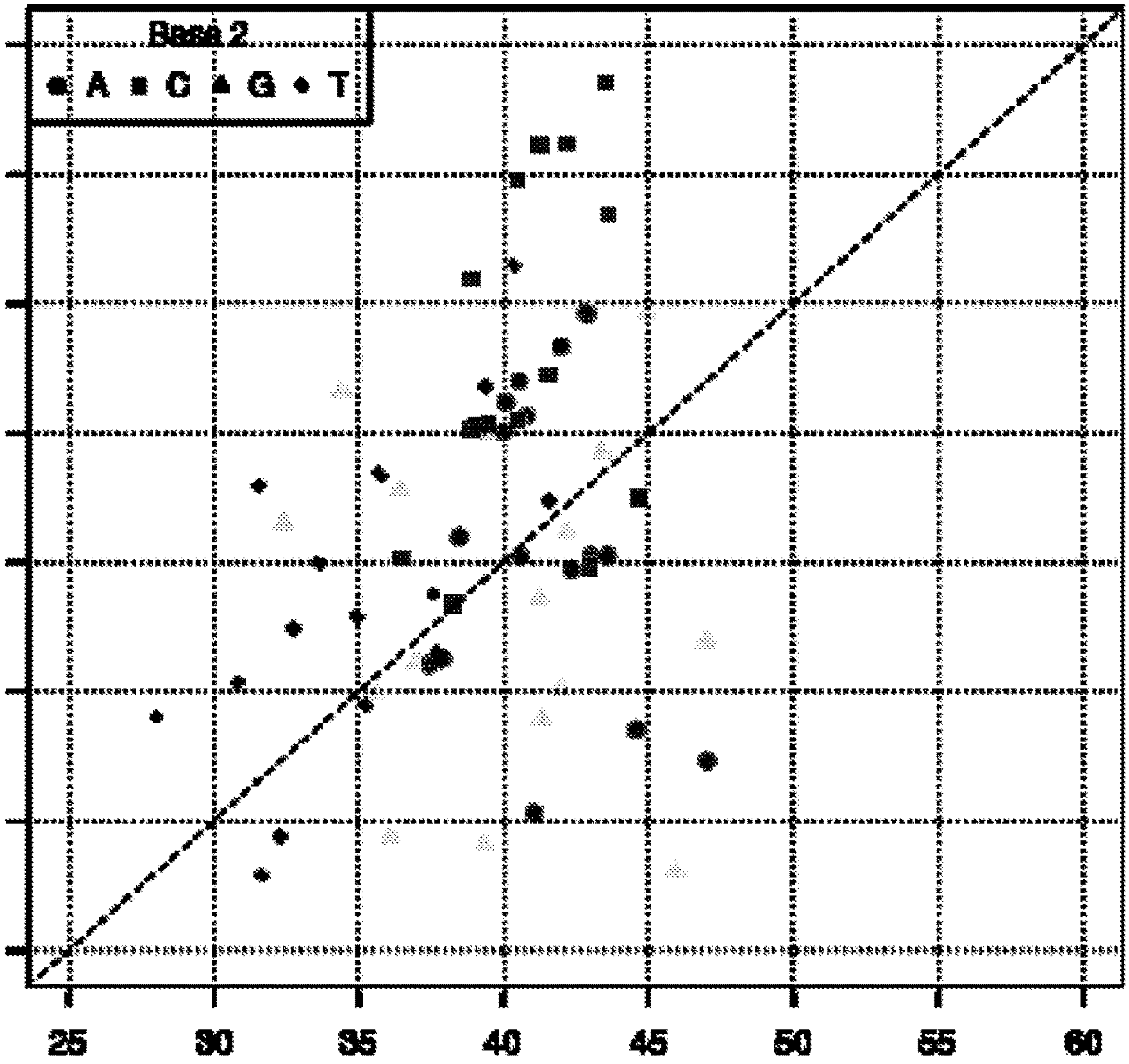
FIG. 11 shows a diagonal dot plot for the modified DNA construct which was made up of G, 5-Propynyl-2'-deoxycytidine-5'-Triphosphate, 5-propynyl-2'-deoxyuridine-5'-triphosphate and 2-aminopurine-2'-deoxyriboside-triphosphate. The diagonal dot plot displays the current level for each base combination in the modified strand plotted against its equivalent in an unmodified strand, such that the large changes in the current-sequence relationship are represented by large displacements from the diagonal.
Figure 12:
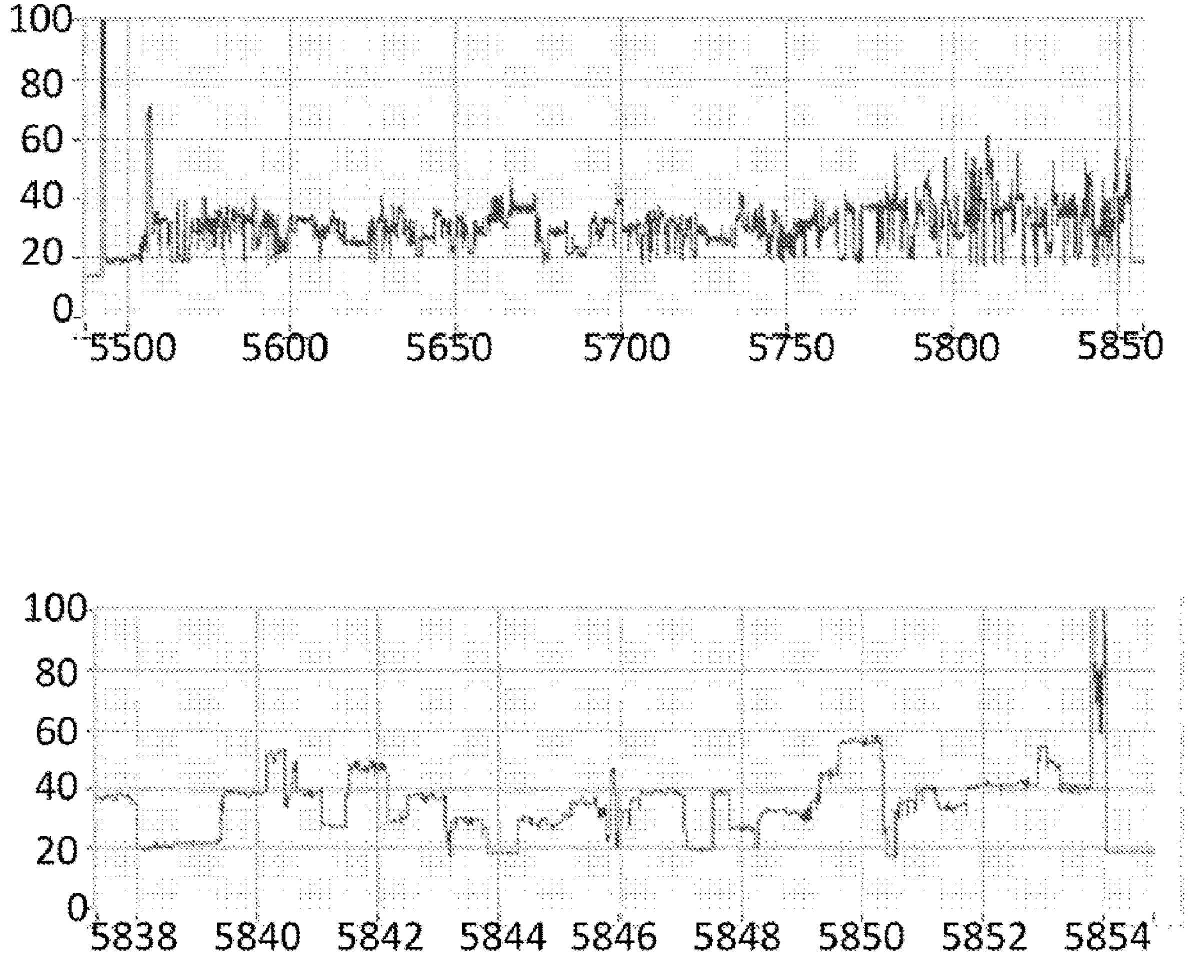
FIG. 12 shows an example current trace (y-axis label=Current (pA), x-axis label=Time (s)) of when a helicase (TrwC Cba (SEQ ID NO: 25) controlled the translocation of the modified DNA construct (SEQ ID NO: 34 which is attached at the 3' end to four iSpC3 spacers which are attached at the opposite end to the 5' end of SEQ ID NO: 38 where C, T and A were replaced with 5-Propynyl-2'-deoxycytidine-5'-Triphosphate, 5-propynyl-2'-deoxyuridine-5'-triphosphate and 2-aminopurine-2'-deoxyriboside-triphosphate respectively in step 1.2 of Example 1; also including tether sequence SEQ ID NO: 42, 0.5 nM) through a nanopore (MspA-B2C). The lower current trace is a zoomed in region of the trace above.

The diagonal dot plot shown in FIG. 11 displays the current level for each base combination in the modified strand plotted against its equivalent in an unmodified strand, such that large changes in the current-sequence relationship were represented by large displacements from the diagonal. FIG. 12 shows an example of helicase controlled DNA movement of the modified strand (SEQ ID NO: 34 which is attached at the 3' end to four iSpC3 spacers which are attached at the opposite end to the 5' end of SEQ ID NO: 38 where A and G were replaced with 75-Propynyl-2'-deoxycytidine-5'-Triphosphate, 5-propynyl-2'-deoxyuridine-5'-triphosphate and 2-aminopurine-2'-deoxyriboside-triphosphate respectively in step 1.2 of Example 1; also including tether sequence SEQ ID NO: 42).

The modifications tested in this example (5-Propynyl-2'-deoxycytidine-5'-Triphosphate, 5-propynyl-2'-deoxyuridine-5'-triphosphate and 2-aminopurine-2'-deoxyriboside-triphosphate) demonstrated that distinct changes from the standard model (as was clear from FIG. 11) were observed when more than one nucleotide species was replaced with a different nucleotide species.

The following different nucleotide species combinations were also tested in the same experimental system described above—(2'-fluoro-2'-deoxyadenosine-5'-triphosphate, 5-Iodo-2'-deoxyuridine-5'-Triphosphate and 7-deaza-7-iodo-2-deoxyguanosine-5'-triphosphate), (2-fluoro-adenosine-5'-triphosphate, 5-Propynyl-2'-deoxyuridine-5'-Triphosphate and 7-deaza-7-iodo-2-deoxyguanosine-5'-triphosphate) and (2'-fluoro-2'-deoxyadenosine-5'-triphosphate, 5-Propynyl-2'-deoxyuridine-5'-Triphosphate and 7-deaza-7-iodo-2-deoxyguanosine-5'-triphosphate).

Example 5

This example describes how a Trwc Cba (SEQ ID NO: 25) enzyme controlled the movement of modified polynucleotides through a single MspA nanopore MspA MS(B1-G75S/G77S/L88N/D90Q/D91Q/Q126R) (MS-QQ) (SEQ ID NO: 2 with mutations G75S/G77S/L88N/D90Q/D91Q/Q126R). The nucleotide species (G) in the template polynucleotide was replaced with a different nucleotide triphosphate species (7-deaza-7-iodo-2'-deoxy-guanosine-5'triphosphate) in the modified polynucleotide.

Materials and Methods

The experimental pre-mix was prepared using the same method as described in Example 2 above except the modified DNA construct (SEQ ID NO: 34 which is attached at the 3' end to four iSpC3 spacers which are attached at the opposite end to the 5' end of SEQ ID NO: 38 where G has been replaced with 7-deaza-7-iodo-2'-deoxy-guanosine-5'triphosphate in step 1.2 of Example 1; also including tether sequence SEQ ID NO: 42) was produced using different nucleotide species (7-deaza-7-iodo-2'-deoxy-guanosine-5'triphosphate) and was used at a lower concentration (0.25 nM final concentration).

The electrical measurements were acquired and helicase-controlled DNA movement monitored using the same method as described in Example 2 above.

Results and Discussion

Helicase controlled DNA movement was observed for the modified DNA construct tested (SEQ ID NO: 34 which is attached at the 3' end to four iSpC3 spacers which are attached at the opposite end to the 5' end of SEQ ID NO: 38 where G has been replaced with 7-deaza-7-iodo-2'-deoxy-guanosine-5'triphosphate in step 1.2 of Example 1; also including tether sequence SEQ ID NO: 42).

Figure 13:
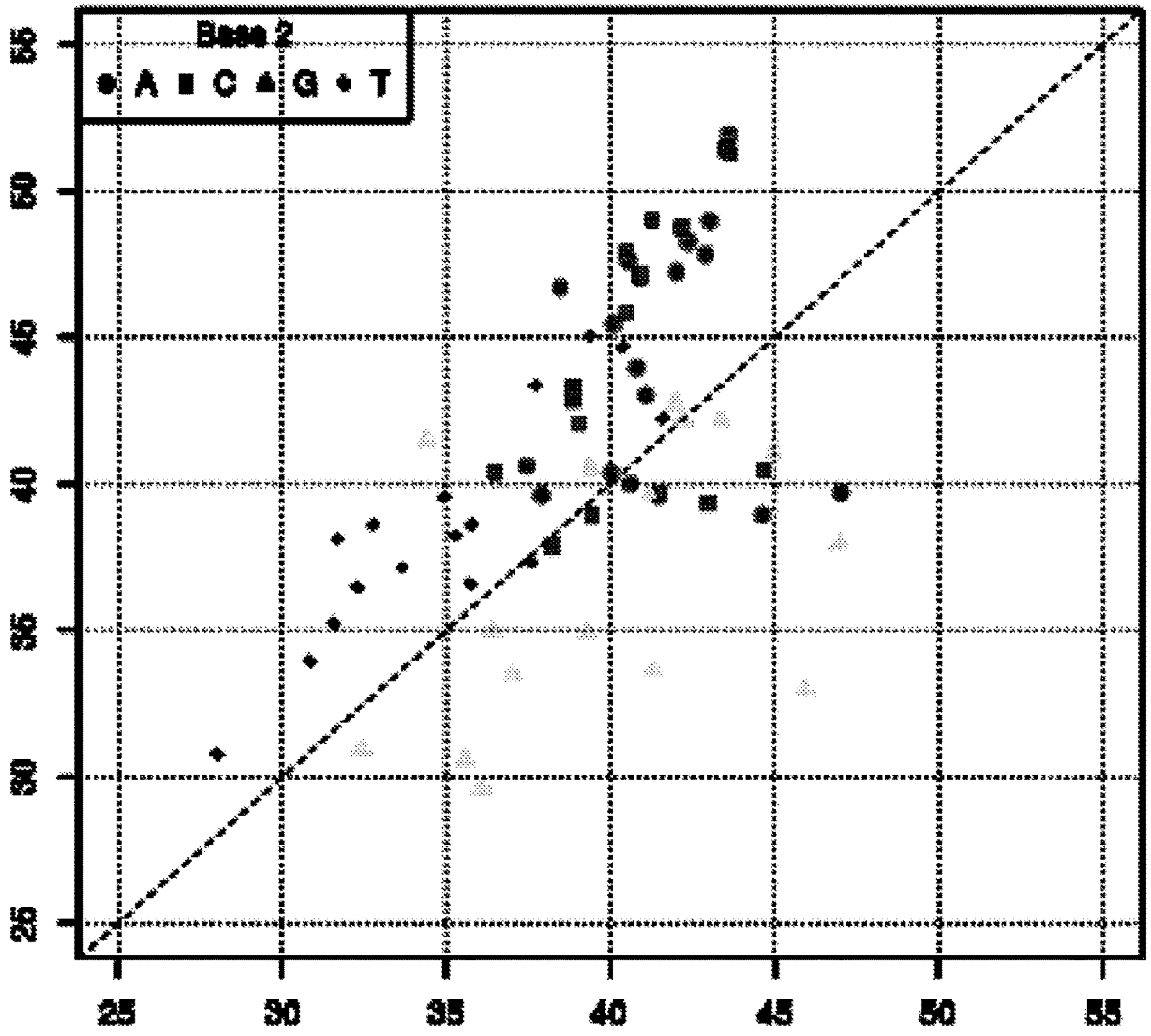
FIG. 13 shows a diagonal dot plot for the modified DNA construct which was made up of C, T, A and 7-deaza-7-iodo-2'-deoxy-guanosine-5'triphosphate. The diagonal dot plot displays the current level for each base combination in the modified strand plotted against its equivalent in an unmodified strand, such that the large changes in the current-sequence relationship are represented by large displacements from the diagonal.
Figure 14:
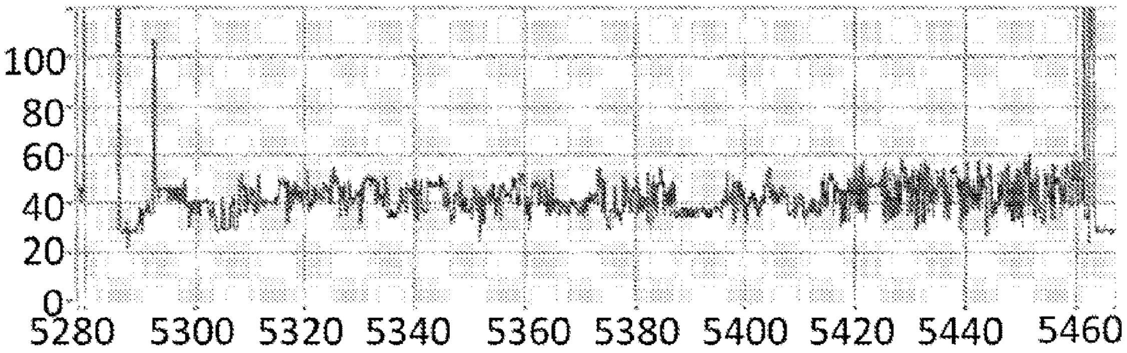
FIG. 14 shows an example current trace (y-axis label=Current (pA), x-axis label=Time (s)) of when a helicase (TrwC Cba (SEQ ID NO: 25) controlled the translocation of the modified DNA construct (SEQ ID NO: 34 which is attached at the 3' end to four iSpC3 spacers which are attached at the opposite end to the 5' end of SEQ ID NO: 38 where G was replaced with 7-deaza-7-iodo-2'-deoxy-guanosine-5'triphosphate in step 1.2 of Example 1; also including tether sequence SEQ ID NO: 42, 0.5 nM) through a nanopore (MspA MS(B1-G75S/G77S/L88N/D90Q/D91Q/Q126R (MS-QQ) SEQ ID NO: 2 with mutations G75S/G77S/L88N/D90Q/D91Q/Q126R). The lower current trace is a zoomed in region of the trace above.
Figure 14:
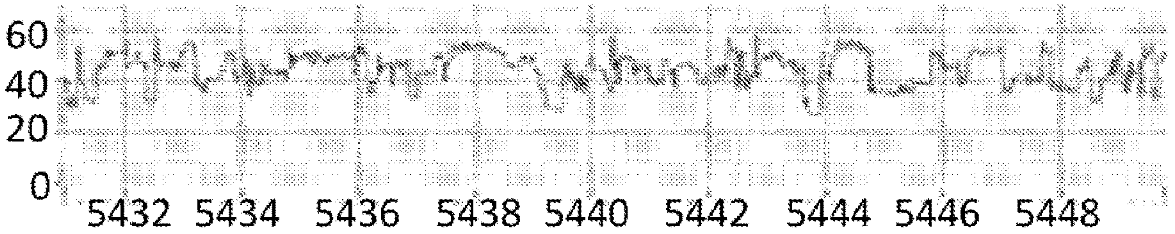

The diagonal dot plot shown in FIG. 13 displays the current level for each base combination in the modified strand plotted against its equivalent in an unmodified strand, such that large changes in the current-sequence relationship were represented by large displacements from the diagonal. FIG. 14 shows an example of helicase controlled DNA movement of the modified strand (SEQ ID NO: 34 which is attached at the 3' end to four iSpC3 spacers which are attached at the opposite end to the 5' end of SEQ ID NO: 38 where G was replaced with 7-deaza-7-iodo-2'-deoxy-guanosine-5'triphosphate in step 1.2 of Example 1; also including tether sequence SEQ ID NO: 42). This example illustrated that it was also possible to observe distinct changes when compared to the standard model when a different mutant nanopore was used (MS-QQ) in this instance).

Example 6

This example describes how a T4 Dda-E94C/A360C (SEQ ID NO: 24 with mutations E94C/A360C) enzyme controlled the movement of a 3.6 kB strand of modified polynucleotide through a single MspA nanopore (MspA-B2C). The nucleotide species (G) in the template polynucleotide X (described below) was replaced with a different nucleotide species (7-deaza-7-iodo-2'-deoxy-guanosine-5'triphosphate) in the modified polynucleotide. This experiment was also repeated when the different nucleotide species were either 1) 5-carboxy-2'-deoxycytidine-5'triphosphate used with dATP/dGTP/dTTP or 2) 2-fluoro-adenosine-5'triphosphate used with dCTP/dGTP/dTTP.

Materials and Methods

A modified base copy of the original template and complement ~3,600 bp dsDNA fragment of Lambda DNA sample (template strand=30 iSpC3 spacers attached to the 5' end of SEQ ID NO: 45 which is attached at the 3' end to four iSp18 spacers which are attached at the opposite end to the 5' end of SEQ ID NO: 36 which is attached at the 3' end to four 5-nitroindoles which are attached at the opposite end to the 5' end of SEQ ID NO:37 and the complement strand=30 iSpC3 spacers attached to the 5' end of SEQ ID NO: 45 which is attached at the 3' end to four iSp18 spacers which are attached at the opposite end to the 5' end of SEQ ID NO: 36 which is attached at the 3' end to four 5-nitroindoles which are attached at the opposite end to the 5' end of SEQ ID NO:47) needed for 5 mer model generation was produced using the following method.

A 3447 bp fragment of lambda (SEQ ID NO: 35 shows the sense sequence of dsDNA) was amplified using LongAmp™ Taq DNA polymerase (NEB, catalog No: M0323S) with the following primers (SEQ ID NO: 48 and SEQ ID NO: 49). Reactions were cycled as follows; 94° C. for 30 secs, (94° C. for 15secs, 57° C. for 30 secs, 65° C. for 3 min)30, 65° C. 10 mins. The 3.6 kb fragment was run on a 0.8% TAE agarose gel and gel purified, eluting in nuclease free water.

A second round of PCR was then carried out using the first round product as the template (polynucleotide X). Each reaction contained the following (final concentrations in the 10 ul reaction are given in brackets); ThermoPol Buffer (1×), 3.6 kb Template (polynucleotide X, 5 ng $ul^{-1}$), primer 1 (200 nM, 30 iSpC3 spacers attached at one end to the 5' end of SEQ ID NO:45 which is attached at its 3' end to four iSp18 spacers which are attached at the opposite end to the 5' end of SEQ ID NO: 36 which is attached at the 3' end to four 5-nitroindoles which are attached at the opposite end to the 5' end of SEQ ID NO: 31) and primer 2 (200 nM, 30 iSpC3 spacers attached at one end to the 5' end of SEQ ID NO: 45 which is attached at its 3' end to four iSp18 spacers which are attached at the opposite end to the 5' end of SEQ ID NO: 36 which is attached at the 3' end to four 5-nitroindoles which are attached at the opposite end to the 5' end of SEQ ID NO: 46), 0.2 mM of modified base triphosphate/s (7-deaza-7-iodo-2'-deoxy-guanosine-5'triphosphate or 5-carboxy-2'-deoxycytidine-5'triphosphate or 2-fluoro-adenosine-5'triphosphate depending on the experiment), 0.2 mM of the remaining dNTP/s and 1 U of Polymerase (usually 9°N unless using dUTP when used Taq). The mixture was then mixed well by pipetting and the tube was transferred to a PCR block and cycled; 95° C. for 2 mins, 56° C. for 20 secs, 72° C. for 30 mins. The sample was then 0.7×SPRI purified, washed twice in 200 ul 70% EtOH and eluted in 5 ul $nH_2O$. 5× binding buffer+EDTA (1.5 ul, 1×=25 mM potassium phosphate buffer pH 7.5, 150 mM KCl and 1 mM EDTA) and a DNA tether (1 ul of 500 nM, SEQ ID NO: 42 which is attached at its 3' end to six iSp18 spacers attached at the opposite end to two T's and a 3' cholesterol TEG) were added to the sample and it was incubated at room temp for 15 mins. T4 Dda-E94C/A360C (SEQ ID NO: 24 with mutations E94C/A360C, 0.6 ul) was added and the mixture incubated at room temperature for 10 mins. TMAD (1 μL, 0.8 mM) was then added and the sample incubated at room temperature for a further 10 mins. Finally, 500 mM KCl pH 8.0, 25 mM potassium phosphate buffer (300 ul) with MgCl2 (1 mM) and rATP (2 mM) was added.

Electrical measurements were acquired at 20° C. (by placing the experimental system on a cooler plate) from single MspA nanopores (MspA-B2C) inserted in block co-polymer in buffer (600 mM KCl, 25 mM K Phosphate buffer, 75 mM Potassium Ferrocyanide (II), 25 mM Potassium Ferricyanide (III), pH 8). After achieving a single pore inserted in the block co-polymer, then buffer (3 mL, 960 mM KCl, 3 mM Potassium Ferrocyanide (II), 1 mM Potassium ferricyanide (III), 25 mM potassium phosphate pH 8) was flowed through the system to remove any excess MspA nanopores (MspA-B2C). The pre-mix as described above was then added to the single nanopore experimental system. The experiment where G was replaced with the modified base 7-deaza-7-iodo-2'-deoxy-guanosine-5'triphosphate was carried out for two hours following a potential flip process (120 mV with potential flips down of −100 mV for 2 seconds then 0 mV for 2 seconds every 60 minutes) and helicase-controlled DNA movement was monitored. The experiments where the different nucleotide species were either 1) 5-carboxy-2'-deoxycytidine-5'triphosphate used with dATP/dGTP/dTTP or 2) 2-fluoro-adenosine-5'triphosphate used with dCTP/dGTP/dTTP were run at 140 mV for 6 hours and again helicase-controlled DNA movement was monitored.

Results and Discussion

Helicase controlled DNA movement was observed for the 3.6 kB modified DNA constructs tested.

Figure 15:
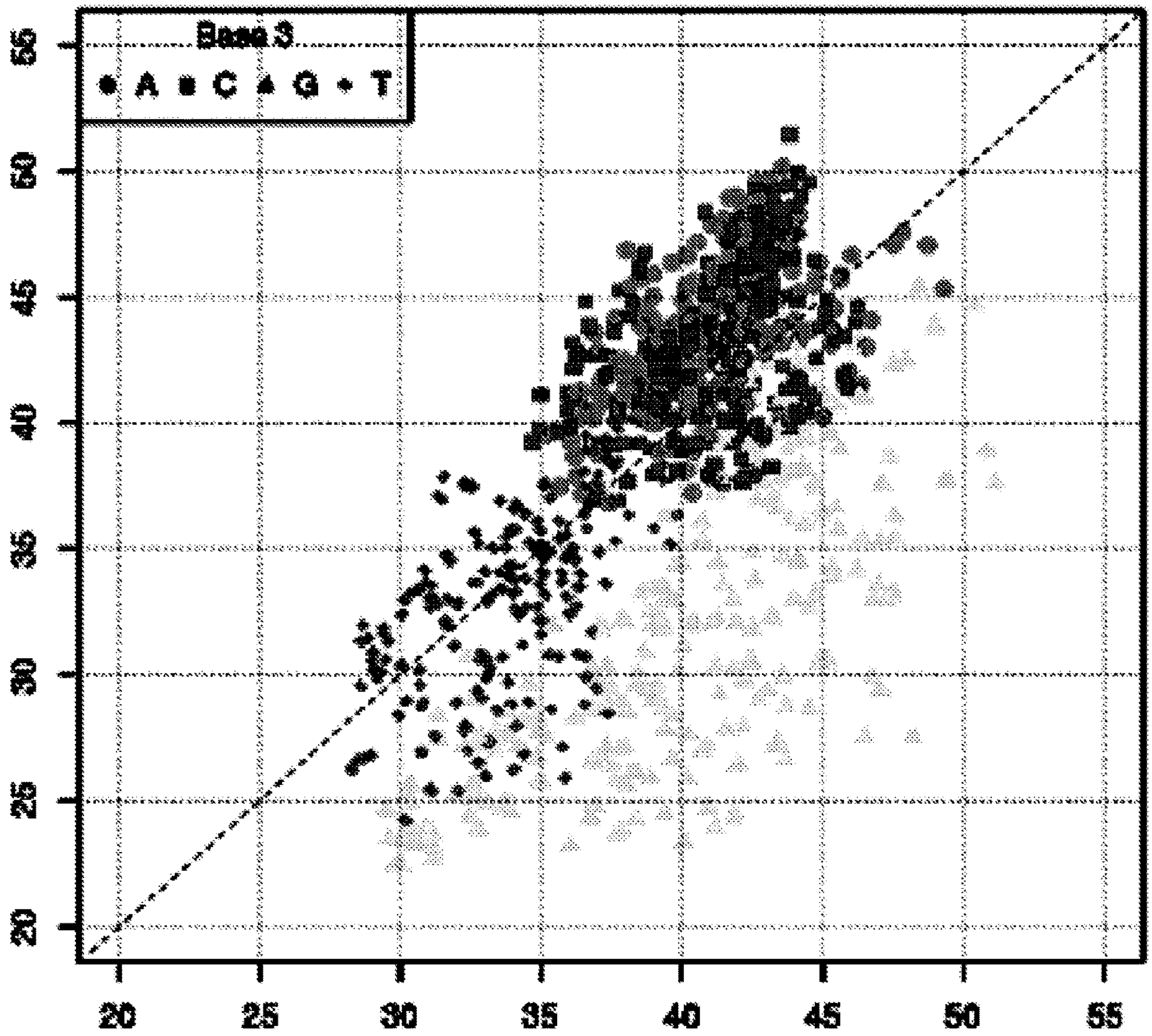
FIG. 15 shows a diagonal dot plot for the 3.6 kB modified DNA construct which was made up of C, T, A and 7-deaza-7-iodo-2'-deoxy-guanosine-5'triphosphate. The diagonal dot plot displays the current level for each base combination in the modified strand plotted against its equivalent in an unmodified strand, such that the large changes in the current-sequence relationship are represented by large displacements from the diagonal. This graph uses a Kmer model based on a 5mer instead of a 3 mer as shown in the previous figures. Points are distinguished in representation according to the identity of the base at the third position in such kmers.
Figure 16:
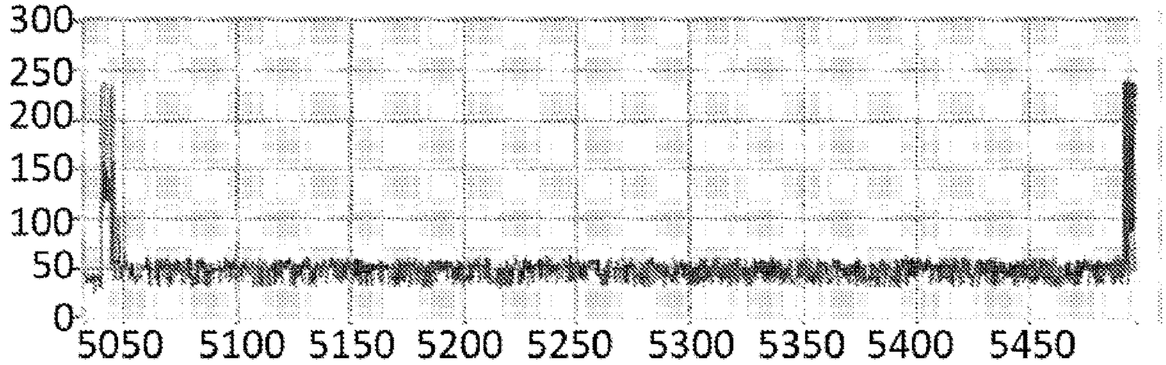
FIG. 16 shows an example current trace (y-axis label=Current (pA), x-axis label=Time (s)) of when a helicase (T4 Dda-E94C/A360C (SEQ ID NO: 24 with mutations E94C and A360C) controlled the translocation of the modified DNA construct (SEQ ID NO: 35 which is attached at its 3' end by four iSpC3 spacers which are attached at the opposite end to the 5' end SEQ NO: 36; the 3' end of SEQ ID NO: 36 is attached to an additional four iSpC3 spacers which are attached at the opposite end to the 5' end of SEQ ID NO: 37 where during synthesis all the G's in these sequences are replaced with 7-deaza-7-iodo-2'-deoxy-guanosine-5'triphosphate; also including tether sequence SEQ ID NO: 42, 0.2 nM) through a nanopore (MspA-B2C). The lower current trace is a zoomed in region of the trace above.
Figure 16:
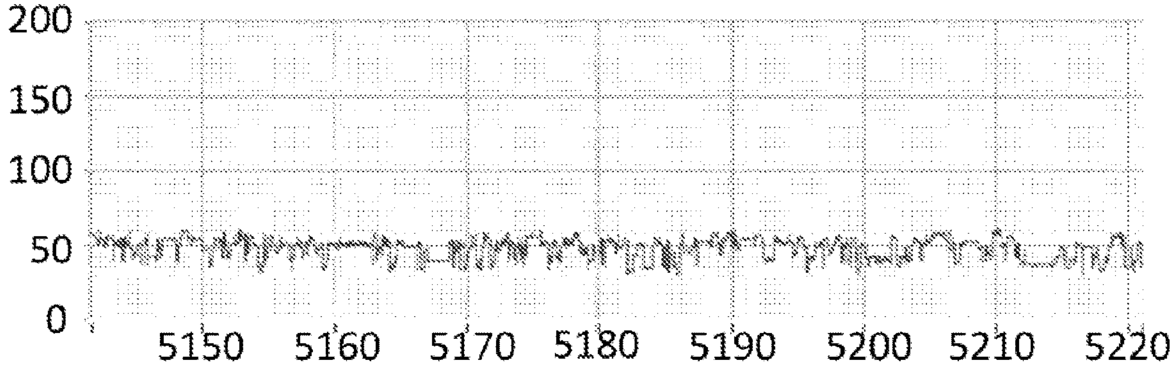

The diagonal dot plot shown in FIG. 15 displays the current level for each base combination in the modified strand plotted against its equivalent in an unmodified strand, such that large changes in the current-sequence relationship were represented by large displacements from the diagonal. FIG. 15 shows a similar plot to that previously described where the kmer positions in the new strand were plotted against their equivalents in the old strand. However, this time k=5 instead of k=3; because there are so many more 5mer combinations possible than 3mer combinations, more points are shown on the graph. A 5mer model gave a more precise fit to the current levels found in each strand event, but can only be built in longer strands where there were sufficient bases such that most combinations were found at least once in the sequence. FIG. 16 shows an example of helicase controlled DNA movement of the modified strand. This example illustrated that it was possible to observe distinct changes when compared to the standard model when a 3.6 kB modified strand was used.

Helicase controlled DNA movement was also observed for the 3.6 kB modified DNA which was produced using the nucleotide combinations of either 1) 5-carboxy-2'-deoxycytidine-5'triphosphate used with dATP/dGTP/dTTP or 2) 2-fluoro-adenosine-5'triphosphate used with dCTP/dGTP/dTTP.

Figure 19:
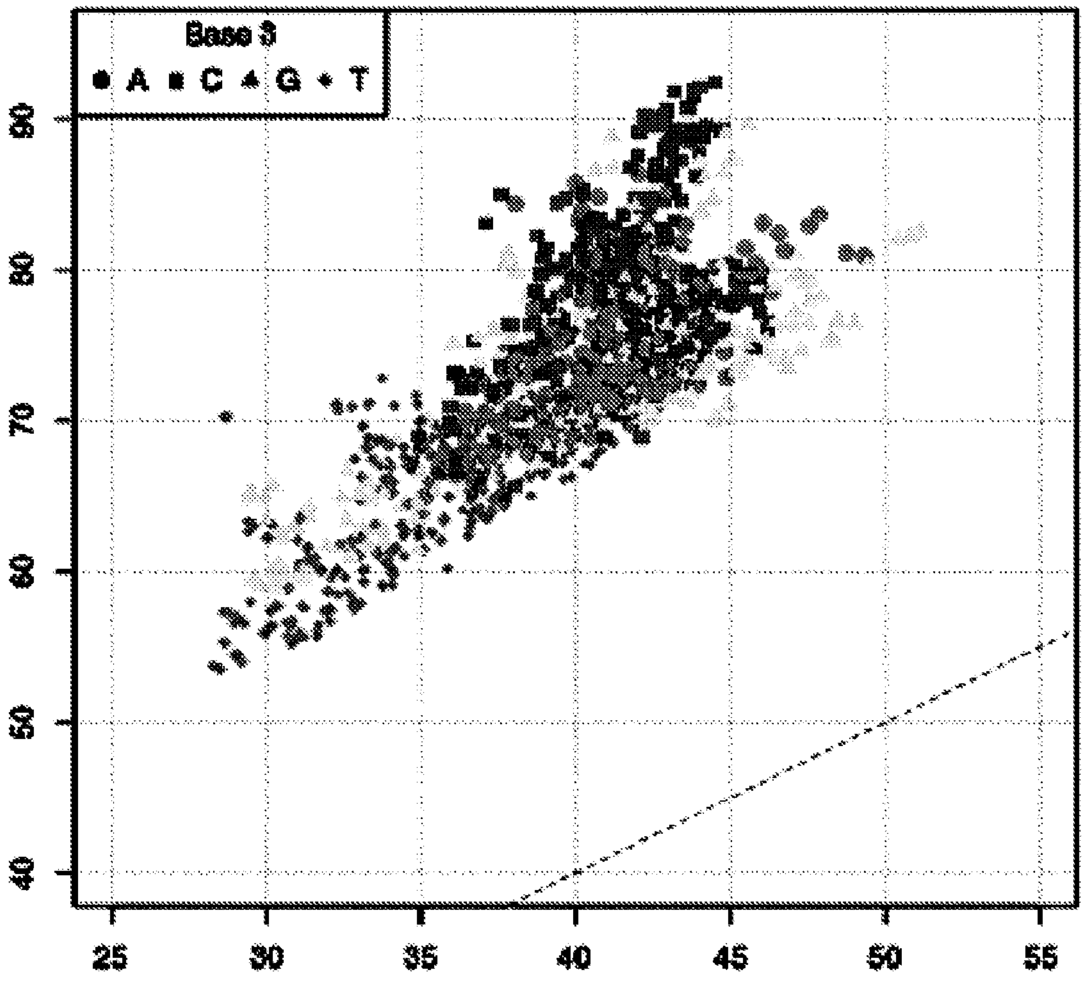
FIG. 19 shows a diagonal dot plot for the 3.6 kB modified DNA construct which was made up of A, T, G and 5-carboxy-2'-deoxycytidine-5'triphosphate. The diagonal dot plot displays the current level for each base combination in the modified strand plotted against its equivalent in an unmodified strand, such that the large changes in the current-sequence relationship are represented by large displacements from the diagonal. This graph uses a Kmer model based on a 5mer instead of a 3 mer as shown in the previous figures. Points are distinguished in representation according to the identity of the base at the third position in such kmers.
Figure 20:
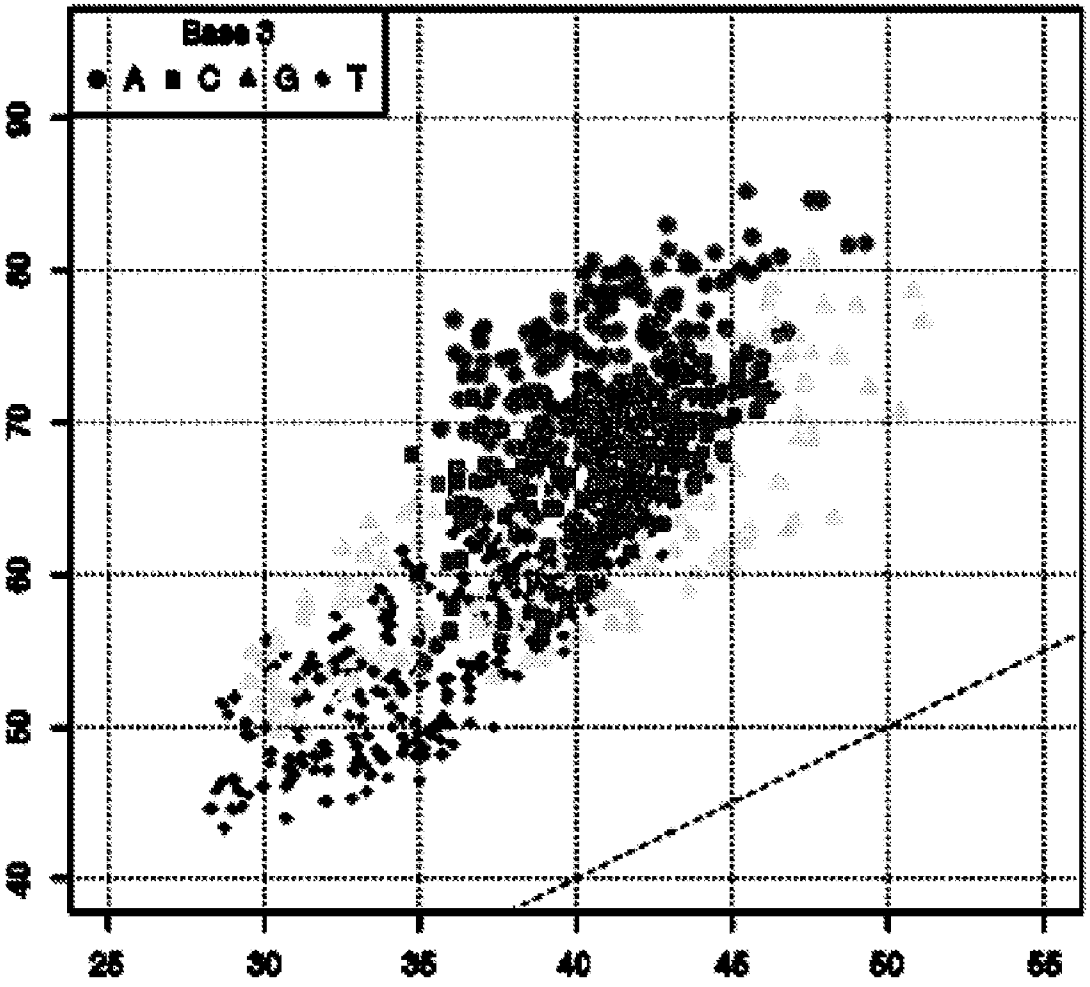
FIG. 20 shows a diagonal dot plot for the 3.6 kB modified DNA construct which was made up of C, T, G and 2-fluoro-adenosine-5'triphosphate. The diagonal dot plot displays the current level for each base combination in the modified strand plotted against its equivalent in an unmodified strand, such that the large changes in the current-sequence relationship are represented by large displacements from the diagonal. This graph uses a Kmer model based on a 5mer instead of a 3 mer as shown in the previous figures. Points are distinguished in representation according to the identity of the base at the third position in such kmers.

The diagonal dot plots for base combinations 1 and 2 are shown in FIGS. 19 and 20 (again these figures have a k=5 Kmer). These examples illustrate that it was possible to observe distinct changes when compared to the standard model when a 3.6 kB modified strand was used (which was produced using the base combinations 1) 5-carboxy-2'-deoxycytidine-5'triphosphate used with dATP/dGTP/dTTP or 2) 2-fluoro-adenosine-5'triphosphate used with dCTP/dGTP/dTTP).

Example 7

This example describes how a T4 Dda-E94C/A360C (SEQ ID NO: 24 with mutations E94C/A360C) enzyme controlled the movement of modified polynucleotides through a single MspA nanopore. The nucleotide species (A) in the randomly fragmented template polynucleotide lambda genomic DNA was replaced with a different nucleotide species (2'-fluoro-2'-deoxyadenosine-5'-triphosphate) in the modified polynucleotide.

Materials and Methods

Figure 17:
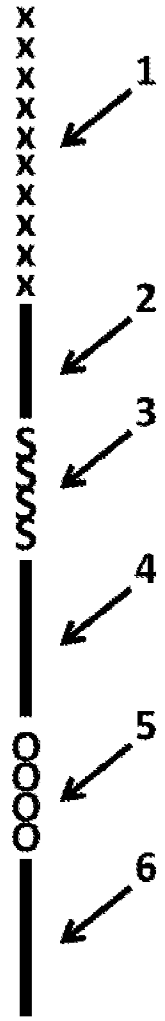
FIG. 17 shows a cartoon representation of the primer used in Example 7. Region 1 corresponds to 30 iSpC3 spacers. Region 2 corresponds to SEQ ID NO: 45. Region 3 corresponds to four iSp18 spacers. Region 4 corresponds to SEQ ID NO: 36. Region 5 corresponds to four 5-nitroindoles. Region 6 corresponds to SEQ ID NO: 46.

Lambda genomic DNA dam$^-$ (1 ug, NEB) was randomly fragmented using a Covaris g-tube at 6,000 rpm for 1 minute. The recovered DNA was then end-repaired and dA-tailed, using NEB's NEBNext End-Repair and NEBNext dA-tailing Kits respectively (according to the manufacturer's instructions) each time purified using SPRI beads (Agencourt AMPure). Recovered DNA was then ligated to an adapter (400 nM, SEQ ID NO: 43 and 44) with 1× Blunt/TA Master Mix (NEB), for 15 mins at room temperature and then purified using SPRI beads (Agencourt AMPure). To the adapter ligated DNA (1 ug) ThermoPol Buffer (NEB) was added to make 100 ul of 1×, along with 200 nM of each dNTP (2'-fluoro-2'-deoxyadenosine-5'-triphosphate, 2'-deoxyguanosine-5'-triphosphate, 2'-deoxythymine-5'-triphosphate, 2'-deoxycytosine-5'-triphosphate), 200 nM primer (see FIG. 17 for cartoon image of primer structure and appropriate sequences) and 10 units of 9°N DNA Polymerase (NEB). Reactions were then heated to 95° C. for 2.5 mins, 55° C. for 20 secs and 72° C. for 30 mins. Amplified DNA was then purified using SPRI beads (Agencourt AMPure).

A DNA tether (50 nM, SEQ ID NO: 42) was annealed in 25 mM potassium phosphate (pH 8), 151 mM KCl for 15 mins at room temperature. T4 Dda-E94C/A360C (200 nM, SEQ ID NO: 24 with mutations E94C/A360C) was then added and the reaction was left for 5 mins at room temperature. TMAD (100 mM, N,N,N',N'-Tetramethylazodicarboxamide, Sigma Aldrich-D3648) was then added and the experimental pre-mix was left for a further 5 mins at room temperature.

The experimental pre-mix was then used for nanopore experiments. Electrical measurements were acquired at 20-45° C. from single MspA nanopores inserted in block co-polymer in buffer (600 mM KCl, 25 mM K Phosphate buffer, 75 mM Potassium Ferrocyanide (II), 25 mM Potassium Ferricyanide (III), pH 8). After achieving a single pore inserted in the block co-polymer, then buffer (3 mL, 960 mM KCl, 3 mM Potassium Ferrocyanide (II), 1 mM Potassium ferricyanide (III), 25 mM potassium phosphate pH 8) was flowed through the system to remove any excess MspA nanopores. $MgCl_2$ (1 mM final concentration) and ATP (2 mM final concentration, Sigma Aldrich-A6559-25UMO) were mixed together with buffer (500 mM KCl, 25 mM potassium phosphate pH 8) and then added to the modified DNA construct experimental pre-mix. 150 ul of the pre-mix was then added to the nanopore experimental system. Experiments were carried out for six hours, at 140 mV, and helicase-controlled DNA movement was monitored.

Helicase controlled DNA movements were individually base-called and then all movement reads were used to create a consensus. A consensus was created by first aligning the movement reads to a reference sequence using standard genome scale alignment software. At each alignment position a naïve maximum frequency consensus was formed. Where the data indicated a deletion or insertion with respect to the reference sequence, these were retained in the consensus. The consensus sequence was then itself aligned to the reference sequence. The allele frequencies of the movement reads across alignment positions, and the consensus sequence were inspected with the visualisation software IGV.

Results and Discussion

Helicase controlled DNA movement was observed for the modified random lambda DNA construct tested, where during synthesis all the A's in the sequences were replaced with 2'-Fluoro-2'-deoxyadenosine-5'-triphosphate.

Figure 18:
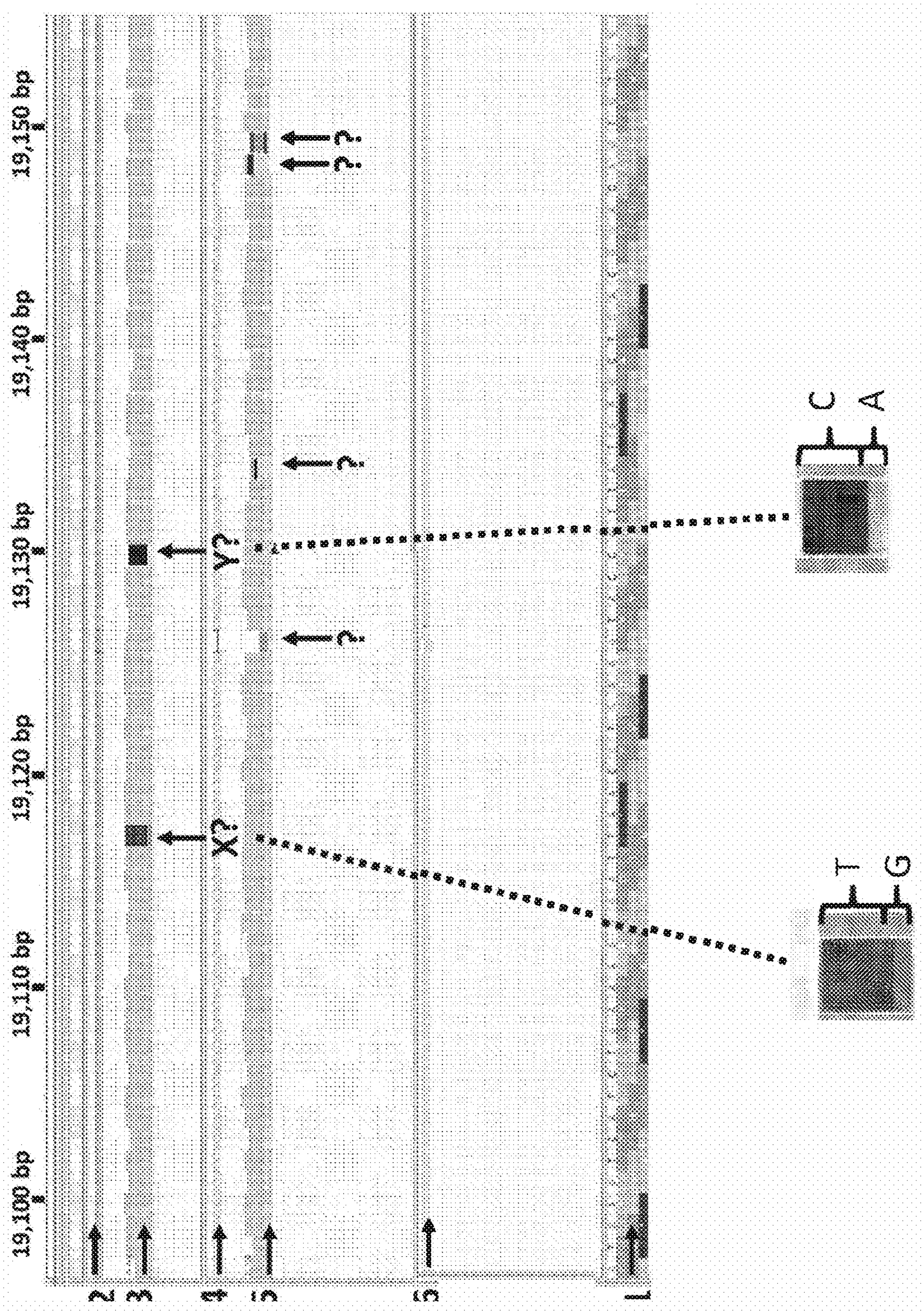
FIG. 18 shows a pictorial representation of a region of the lambda genomic DNA sequence (19,100 bp-19,150 bp) alignment. The reference sequence is shown in line 1. The consensus sequence when the DNA template was copied using A) 2'-deoxyadenosine-5'-triphosphate, 2'-deoxyguanosine-5'-triphosphate, 2'-deoxythymine-5'-triphosphate, 2'-deoxycytosine-5'-triphosphate is shown at line 4 and the corresponding allele frequencies at line 5. The consensus sequence when the DNA template was copied using B) 2'-fluoro-2'-deoxyadenosine-5'-triphosphate, 2'-deoxyguanosine-5'-triphosphate, 2'-deoxythymine-5'-triphosphate, 2'-deoxycytosine-5'-triphosphate is shown at line 2 and the corresponding allele frequencies at line 3. Line 6 corresponds to when the data for both strands (made by polymerisation of the template using A or B bases) have been combined. The arrows with the '?' show positions for which the consensus sequence is ambiguous; it was not possible to form a consensus with a confidence greater than 80%. When line 3 and 5 were compared the positions for which it was not possible to form a consensus with a confidence of 80% or greater occurred at different positions in the sequence. When the data were combined (line 6) a correct consensus sequence could be formed. In order to aid in the understanding of the figure, two of the regions marked with an arrow with 'X?' or 'Y?' have been expanded and are shown below the main figure. For 'X?' the position was called as a T in around 65% of the helicase controlled DNA movements analysed (of the strand made of B bases) but as a G in around 35% of the helicase controlled DNA movements analysed (of the strand made of B bases). For 'Y?' the position was called as a C in around 65% of the helicase controlled DNA movements analysed (of the strand made of B bases) but as an A in around 35% of the helicase controlled DNA movements analysed (of the strand made of B bases). For each arrow '?' position the allele frequencies are shaded different shades of grey corresponding to which base is called at that position.
Figure 21:
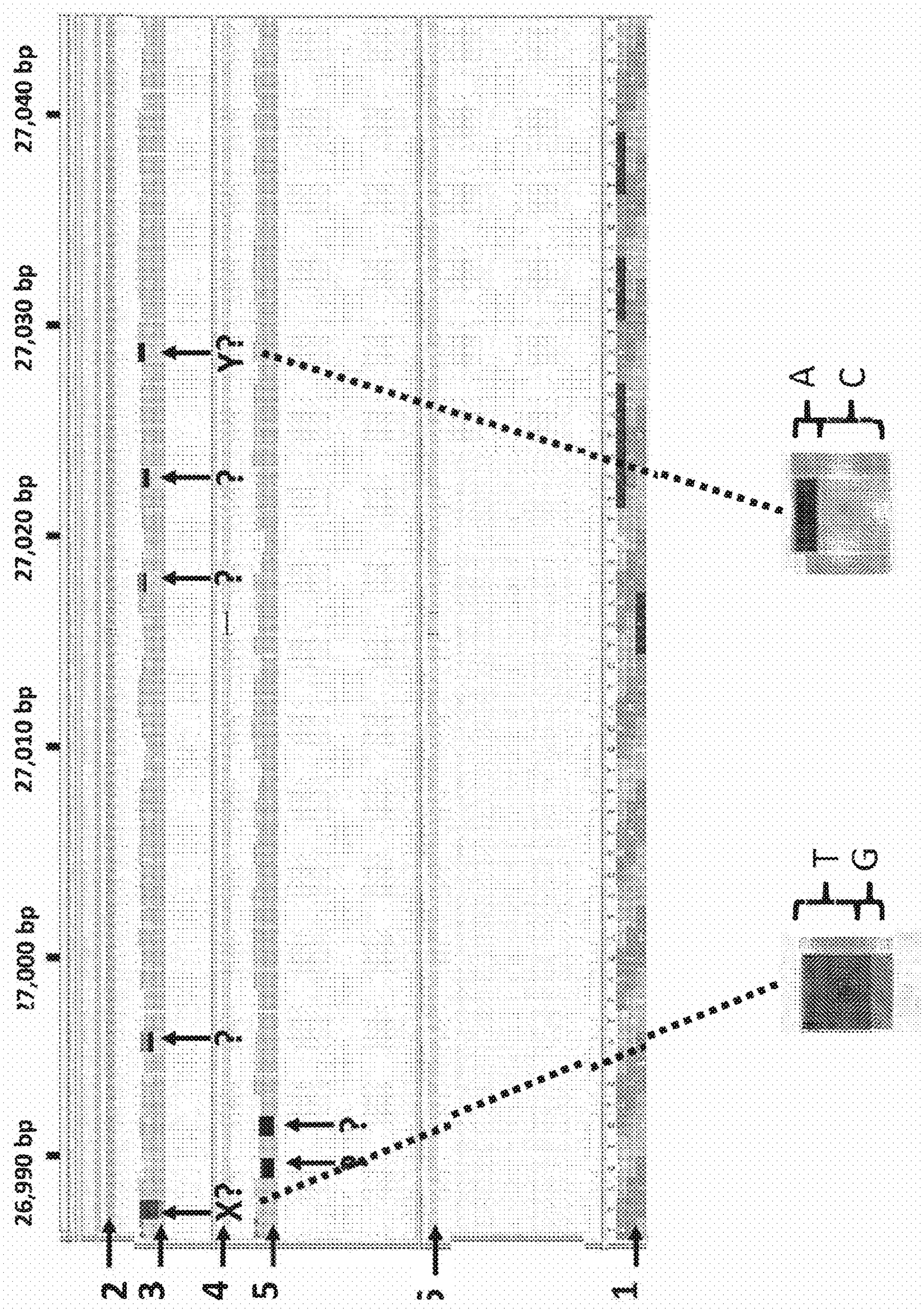
FIG. 21 shows a pictorial representation of a region of the lambda genomic DNA sequence (26,990-27,040 bp) alignment. The reference sequence is shown in line 1. The consensus sequence when the DNA template was copied using A) 2'-deoxyadenosine-5'-triphosphate, 2'-deoxyguanosine-5'-triphosphate, 2'-deoxythymine-5'-triphosphate, 2'-deoxycytosine-5'-triphosphate is shown at line 4 and the corresponding allele frequencies at line 5. The consensus sequence when the DNA template was copied using B) 2'-fluoro-2'-deoxyadenosine-5'-triphosphate, 2'-deoxyguanosine-5'-triphosphate, 2'-deoxythymine-5'-triphosphate, 2'-deoxycytosine-5'-triphosphate is shown at line 2 and the corresponding allele frequencies at line 3. Line 6 corresponds to when the data for both strands (made by polymerisation of the template using A or B bases) has been combined. The arrows with the '?' show positions for which the consensus sequence is ambiguous; it was not possible to form a consensus with a confidence greater than 80%. When line 3 and 5 were compared the positions for which it was not possible to form a consensus with a confidence of 80% or greater occurred at different positions in the sequence. When the data were combined (line 6) a correct consensus sequence could be formed. In order to aid in the understanding of the figure, two of the regions which are marked with an arrow with 'X?' or 'Y?' have been expanded and are shown below the main figure. For 'X?' the position was called as a T in around 65% of the helicase controlled DNA movements analysed (of the strand made of B bases) but as a G in around 35% of the helicase controlled DNA movements analysed (of the strand made of B bases). For 'Y?' the position was called as an A in around 65% of the helicase controlled DNA movements analysed (of the strand made of B bases) but as a C in around 35% of the helicase controlled DNA movements analysed (of the strand made of B bases). For each arrow '?' position the allele frequencies are shaded different shades of grey corresponding to which base is called at that position.

The alignments shown in FIGS. 18 and 21 display zoomed in regions of the lambda genomic DNA sequence alignment. Each figure shows the alignment along with the consensus, using the lambda genomic sequence as a reference (line 1 for all figures), for the DNA made with either A) 2'-deoxyadenosine-5'-triphosphate, 2'-deoxyguanosine-5'-triphosphate, 2'-deoxythymine-5'-triphosphate, 2'-deoxycytosine-5'-triphosphate (consensus=line 4 and allele frequencies=line 5 for all figures) or B) 2'-fluoro-2'-deoxyadenosine-5'-triphosphate, 2'-deoxyguanosine-5'-triphosphate, 2'-deoxythymine-5'-triphosphate, 2'-deoxycytosine-5'-triphosphate (consensus=line 2 and allele frequencies=line 3 for all figures). Any ambiguities in the consensus sequence for a specific base at a specific site or position can be seen for each of the templates (marked with arrows with '?' in all figures). This example illustrates that for both alignments the ambiguities in the consensus sequence for a specific base site or position when compared to the reference occur at different points in the sequence for DNA templates made from either (A) or (B) bases. It was possible to increase the probability of resolving the ambiguity in the consensus sequence, when both sets of data were combined (line 6 shows no arrows '?'). The specific sites or positions in the sequence where it was not possible to form a consensus with a confidence of greater than 80% would have remained unresolved for either A or B combination of bases had the data from both experiments not been combined. It was also possible to increase the probability of resolving ambiguities in deletions and insertions in the consensus sequence, when both sets of data were combined.

The invention claimed is:

1. A method of characterising a homopolynucleotide consisting of contiguous nucleotides of a single nucleotide species, comprising:

a) contacting the homopolynucleotide with a polymerase and a population of free nucleotides under conditions in which the polymerase forms a modified polynucleotide using the homopolynucleotide as a template for synthesizing the modified polynucleotide, wherein the population of free nucleotides comprises a first modified nucleotide that is not the same as the nucleotide species that is complementary to the single nucleotide species of the homopolynucleotide, and a second modified nucleotide that is not the same as the nucleotide species that is complementary to the single nucleotide species of the homopolynucleotide or the first modified nucleotide, wherein forming the modified polynucleotide comprises using the polymerase to replace nucleotides of the nucleotide species that is complementary to the single nucleotide species of the homopolynucleotide with (i) the first modified nucleotide, or (ii) the second modified nucleotide, such that the modified polynucleotide comprises at least one of (i) and at least one of (ii);

b) contacting the modified polynucleotide with a transmembrane pore in the presence of an electrical potential across the transmembrane pore, such that the modified polynucleotide moves through the pore; and c) taking one or more electrical measurements as the modified polynucleotide moves through the pore wherein the measurements are indicative of one or more characteristics of the modified polynucleotide and thereby characterising the homopolynucleotide.

2. A method according to claim 1, wherein forming the modified polynucleotide comprises using the polymerase to replace each nucleotide of the nucleotide species that is complementary to the single nucleotide species of the homopolynucleotide with either the first modified nucleotide or the second modified nucleotide.

3. A method according to claim 1, wherein the single nucleotide species of the homopolynucleotide is selected from AMP, dAMP, CMP, dCMP, GMP, dGMP, TMP, dTMP, UMP, and dUMP.

4. A method according to claim 3, wherein the first and second modified nucleotides independently are modified versions of the nucleotide species that the first and second modified nucleotides are replacing.

5. A method according to claim 4, wherein the first and second modified nucleotides independently comprise a chemical group or atom absent from the nucleotide species that the first and second modified nucleotides are replacing.

6. A method according to claim 5, wherein the chemical group is a propynyl group, a thio group, an oxo group, a methyl group, a hydroxymethyl group, a formyl group, a carboxy group, a carbonyl group, a benzyl group, a propargyl group or a propargylamine group.

7. A method according to claim 4, wherein the first and second modified nucleotides independently lack a chemical group or atom present in the nucleotide species that the first and second modified nucleotides are replacing.

8. A method according to claim 1, wherein the first and second modified nucleotides independently have an altered electronegativity compared with the nucleotide species that the first and second modified nucleotides are replacing.

9. A method according to claim 8, wherein the first and second modified nucleotides having the altered electronegativity comprise a halogen atom.

10. A method according to claim 1, wherein the homopolynucleotide is from 5 to 50 contiguous nucleotides in length.

11. A method according to claim 1, wherein the homopolynucleotide forms part of a longer template polynucleotide.

12. A method according to claim 1, wherein the first and second modified nucleotides in the modified polynucleotide comprise a nucleobase which differs from adenine, guanine, uracil, thymine, cytosine or methylcytosine and/or comprises a nucleoside which differs from adenosine, guanosine, uridine, cytidine or methylcytidine, deoxyadenosine, deoxyguanosine, thymidine, deoxycytidine or deoxymethylcytidine.

13. A method according to claim 12, wherein the first and second modified nucleotides independently comprise hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring).

14. A method according to claim 13, wherein the first and second modified nucleotides independently comprise 2'-deoxyinosine, inosine, 7-deaza-2'-deoxyinosine, 7-deaza-inosine, 2-aza-deoxyinosine, 2-aza-inosine, 2-0'-methylinosine, 4-nitroindole 2'-deoxyribonucleoside, 4-nitroindole ribonucleoside, 5-nitroindole 2' deoxyribonucleoside, 5-nitroindole ribonucleoside, 6-nitroindole 2' deoxyribonucleoside, 6-nitroindole ribonucleoside, 3-nitropyrrole 2' deoxyribonucleoside, 3-nitropyrrole ribonucleoside, an acyclic sugar analogue of hypoxanthine, nitroimidazole 2' deoxyribonucleoside, nitroimidazole ribonucleoside, 4-nitropyrazole 2' deoxyribonucleoside, 4-nitropyrazole ribonucleoside, 4-nitrobenzimidazole 2' deoxyribonucleoside, 4-nitrobenzimidazole ribonucleoside, 5-nitroindazole 2' deoxyribonucleoside, 5-nitroindazole ribonucleoside, 4-aminobenzimidazole 2' deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine.

15. A method according to claim 1, wherein step (b) further comprises contacting the modified polynucleotide with a polynucleotide binding protein such that the protein controls the movement of the modified polynucleotide through the pore.

16. A method according to claim 15, wherein the method comprises (b) contacting the modified polynucleotide with a transmembrane pore and a polynucleotide binding protein such that the polynucleotide moves through the pore and the protein controls the movement of the modified polynucleotide through the pore; and (c) measuring the current passing through the pore as the modified polynucleotide moves with respect to the pore wherein the current is indicative of one or more characteristics of the modified polynucleotide and thereby characterising the homopolynucleotide.

17. A method according to claim 15, wherein the polynucleotide binding protein is derived from a helicase.

* * * * *

SEQUENCE LISTING

```
Sequence total quantity: 49
SEQ ID NO: 1            moltype = DNA  length = 558
FEATURE                 Location/Qualifiers
misc_feature            1..558
                        note = Mycobacterium smegmatis porin A mutant
                         (D90N/D91N/D93N/D118R/D134R/E193K)
source                  1..558
                        mol_type = other DNA
                        organism = synthetic construct
SEQUENCE: 1
atgggtctgg ataatgaact gagcctggtg gacggtcaag atcgtaccct gacggtgcaa  60
caatgggata cctttctgaa tggcgttttt ccgctggatc gtaatcgcct gacccgtgaa  120
tggtttcatt ccggtcgcgc aaaatatatc gtcgcaggcc cgggtgctga cgaattcgaa  180
ggcacgctgg aactgggtta tcagattggc tttccgtggt cactgggcgt tggtatcaac  240
ttctcgtaca ccacgccgaa tattctgatc aacaatggta acattaccgc accgccgttt  300
ggcctgaaca gcgtgattac gccgaacctg tttccgggtg ttagcatctc tgcccgtctg  360
ggcaatggtc cgggcattca agaagtggca acctttagtg tgcgcgtttc cggcgctaaa  420
ggcggtgtcg cggtgtctaa cgcccacggt accgttacgg gcgcggccgg cggtgtcctg  480
ctgcgtccgt tcgcgcgcct gattgcctct accggcgaca gcgttacgac ctatggcgaa  540
ccgtggaata tgaactaa                                                558

SEQ ID NO: 2            moltype = AA  length = 184
FEATURE                 Location/Qualifiers
REGION                  1..184
                        note = Mycobacterium smegmatis porin A mutant
                         (D90N/D91N/D93N/D118R/D134R/E139K)
source                  1..184
                        mol_type = protein
                        organism = synthetic construct
SEQUENCE: 2
GLDNELSLVD GQDRTLTVQQ WDTFLNGVFP LDRNRLTREW FHSGRAKYIV AGPGADEFEG  60
TLELGYQIGF PWSLGVGINF SYTTPNILIN NGNITAPPFG LNSVITPNLF PGVSISARLG  120
NGPGIQEVAT FSVRVSGAKG GVAVSNAHGT VTGAAGGVLL RPFARLIAST GDSVTTYGEP  180
WNMN                                                               184

SEQ ID NO: 3            moltype = DNA  length = 885
FEATURE                 Location/Qualifiers
misc_feature            1..885
                        note = alpha-hemolysin mutant (E111N/K147N)
source                  1..885
                        mol_type = other DNA
                        organism = synthetic construct
SEQUENCE: 3
atggcagatt ctgatattaa tattaaaacc ggtactacag atattggaag caatactaca  60
gtaaaaacag gtgatttagt cacttatgat aaagaaaatg gcatgcacaa aaaagtattt  120
tatagtttta tcgatgataa aaatcacaat aaaaaactgc tagttattag aacaaaaggt  180
accattgctg gtcaatatag agtttatagc gaagaaggtg ctaacaaaag tggtttagcc  240
tggccttcag cctttaaggt acagttgcaa ctacctgata atgaagtagc tcaaatatct  300
gattactatc caagaaattc gattgataca aaaaactata tgagtacttt aacttatgga  360
ttcaacggta atgttactgg tgatgataca ggaaaaattg gcggccttat tggtgcaaat  420
gtttcgattg gtcatacact gaactatgtt caacctgatt tcaaaacaat tttagagagc  480
ccaactgata aaaaagtagg ctggaaagtg atatttaaca atatggtgaa tcaaaattgg  540
ggaccatacg atcgagattc ttggaacccg gtatatggca atcaactttt catgaaaact  600
agaaatggtt ctatgaaagc agcagataac ttccttgatc ctaacaaagc aagttctcta  660
ttatcttcag ggttttcacc agacttcgct acagttatta ctatggatag aaaagcatcc  720
aaacaacaaa caaatataga tgtaatatac gaacgagttc gtgatgatta ccaattgcat  780
tggacttcaa caaattggaa aggtaccaat actaaagata aatggacaga tcgttcttca  840
gaaagatata aaatcgattg ggaaaaagaa gaaatgacaa attaa                  885

SEQ ID NO: 4            moltype = AA  length = 293
FEATURE                 Location/Qualifiers
REGION                  1..293
                        note = alpha-hemolysin mutant (E111N/K147N)
source                  1..293
                        mol_type = protein
                        organism = synthetic construct
SEQUENCE: 4
ADSDINIKTG TTDIGSNTTV KTGDLVTYDK ENGMHKKVFY SFIDDKNHNK KLLVIRTKGT  60
IAGQYRVYSE EGANKSGLAW PSAFKVQLQL PDNEVAQISD YYPRNSIDTK NYMSTLTYGF  120
NGNVTGDDTG KIGGLIGANV SIGHTLNYVQ PDFKTILESP TDKKVGWKVI FNNMVNQNWG  180
PYDRDSWNPV YGNQLFMKTR NGSMKAADNF LDPNKASSLL SSGFSPDFAT VITMDRKASK  240
QQTNIDVIYE RVRDDYQLHW TSTNWKGTNT KDKWTDRSSE RYKIDWEKEE MTN         293

SEQ ID NO: 5            moltype = AA  length = 184
FEATURE                 Location/Qualifiers
source                  1..184
                        mol_type = protein
                        organism = Mycobacterium smegmatis
```

```
SEQUENCE: 5
GLDNELSLVD GQDRTLTVQQ WDTFLNGVFP LDRNRLTREW FHSGRAKYIV AGPGADEFEG  60
TLELGYQIGF PWSLGVGINF SYTTPNILID DGDITAPPFG LNSVITPNLF PGVSISADLG  120
NGPGIQEVAT FSVDVSGPAG GVAVSNAHGT VTGAAGGVLL RPFARLIAST GDSVTTYGEP  180
WNMN                                                              184

SEQ ID NO: 6           moltype = AA  length = 184
FEATURE                Location/Qualifiers
source                 1..184
                       mol_type = protein
                       organism = Mycobacterium smegmatis
SEQUENCE: 6
GLDNELSLVD GQDRTLTVQQ WDTFLNGVFP LDRNRLTREW FHSGRAKYIV AGPGADEFEG  60
TLELGYQIGF PWSLGVGINF SYTTPNILID DGDITGPPFG LESVITPNLF PGVSISADLG  120
NGPGIQEVAT FSVDVSGPAG GVAVSNAHGT VTGAAGGVLL RPFARLIAST GDSVTTYGEP  180
WNMN                                                              184

SEQ ID NO: 7           moltype = AA  length = 183
FEATURE                Location/Qualifiers
source                 1..183
                       mol_type = protein
                       organism = Mycobacterium smegmatis
SEQUENCE: 7
VDNQLSVVDG QGRTLTVQQA ETFLNGVFPL DRNRLTREWF HSGRATYHVA GPGADEFEGT  60
LELGYQVGFP WSLGVGINFS YTTPNILIDG GDITQPPFGL DTIITPNLFP GVSISADLGN  120
GPGIQEVATF SVDVKGAKGA VAVSNAHGTV TGAAGGVLLR PFARLIASTG DSVTTYGEPW  180
NMN                                                               183

SEQ ID NO: 8           moltype = DNA  length = 1830
FEATURE                Location/Qualifiers
source                 1..1830
                       mol_type = genomic DNA
                       note = Bacillus subtilis phage phi29
                       organism = unidentified
SEQUENCE: 8
atgaaacaca tgccgcgtaa aatgtatagc tgcgcgtttg aaaccacgac caaagtggaa  60
gattgtcgcg tttgggccta tggctacatg aacatcgaag atcattctga atacaaaatc  120
ggtaacagtc tggatgaatt tatggcatgg gtgctgaaag ttcaggcgga tctgtacttc  180
cacaacctga aatttgatgg cgcattcatt atcaactggc tggaacgtaa tggctttaaa  240
tggagcgcgg atggtctgcc gaacacgtat aataccatta tctctcgtat gggccagtgg  300
tatatgattg atatctgcct gggctacaaa ggtaaacgca aaattcatac cgtgatctat  360
gatagcctga aaaaactgcc gtttccggtg aagaaaattg cgaaagattt caaactgacg  420
gttctgaaag gcgatattga ttatcacaaa gaacgtccgg ttggttacaa aatcaccccg  480
gaagaatacg catacatcaa aaacgatatc cagatcatcg cagaagcgct gctgattcag  540
tttaaacagg gcctggatcg catgaccgcg ggcagtgata gcctgaaagg tttcaaagat  600
atcatcacga ccaaaaaatt caaaaaagtg ttcccgacgc tgagcctggg tctggataaa  660
gaagttcgtt atgcctaccg cggcggtttt acctggctga acgatcgttt caaagaaaaa  720
gaaattggcg agggtatggt gtttgatgtt aatagtctgt atccggcaca gatgtacagc  780
cgcctgctgc cgtatggcga accgatcgtg ttcgagggta aatatgtttg ggatgaagat  840
tacccgctgc atattcagca catccgttgt gaatttgaac tgaaagaagg ctatattccg  900
accattcaga tcaaacgtag tcgcttctat aagggtaacg aatacctgaa aagctctggc  960
ggtgaaatcg cggatctgtg gctgagtaac gtggatctgg aactgatgaa agaacactac  1020
gatctgtaca acgttgaata catcagcggc ctgaaattta aagccacgac cggtctgttc  1080
aaagatttca tcgataaatg gacctacatc aaaacgacct ctgaaggcgc gattaaacag  1140
ctggccaaac tgatgctgaa cagcctgtat ggcaaattcg cctctaatcc ggatgtgacc  1200
ggtaaagttc cgtacctgaa agaaaatggc gcactgggtt ttcgcctggg cgaagaagaa  1260
acgaaagatc cggtgtatac cccgatgggt gttttcatta cggcctgggc acgttacacg  1320
accatcaccg cggcccaggc atgctatgat cgcattatct actgtgatac cgattctatt  1380
catctgacgg gcaccgaaat cccggatgtg attaaagata tcgttgatcc gaaaaaactg  1440
ggttattggg cccacgaaag tacgtttaaa cgtgcaaaat acctgcgcca gaaaacctac  1500
atccaggata tctacatgaa agaagtggat ggcaaactgg ttgaaggttc tccggatgat  1560
tacaccgata tcaaattcag tgtgaaatgc gccggcatga cggataaaat caaaaaagaa  1620
gtgaccttcg aaaacttcaa agttggtttc agccgcaaaa tgaaaccgaa accggtgcag  1680
gttccgggcg gtgtggttct ggtggatgat acgtttacca ttaaatctgg cggtagtgcg  1740
tggagccatc cgcagttcga aaaaggcggt ggctctggtg gcggttctgg cggtagtgcc  1800
tggagccacc cgcagtttga aaaataataa                                  1830

SEQ ID NO: 9           moltype = AA  length = 608
FEATURE                Location/Qualifiers
source                 1..608
                       mol_type = protein
                       note = Bacillus subtilis phage phi29
                       organism = unidentified
SEQUENCE: 9
MKHMPRKMYS CAFETTTKVE DCRVWAYGYM NIEDHSEYKI GNSLDEFMAW VLKVQADLYF  60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAEALLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
```

-continued

```
TIQIKRSRFY KGNEYLKSSG GEIADLWLSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RAKYLRQKTY IQDIYMKEVD GKLVEGSPDD YTDIKFSVKC AGMTDKIKKE  540
VTFENFKVGF SRKMKPKPVQ VPGGVVLVDD TFTIKSGGSA WSHPQFEKGG GSGGGSGGSA  600
WSHPQFEK                                                          608

SEQ ID NO: 10          moltype = DNA  length = 1390
FEATURE                Location/Qualifiers
source                 1..1390
                       mol_type = genomic DNA
                       organism = Escherichia coli
SEQUENCE: 10
atgatgaacg atggcaaaca gcagagcacc ttcctgtttc atgattatga aaccttcggt  60
acccatccgg ccctggatcg tccggcgcag tttgcggcca ttcgcaccga tagcgaattc  120
aatgtgattg gcgaaccgga agtgttttat tgcaaaccgg ccgatgatta tctgccgcag  180
ccgggtgcgg tgctgattac cggtattacc ccgcaggaag cgcgcgcgaa aggtgaaaac  240
gaagcggcgt ttgccgcgcg cattcatagc ctgtttaccg tgccgaaaac ctgcattctg  300
ggctataaca atgtgcgctt cgatgatgaa gttacccgta atatctttta tcgtaacttt  360
tatgatccgt atgcgtggag ctggcagcat gataacagcc gttgggatct gctggatgtg  420
atgcgcgcgt gctatgcgct gcgcccggaa ggcattaatt ggccggaaaa cgatgatggc  480
ctgccgagct ttcgtctgga acatctgacc aaagccaacg gcattgaaca tagcaatgcc  540
catgatgcga tggccgatgt ttatgcgacc attgcgatgg cgaaactggt taaaacccgt  600
cagccgcgcc tgtttgatta tctgtttacc caccgtaaca aacacaaact gatggcgctg  660
attgatgttc cgcagatgaa accgctggtg catgtgagcg gcatgtttgg cgcctggcgc  720
ggcaacacca gctgggtggc cccgctggcc tggcacccgg aaaatcgtaa cgccgtgatt  780
atggttgatc tggccggtga tattagcccg ctgctggaac tggatagcga taccctgcgt  840
gaacgcctgt ataccgccaa aaccgatctg ggcgataatg ccgccgtgcc ggtgaaactg  900
gttcacatta acaaatgccc ggtgctggcc caggcgaaca ccctgcgccc ggaagatgcg  960
gatcgtctgg gtattaatcg ccagcattgt ctggataatc tgaaaatcct gcgtgaaaac  1020
ccgcaggtgc gtgaaaaagt ggtggcgatc ttcgcggaag cggaaccgtt caccccgagc  1080
gataacgtgg atgcgcagct gtataacggc ttctttagcg atgccgatcg cgcggcgatg  1140
aaaatcgttc tggaaaccga accgcgcaat ctgccggcgc tggatattac ctttgttgat  1200
aaacgtattg aaaaactgct gtttaattat cgtgcgcgca attttccggg taccctggat  1260
tatgccgaac agcagcgttg gctggaacat cgtcgtcagg ttttcacccc ggaatttctg  1320
cagggttatg cggatgaact gcagatgctg gttcagcagt atgccgatga taaagaaaaa  1380
gtggcgctgc                                                        1390

SEQ ID NO: 11          moltype = AA  length = 485
FEATURE                Location/Qualifiers
source                 1..485
                       mol_type = protein
                       organism = Escherichia coli
SEQUENCE: 11
MMNDGKQQST FLFHDYETFG THPALDRPAQ FAAIRTDSEF NVIGEPEVFY CKPADDYLPQ  60
PGAVLITGIT PQEARAKGEN EAAFAARIHS LFTVPKTCIL GYNNVRFDDE VTRNIFYRNF  120
YDPYAWSWQH DNSRWDLLDV MRACYALRPE GINWPENDDG LPSFRLEHLT KANGIEHSNA  180
HDAMADVYAT IAMAKLVKTR QPRLFDYLFT HRNKHKLMAL IDVPQMKPLV HVSGMFGAWR  240
GNTSWVAPLA WHPENRNAVI MVDLAGDISP LLELDSDTLR ERLYTAKTDL GDNAAVPVKL  300
VHINKCPVLA QANTLRPEDA DRLGINRQHC LDNLKILREN PQVREKVVAI FAEAEPFTPS  360
DNVDAQLYNG FFSDADRAAM KIVLETEPRN LPALDITFVD KRIEKLLFNY RARNFPGTLD  420
YAEQQRWLEH RRQVFTPEFL QGYADELQML VQQYADDKEK VALLKALWQY AEEIVSGSGH  480
HHHHH                                                             485

SEQ ID NO: 12          moltype = DNA  length = 804
FEATURE                Location/Qualifiers
source                 1..804
                       mol_type = genomic DNA
                       organism = Escherichia coli
SEQUENCE: 12
atgaaatttg tctcttttaa tatcaacggc ctgcgcgcca gacctcacca gcttgaagcc  60
atcgtcgaaa agcaccaacc ggatgtgatt ggcctgcagg agacaaaagt tcatgacgat  120
atgtttccgc tcgaagaggt ggcgaagctc ggctacaacg tgttttatca cgggcagaaa  180
ggccattatg gcgtggcgct gctgaccaaa gagacgccga ttgccgtgcg tcgcggcttt  240
cccggtgacg acgaagaggc gcagcggcgg attattatgg cggaaatccc ctcactgctg  300
ggtaatgtca ccgtgatcaa cggttacttc ccgcagggtg aaagccgcga ccatccgata  360
aaattcccgg caaaagcgca gttttatcag aatctgcaaa actacctgga aaccgaactc  420
aaacgtgata atccggtact gattatgggc gatatgaata tcagccctac agatctggat  480
atcggcattg gcgaagaaaa ccgtaagcgc tggctgcgta ccggtaaatg ctctttcctg  540
ccggaagagc gcgaatggat ggacaggctg atgagctggg ggttggtcga taccttccgc  600
catgcgaatc cgcaaacagc agatcgtttc tcatggtttg attaccgctc aaaaggtttt  660
gacgataacc gtggtctgcg catcgacctg ctgctcgcca gccaaccgct ggcagaatgt  720
tgcgtagaaa ccggcatcga ctatgaaatc cgcagcatgg aaaaaccgtc cgatcacgcc  780
cccgtctggg cgaccttccg ccgc                                        804

SEQ ID NO: 13          moltype = AA  length = 268
FEATURE                Location/Qualifiers
```

-continued

```
source                  1..268
                        mol_type = protein
                        organism = Escherichia coli
SEQUENCE: 13
MKFVSFNING LRARPHQLEA IVEKHQPDVI GLQETKVHDD MFPLEEVAKL GYNVFYHGQK  60
GHYGVALLTK ETPIAVRRGF PGDDEEAQRR IIMAEIPSLL GNVTVINGYF PQGESRDHPI  120
KFPAKAQFYQ NLQNYLETEL KRDNPVLIMG DMNISPTDLD IGIGEENRKR WLRTGKCSFL  180
PEEREWMDRL MSWGLVDTFR HANPQTADRF SWFDYRSKGF DDNRGLRIDL LLASQPLAEC  240
CVETGIDYEI RSMEKPSDHA PVWATFRR                                     268

SEQ ID NO: 14           moltype = DNA  length = 1275
FEATURE                 Location/Qualifiers
source                  1..1275
                        mol_type = genomic DNA
                        organism = Thermus thermophilus
SEQUENCE: 14
atgtttcgtc gtaaagaaga tctggatccg ccgctggcac tgctgccgct gaaaggcctg  60
cgcgaagccg ccgcactgct ggaagaagcg ctgcgtcaag gtaaacgcat tcgtgttcac  120
ggcgactatg atgcggatgg cctgaccggc accgcgatcc tggttcgtgg tctggccgcc  180
ctgggtgcgg atgttcatcc gtttatcccg caccgcctgg aagaaggcta tggtgtcctg  240
atggaacgcg tcccggaaca tctggaagcc tcggacctgt ttctgaccgt tgactgcggc  300
attaccaacc atgcggaact gcgcgaactg ctggaaaatg gcgtggaagt cattgttacc  360
gatcatcata cgccgggcaa aacgccgccg ccgggtctgg tcgtgcatcc ggcgctgacg  420
ccggatctga aagaaaaacc gaccggcgca ggcgtggcgt ttctgctgct gtgggcactg  480
catgaacgcc tgggcctgcc gccgccgctg gaatacgcgg acctggcagc cgttggcacc  540
attgccgacg ttgccccgct gtggggttgg aatcgtgcac tggtgaaaga aggtctggca  600
cgcatcccgg cttcatcttg ggtgggcctg cgtctgctgg ctgaagccgt gggctatacc  660
ggcaaagcgg tcgaagtcgc tttccgcatc gcgccgcgca tcaatgcggc ttcccgcctg  720
ggcgaagcgg aaaaagccct gcgcctgctg ctgacggatg atgcggcaga agctcaggcg  780
ctggtcggcg aactgcaccg tctgaacgcc cgtcgtcaga ccctggaaga agcgatgctg  840
cgcaaactgc tgccgcaggc cgacccggaa gcgaaagcca tcgttctgct ggacccggaa  900
ggccatccgg gtgttatggg tattgtggcc tctcgcatcc tggaagcgac cctgcgcccg  960
gtctttctgg tggcccaggg caaaggcacc gtgcgttcgc tggctccgat ttccgccgtc  1020
gaagcactgc gcagcgcgga agatctgctg ctgcgttatg gtggtcataa agaagcggcg  1080
ggtttcgcaa tggatgaagc gctgtttccg gcgttcaaag cacgcgttga agcgtatgcc  1140
gcacgtttcc cggatccggt tcgtgaagtg gcactgctgg atctgctgcc ggaaccgggc  1200
ctgctgccgc aggtgttccg tgaactggca ctgctggaac cgtatggtga aggtaacccg  1260
gaaccgctgt tcctg                                                  1275

SEQ ID NO: 15           moltype = AA  length = 425
FEATURE                 Location/Qualifiers
source                  1..425
                        mol_type = protein
                        organism = Thermus thermophilus
SEQUENCE: 15
MFRRKEDLDP PLALLPLKGL REAAALLEEA LRQGKRIRVH GDYDADGLTG TAILVRGLAA  60
LGADVHPFIP HRLEEGYGVL MERVPEHLEA SDLFLTVDCG ITNHAELREL LENGVEVIVT  120
DHHTPGKTPP PGLVVHPALT PDLKEKPTGA GVAFLLLWAL HERLGLPPPL EYADLAAVGT  180
IADVAPLWGW NRALVKEGLA RIPASSWVGL RLLAEAVGYT GKAVEVAFRI APRINAASRL  240
GEAEKALRLL LTDDAAEAQA LVGELHRLNA RRQTLEEAML RKLLPQADPE AKAIVLLDPE  300
GHPGVMGIVA SRILEATLRP VFLVAQGKGT VRSLAPISAV EALRSAEDLL LRYGGHKEAA  360
GFAMDEALFP AFKARVEAYA ARFPDPVREV ALLDLLPEPG LLPQVFRELA LLEPYGEGNP  420
EPLFL                                                              425

SEQ ID NO: 16           moltype = DNA  length = 738
FEATURE                 Location/Qualifiers
source                  1..738
                        mol_type = other DNA
                        note = Bacteriophage lambda
                        organism = unidentified
SEQUENCE: 16
tccggaagcg gctctggtag tggttctggc atgacaccgg acattatcct gcagcgtacc  60
gggatcgatg tgagagctgt cgaacagggg gatgatgcgt ggcacaaatt acggctcggc  120
gtcatcaccg cttcagaagt tcacaacgtg atagcaaaac cccgctccgg aaagaagtgg  180
cctgacatga aaatgtccta cttccacacc ctgcttgctg aggtttgcac cggtgtggct  240
ccggaagtta acgctaaagc actggcctgg ggaaaacagt acgagaacga cgccagaacc  300
ctgtttgaat tcacttccgg cgtgaatgtt actgaatccc cgatcatcta tcgcgacgaa  360
agtatgcgta ccgcctgctc tcccgatggt ttatgcagtg acggcaacgg ccttgaactg  420
aaatgcccgt ttacctcccg ggatttcatg aagttccggc tcggtggttt cgaggccata  480
aagtcagctt acatggccca ggtgcagtac agcatgtggg tgacgcgaaa aaatgcctgg  540
tactttgcca actatgaccc gcgtatgaag cgtgaaggcc tgcattatgt cgtgattgag  600
cgggatgaaa agtacatggc gagttttgac gagatcgtgc cggagttcat cgaaaaaatg  660
gacgaggcac tggctgaaat tggttttgta tttggggagc aatggcgatc tggctctggt  720
tccggcagcg gttccgga                                                738

SEQ ID NO: 17           moltype = AA  length = 226
FEATURE                 Location/Qualifiers
```

-continued

```
source                 1..226
                       mol_type = protein
                       note = Bacteriophage lambda
                       organism = unidentified
SEQUENCE: 17
MTPDIILQRT GIDVRAVEQG DDAWHKLRLG VITASEVHNV IAKPRSGKKW PDMKMSYFHT  60
LLAEVCTGVA PEVNAKALAW GKQYENDART LFEFTSGVNV TESPIIYRDE SMRTACSPDG  120
LCSDGNGLEL KCPFTSRDFM KFRLGGFEAI KSAYMAQVQY SMWVTRKNAW YFANYDPRMK  180
REGLHYVVIE RDEKYMASFD EIVPEFIEKM DEALAEIGFV FGEQWR                226

SEQ ID NO: 18          moltype = AA  length = 760
FEATURE                Location/Qualifiers
source                 1..760
                       mol_type = protein
                       organism = Methanococcoides burtonii
SEQUENCE: 18
MMIRELDIPR DIIGFYEDSG IKELYPPQAE AIEMGLLEKK NLLAAIPTAS GKTLLAELAM  60
IKAIREGGKA LYIVPLRALA SEKFERFKEL APFGIKVGIS TGDLDSRADW LGVNDIIVAT  120
SEKTDSLLRN GTSWMDEITT VVVDEIHLLD SKNRGPTLEV TITKLMRLNP DVQVVALSAT  180
VGNAREMADW LGAALVLSEW RPTDLHEGVL FGDAINFPGS QKKIDRLEKD DAVNLVLDTI  240
KAEGQCLVFE SSRRNCAGFA KTASSKVAKI LDNDIMIKLA GIAEEVESTG ETDTAIVLAN  300
CIRKGVAFHH AGLNSNHRKL VENGFRQNLI KVISSTPTLA AGLNLPARRV IIRSYRRFDS  360
NFGMQPIPVL EYKQMAGRAG RPHLDPYGES VLLAKTYDEF AQLMENYVEA DAEDIWSKLG  420
TENALRTHVL STIVNGFAST RQELFDFFGA TFFAYQQDKW MLEEVINDCL EFLIDKAMVS  480
ETEDIEDASK LFLRGTRLGS LVSMLYIDPL SGSKIVDGFK DIGKSTGGNM GSLEDDKGDD  540
ITVTDMTLLH LVCSTPDMRQ LYLRNTDYTI VNEYIVAHSD EFHEIPDKLK ETDYEWFMGE  600
VKTAMLLEEW VTEVSAEDIT RHFNVGEGDI HALADTSEWL MHAAAKLAEL LGVEYSSHAY  660
SLEKRIRYGS GLDLMELVGI RGVGRVRARK LYNAGFVSVA KLKGADISVL SKLVGPKVAY  720
NILSGIGVRV NDKHFNSAPI SSNTLDTLLD KNQKTFNDFQ                       760

SEQ ID NO: 19          moltype = AA  length = 707
FEATURE                Location/Qualifiers
source                 1..707
                       mol_type = protein
                       note = Cenarchaeum symbiosum
                       organism = unidentified
SEQUENCE: 19
MRISELDIPR PAIEFLEGEG YKKLYPPQAA AAKAGLTDGK SVLVSAPTAS GKTLIAAIAM  60
ISHLSRNRGK AVYLSPLRAL AAEKFAEFGK IGGIPLGRPV RVGVSTGDFE KAGRSLGNND  120
ILVLTNERMD SLIRRRPDWM DEVGLVIADE IHLIGDRSRG PTLEMVLTKL RGLRSSPQVV  180
ALSATISNAD EIAGWLDCTL VHSTWRPVPL SEGVYQDGEV AMGDGSRHEV AATGGGPAVD  240
LAAESVAEGG QSLIFADTRA RSASLAAKAS AVIPEAKGAD AAKLAAAAKK IISSGGETKL  300
AKTLAELVEK GAAFHHAGLN QDCRSVVEEE FRSGRIRLLA STPTLAAGVN LPARRVVISS  360
VMRYNSSSGM SEPISILEYK QLCGRAGRPQ YDKSGEAIVV GGVNADEIFD RYIGGEPEPI  420
RSAMVDDRAL RIHVLSLVTT SPGIKEDDVT EFFLGTLGGQ QSGESTVKFS VAVALRFLQE  480
EGMLGRRGGR LAATKMGRLV SRLYMDPMTA VTLRDAVGEA SPGRMHTLGF LHLVSECSEF  540
MPRFALRQKD HEVAEMMLEA GRGELLRPVY SYECGRGLLA LHRWIGESPE AKLAEDLKFE  600
SGDVHRMVES SGWLLRCIWE ISKHQERPDL LGELDVLRSR VAYGIKAELV PLVSIKGIGR  660
VRSRRLFRGG IKGPGDLAAV PVERLSRVEG IGATLANNIK SQLRKGG                707

SEQ ID NO: 20          moltype = AA  length = 720
FEATURE                Location/Qualifiers
source                 1..720
                       mol_type = protein
                       organism = Thermococcus gammatolerans
SEQUENCE: 20
MKVDELPVDE RLKAVLKERG IEELYPPQAE ALKSGALEGR NLVLAIPTAS GKTLVSEIVM  60
VNKLIQEGGK AVYLVPLKAL AEEKYREFKE WEKLGLKVAA TTGDYDSTDD WLGRYDIIVA  120
TAEKFDSLLR HGARWINDVK LVVADEVHLI GSYDRGATLE MILTHMLGRA QILALSATVG  180
NAEELAEWLD ASLVVSDWRP VQLRRGVFHL GTLIWEDGKV ESYPENWYSL VVDAVKRGKG  240
ALVFVNTRRS AEKEALALSK LVSSHLTKPE KRALESLASQ LEDNPTSEKL KRALRGGVAF  300
HHAGLSRVER TLIEDAFREG LIKVITATPT LSAGVNLPSF RVIIRDTKRY AGFGWTDIPV  360
LEIQQMMGRA GRPRYDKYGE AIIVARTDEP GKLMERYIRG KPEKLFSMLA NEQAFRSQVL  420
ALITNFGIRS FPELVRFLER TFYAHQRKDL SSLEYKAKEV VYFLIENEFI DLDLEDRFIP  480
LPFGKRTSQL YIDPLTAKKF KDAFPAIERN PNPFGIFQLI ASTPDMATLT ARRREMEDYL  540
DLAYELEDKL YASIPYYEDS RFQGFLGQVK TAKVLLDWIN EVPEARIYET YSIDPGDLYR  600
LLELADWLMY SLIELYKLFE PKEEILNYLR DLHLRLRHGV REELLELVRL PNIGRKRARA  660
LYNAGFRSVE AIANAKPAEL LAVEGIGAKI LDGIYRHLGI EKRVTEEKPK RKGTLEDFLR  720

SEQ ID NO: 21          moltype = AA  length = 799
FEATURE                Location/Qualifiers
source                 1..799
                       mol_type = protein
                       organism = Methanospirillum hungatei
SEQUENCE: 21
MEIASLPLPD SFIRACHAKG IRSLYPPQAE CIEKGLLEGK NLLISIPTAS GKTLLAEMAM  60
WSRIAAGGKC LYIVPLRALA SEKYDEFSKK GVIRVGIATG DLDRTDAYLG ENDIIVATSE  120
KTDSLLRNRT PWLSQITCIV LDEVHLIGSE NRGATLEMVI TKLRYTNPVM QIIGLSATIG  180
NPAQLAEWLD ATLITSTWRP VDLRQGVYYN GKIRFSDSER PIQGKTKHDD LNLCLDTIEE  240
```

```
GGQCLVFVSS RRNAEGFAKK AAGALKAGSP DSKALAQELR RLRDRDEGNV LADCVERGAA  300
FHHAGLIRQE RTIIEEGFRN GYIEVIAATP TLAAGLNLPA RRVIIRDYNR FASGLGMVPI  360
PVGEYHQMAG RAGRPHLDPY GEAVLLAKDA PSVERLFETF IDAEAERVDS QCVDDASLCA  420
HILSLIATGF AHDQEALSSF MERTFYFFQH PKTRSLPRLV ADAIRFLTTA GMVEERENTL  480
SATRLGSLVS RLYLNPCTAR LILDSLKSCK TPTLIGLLHV ICVSPDMQRL YLKAADTQLL  540
RTFLFKHKDD LILPLPFEQE EEELWLSGLK TALVLTDWAD EFSEGMIEER YGIGAGDLYN  600
IVDSGKWLLH GTERLVSVEM PEMSQVVKTL SVRVHHGVKS ELLPLVALRN IGRVRARTLY  660
NAGYPDPEAV ARAGLSTIAR IIGEGIARQV IDEITGVKRS GIHSSDDDYQ QKTPELLTDI  720
PGIGKKMAEK LQNAGIITVS DLLTADEVLL SDVLGAARAR KVLAFLSNSE KENSSSDKTE  780
EIPDTQKIRG QSSWEDFGC                                               799

SEQ ID NO: 22          moltype = AA  length = 1756
FEATURE                Location/Qualifiers
source                 1..1756
                       mol_type = protein
                       organism = Escherichia coli
SEQUENCE: 22
MMSIAQVRSA GSAGNYYTDK DNYYVLGSMG ERWAGKGAEQ LGLQGSVDKD VFTRLLEGRL  60
PDGADLSRMQ DGSNKHRPGY DLTFSAPKSV SMMAMLGGDK RLIDAHNQAV DFAVRQVEAL  120
ASTRVMTDGQ SETVLTGNLV MALFNHDTSR DQEPQLHTHA VVANVTQHNG EWKTLSSDKV  180
GKTGFIENVY ANQIAFGRLY REKLKEQVEA LGYETEVVGK HGMWEMPGVP VEAFSGRSQA  240
IREAVGEDAS LKSRDVAALD TRKSKQHVDP EIRMAEWMQT LKETGFDIRA YRDAADQRTE  300
IRTQAPGPAS QDGPDVQQAV TQAIAGLSER KVQFTYTDVL ARTVGILPPE NGVIERARAG  360
IDEAISREQL IPLDREKGLF TSGIHVLDEL SVRALSRDIM KQNRVTVHPE KSVPRTAGYS  420
DAVSVLAQDR PSLAIVSGQG GAAGQRERVA ELVMMAREQG REVQIIAADR RSQMNLKQDE  480
RLSGELITGR RQLLEGMAFT PGSTVIVDQG EKLSLKETLT LLDGAARHNV QVLITDSGQR  540
TGTGSALMAM KDAGVNTYRW QGGEQRPATI ISEPDRNVRY ARLAGDFAAS VKAGEESVAQ  600
VSGVREQAIL TQAIRSELKT QGVLGHPEVT MTALSPVWLD SRSRYLRDMY RPGMVMEQWN  660
PETRSHDRYV IDRVTAQSHS LTLRDAQGET QVVRISSLDS SWSLFRPEKM PVADGERLRV  720
TGKIPGLRVS GGDRLQVASV SEDAMTVVVP GRAEPASLPV SDSPFTALKL ENGWVETPGH  780
SVSDSATVFA SVTQMAMDNA TLNGLARSGR DVRLYSSLDE TRTAEKLARH PSFTVVSEQI  840
KARAGETLLE TAISLQKAGL HTPAQQAIHL ALPVLESKNL AFSMVDLLTE AKSFAAEGTG  900
FTELGGEINA QIKRGDLLYV DVAKGYGTGL LVSRASYEAE KSILRHILEG KEAVTPLMER  960
VPGELMETLT SGQRAATRMI LETSDRFTVV QGYAGVGKTT QFRAVMSAVN MLPASERPRV  1020
VGLGPTHRAV GEMRSAGVDA QTLASFLHDT QLQQRSGETP DFSNTLFLLD ESSMVGNTEM  1080
ARAYALIAAG GGRAVASGDT DQLQAIAPGQ SFRLQQTRSA ADVVIMKEIV RQTPELREAV  1140
YSLINRDVER ALSGLESVKP SQVPRLEGAW APEHSVTEFS HSQEAKLAEA QQKAMLKGEA  1200
FPDIPMTLYE AIVRDYTGRT PEAREQTLIV THLNEDRRVL NSMIHDAREK AGELGKEQVM  1260
VPVLNTANIR DGELRRLSTW EKNPDALALV DNVYHRIAGI SKDDGLITLQ DAEGNTRLIS  1320
PREAVAEGVT LYTPDKIRVG TGDRMRFTKS DRERGYVANS VWTVTAVSGD SVTLSDGQQT  1380
RVIRPGQERA EQHIDLAYAI TAHGAQGASE TFAIALEGTE GNRKLMAGFE SAYVALSRMK  1440
QHVQVYTDNR QGWTDAINNA VQKGTAHDVL EPKPDREVMN AQRLFSTARE LRDVAAGRAV  1500
LRQAGLAGGD SPARFIAPGR KYPQPYVALP AFDRNGKSAG IWLNPLTTDD GNGLRGFSGE  1560
GRVKGSGDAQ FVALQGSRNG ESLLADNMQD GVRIARDNPD SGVVVRIAGE GRPWNPGAIT  1620
GGRVWGDIPD NSVQPGAGNG EPVTAEVLAQ RQAEEAIRRE TERRADEIVR KMAENKPDLP  1680
DGKTELAVRD IAGQERDRSA ISERETALPE SVLRESQRER EAVREVAREN LLQERLQQME  1740
RDMVRDLQKE KTLGGD                                                  1756

SEQ ID NO: 23          moltype = AA  length = 726
FEATURE                Location/Qualifiers
source                 1..726
                       mol_type = protein
                       organism = Methanococcoides burtonii
SEQUENCE: 23
MSDKPAFMKY FTQSSCYPNQ QEAMDRIHSA LMQQQLVLFE GACGTGKTLS ALVPALHVGK  60
MLGKTVIIAT NVHQQMVQFI NEARDIKKVQ DVKVAVIKGK TAMCPQEADY EECSVKRENT  120
FELMETEREI YLKRQELNSA RDSYKKSHDP AFVTLRDELS KEIDAVEEKA RGLRDRACND  180
LYEVLRSDSE KFREWLYKEV RSPEEINDHA IKDGMCGYEL VKRELKHADL LICNYHHVLN  240
PDIFSTVLGW IEKEPQETIV IFDEAHNLES AARSHSSLSL TEHSIEKAIT ELEANLDLLA  300
DDNIHNLFNI FLEVISDTYN SRFKFGERER VRKNWYDIRI SDPYERNDIV RGKFLRQAKG  360
DFGEKDDIQI LLSEASELGA KLDETYRDQY KKGLSSVMKR SHIRYVADFM SAYIELSHNL  420
NYYPILNVRR DMNDEIYGRV ELFTCIPKNV TEPLFNSLFS VILMSATLHP FEMVKKTLGI  480
TRDTCEMSYG TSFPEEKRLS IAVSIPPLFA KNRDDRHVTE LLEQVLLDSI ENSKGNVILF  540
FQSAFEAKRY YSKIEPLVNV PVFLDEVGIS SQDVREEFFS IGEENGKAVL LSYLWGTLSE  600
GIDYRDGRGR TVIIIGVGYP ALNDRMNAVE SAYDHVFGYG AGWEFAIQVP TIRKIRQAMG  660
RVVRSPTDYG ARILLDGRFL TDSKKRFGKF SVFEVFPPAE RSEFVDVDPE KVKYSLMNFF  720
MDNDEQ                                                             726

SEQ ID NO: 24          moltype = AA  length = 439
FEATURE                Location/Qualifiers
source                 1..439
                       mol_type = protein
                       note = Enterobacteria phage T4
                       organism = unidentified
SEQUENCE: 24
MTFDDLTEGQ KNAFNIVMKA IKEKKHHVTI NGPAGTGKTT LTKFIIEALI STGETGIILA  60
APTHAAKKIL SKLSGKEAST IHSILKINPV TYEENVLFEQ KEVPDLAKCR VLICDEVSMY  120
DRKLFKILLS TIPPWCTIIG IGDNKQIRPV DPGENTAYIS PFFTHKDFYQ CELTEVKRSN  180
APIIDVATDV RNGKWIYDKV VDGHGVRGFT GDTALRDFMV NYFSIVKSLD DLFENRVMAF  240
```

-continued

```
TNKSVDKLNS IIRKKIFETD KDFIVGEIIV MQEPLFKTYK IDGKPVSEII FNNGQLVRII  300
EAEYTSTFVK ARGVPGEYLI RHWDLTVETY GDDEYYREKI KIISSDEELY KFNLFLGKTA  360
ETYKNWNKGG KAPWSDFWDA KSQFSKVKAL PASTFHKAQG MSVDRAFIYT PCIHYADVEL  420
AQQLLYVGVT RGRYDVFYV                                               439

SEQ ID NO: 25          moltype = AA  length = 970
FEATURE                Location/Qualifiers
source                 1..970
                       mol_type = protein
                       organism = Clostridium botulinum
SEQUENCE: 25
MLSVANVRSP SAAASYFASD NYYASADADR SGQWIGDGAK RLGLEGKVEA RAFDALLRGE  60
LPDGSSVGNP GQAHRPGTDL TFSVPKSWSL LALVGKDERI IAAYREAVVE ALHWAEKNAA  120
ETRVVEKGMV VTQATGNLAI GLFQHDTNRN QEPNLHFHAV IANVTQGKDG KWRTLKNDRL  180
WQLNTTLNSI AMARFRVAVE KLGYEPGPVL KHGNFEARGI SREQVMAFST RRKEVLEARR  240
GPGLDAGRIA ALDTRASKEG IEDRATLSKQ WSEAAQSIGL DLKPLVDRAR TKALGQGMEA  300
TRIGSLVERG RAWLSRFAAH VRGDPADPLV PPSVLKQDRQ TIAAAQAVAS AVRHLSQREA  360
AFERTALYKA ALDFGLPTTI ADVEKRTRAL VRSGDLIAGK GEHKGWLASR DAVVTEQRIL  420
SEVAAGKGDS SPAITPQKAA ASVQAAALTG QGFRLNEGQL AAARLILISK DRTIAVQGIA  480
GAGKSSVLKP VAEVLRDEGH PVIGLAIQNT LVQMLERDTG IGSQTLARFL GGWNKLLDDP  540
GNVALRAEAQ ASLKDHVLVL DEASMVSNED KEKLVRLANL AGVHRLVLIG DRKQLGAVDA  600
GKPFALLQRA GIARAEMATN LRARDPVVRE AQAAAQAGDV RKALRHLKSH TVEARGDGAQ  660
VAAETWLALD KETRARTSIY ASGRAIRSAV NAAVQQGLLA SREIGPAKMK LEVLDRVNTT  720
REELRHLPAY RAGRVLEVSR KQQALGLFIG EYRVIGQDRK GKLVEVEDKR GKRFRFDPAR  780
IRAGKGDDNL TLLEPRKLEI HEGDRIRWTR NDHRRGLFNA DQARVVEIAN GKVTFETSKG  840
DLVELKKDDP MLKRIDLAYA LNVHMAQGLT SDRGIAVMDS RERNLSNQKT FLVTVTRLRD  900
HLTLVVDSAD KLGAAVARNK GEKASAIEVT GSVKPTATKG SGVDQPKSVE ANKAEKELTR  960
SKSKTLDFGI                                                         970

SEQ ID NO: 26          moltype = AA  length = 605
FEATURE                Location/Qualifiers
source                 1..605
                       mol_type = protein
                       organism = Escherichia coli
SEQUENCE: 26
MISYDNYVTI LDEETLKAWI AKLEKAPVFA FDTETDSLDN ISANLVGLSF AIEPGVAAYI  60
PVAHDYLDAP DQISRERALE LLKPLLEDEK ALKVGQNLKY DRGILANYGI ELRGIAFDTM  120
LESYILNSVA GRHDMDSLAE RWLKHKTITF EEIAGKGKNQ LTFNQIALEE AGRYAAEDAD  180
VTLQLHLKMW PDLQKHKGPL NVFENIEMPL VPVLSRIERN GVKIDPKVLH NHSEELTLRL  240
AELEKKAHEI AGEEFNLSST KQLQTILFEK QGIKPLKKTP GGAPSTSEEV LEELALDYPL  300
PKVILEYRGL AKLKSTYTDK LPLMINPKTG RVHTSYHQAV TATGRLSSTD PNLQNIPVRN  360
EEGRRIRQAF IAPEDYVIVS ADYSQIELRI MAHLSRDKGL LTAFAEGKDI HRATAAEVFG  420
LPLETVTSEQ RRSAKAINFG LIYGMSAFGL ARQLNIPRKE AQKYMDLYFE RYPGVLEYME  480
RTRAQAKEQG YVETLDGRRL YLPDIKSSNG ARRAAAERAA INAPMQGTAA DIIKRAMIAV  540
DAWLQAEQPR VRMIMQVHDE LVFEVHKDDV DAVAKQIHQL MENCTRLDVP LLVEVGSGEN  600
WDQAH                                                              605

SEQ ID NO: 27          moltype = DNA  length = 606
FEATURE                Location/Qualifiers
misc_feature           1..606
                       note = Synthetic Polynucleotide
source                 1..606
                       mol_type = other DNA
                       organism = synthetic construct
SEQUENCE: 27
gccatcagat tgtgtttgtt agtcgctttt tttttttgga attttttttt tggaattttt  60
tttttgacgc tcagtaatgt gacgatagct gaaaactgta cgataaacgg tacgctgagg  120
gcggaaaaaa tcgtcgggga cattgtaaag gcggcgagcg cggcttttcc gcgccagcgt  180
gaaagcagtg tggactggcc gtcaggtacc cgtactgtca ccgtgaccga tgaccatcct  240
tttgatcgcc agatagtggt gcttccgctg acgtttcgcg gaagtaagcg tactgtcagc  300
ggcaggacaa cgtattcgat gtgttatctg aaagtactga tgaacggtgc ggtgatttat  360
gatggcgcgg cgaacgaggc ggtacaggtg ttctcccgta ttgttgacat gccagcgggt  420
cggggaaacg tgatcctgac gttcacgctt acgtccacac ggcattcggc agatattccg  480
ccgtatacgt ttgccagcga tgtgcaggtt atggtgatta agaaacaggc gctgggcatc  540
agcgtggtct gagtgtgaaa aaaaaggtac caaaaaaaac atcgtcgtga gtagtgaacc  600
gtaagc                                                             606

SEQ ID NO: 28          moltype = DNA  length = 91
FEATURE                Location/Qualifiers
misc_feature           1..91
                       note = Synthetic Polynucleotide
source                 1..91
                       mol_type = other DNA
                       organism = synthetic construct
SEQUENCE: 28
gccatcagat tgtgtttgtt agtcgctttt tttttttgga attttttttt tggaattttt  60
tttttgacgc tcagtaatgt gacgatagct g                                 91

SEQ ID NO: 29          moltype = DNA  length = 71
```

```
FEATURE                Location/Qualifiers
misc_feature           1..71
                       note = Synthetic Polynucleotide
source                 1..71
                       mol_type = other DNA
                       organism = synthetic construct
SEQUENCE: 29
gcttacggtt cactactcac gacgatgttt tttttggtac cttttttttc acactcagac  60
cacgctgatg c                                                       71

SEQ ID NO: 30          moltype = DNA  length = 97
FEATURE                Location/Qualifiers
misc_feature           1..97
                       note = Synthetic Polynucleotide
source                 1..97
                       mol_type = other DNA
                       organism = synthetic construct
SEQUENCE: 30
tttttttttt tttttttttt tttttttttt tttttttttt tttttttttt tttttttttt  60
tttttttttt ggttgtttct gttggtgctg atattgc                           97

SEQ ID NO: 31          moltype = DNA  length = 27
FEATURE                Location/Qualifiers
misc_feature           1..27
                       note = Synthetic Polynucleotide
source                 1..27
                       mol_type = other DNA
                       organism = synthetic construct
SEQUENCE: 31
gccatcagat tgtgtttgtt agtcgct                                      27

SEQ ID NO: 32          moltype = DNA  length = 59
FEATURE                Location/Qualifiers
misc_feature           1..59
                       note = Synthetic Polynucleotide
source                 1..59
                       mol_type = other DNA
                       organism = synthetic construct
SEQUENCE: 32
gcttatgttt tcataagctt ttgagctctt ttgcttacgg ttcactactc acgacgatg   59

SEQ ID NO: 33          moltype = DNA  length = 638
FEATURE                Location/Qualifiers
misc_feature           1..638
                       note = Synthetic Polynucleotide
source                 1..638
                       mol_type = other DNA
                       organism = synthetic construct
SEQUENCE: 33
gccatcagat tgtgtttgtt agtcgctttt tttttttgga attttttttt tggaattttt  60
tttttgacgc tcagtaatgt gacgatagct gaaaactgta cgataaacgg tacgctgagg  120
gcggaaaaaa tcgtcgggga cattgtaaag gcggcgagcg cggcttttcc gcgccagcgt  180
gaaagcagtg tggactggcc gtcaggtacc cgtactgtca ccgtgaccga tgaccatcct  240
tttgatcgcc agatagtggt gcttccgctg acgtttcgcg gaagtaagcg tactgtcagc  300
ggcaggacaa cgtattcgat gtgttatctg aaagtactga tgaacggtgc ggtgatttat  360
gatggcgcgg cgaacgaggc ggtacaggtg ttctcccgta ttgttgacat gccagcgggt  420
cggggaaacg tgatcctgac gttcacgctt acgtccacac ggcattcggc agatattccg  480
ccgtatacgt ttgccagcga tgtgcaggtt atggtgatta agaaacaggc gctgggcatc  540
agcgtggtct gagtgtgaaa aaaaaggtac caaaaaaaac atcgtcgtga gtagtgaacc  600
gtaagcaaaa gagctcaaaa gcttatgaaa acataagc                         638

SEQ ID NO: 34          moltype = DNA  length = 73
FEATURE                Location/Qualifiers
misc_feature           1..73
                       note = Synthetic Polynucleotide
source                 1..73
                       mol_type = other DNA
                       organism = synthetic construct
SEQUENCE: 34
tttttttttt tttttttttt tttttttttt tttttttttt ttttttggtt gtttctgttg  60
gtgctgatat tgc                                                     73

SEQ ID NO: 35          moltype = DNA  length = 3447
FEATURE                Location/Qualifiers
misc_feature           1..3447
                       note = Synthetic Polynucleotide
source                 1..3447
                       mol_type = other DNA
                       organism = synthetic construct
```

SEQUENCE: 35
gcgctaacaa cctcctgccg ttttgcccgt gcatatcggt cacgaacaaa tctgattact 60
aaacacagta gcctggattt gttctatcag taatcgacct tattcctaat taaatagagc 120
aaatcccctt attgggggta agacatgaag atgccagaaa aacatgacct gttggccgcc 180
attctcgcgg caaaggaaca aggcatcggg gcaatccttg cgtttgcaat ggcgtacctt 240
cgcggcagat ataatggcgg tgcgtttaca aaaacagtaa tcgacgcaac gatgtgcgcc 300
attatcgcct agttcattcg tgaccttctc gacttcgccg gactaagtag caatctcgct 360
tatataacga gcgtgtttat cggctacatc ggtactgact cgattggttc gcttatcaaa 420
cgcttcgctg ctaaaaaagc cggagtagaa gatggtagaa atcaataatc aacgtaaggc 480
gttcctcgat atgctggcgt ggtcggaggg aactgataac ggacgtcaga aaaccagaaa 540
tcatggttat gacgtcattg taggcggaga gctatttact gattactccg atcaccctcg 600
caaacttgtc acgctaaacc caaaactcaa atcaacaggc gccggacgct accagcttct 660
ttcccgttgg tgggatgcct accgcaagca gcttggcctg aaagacttct ctccgaaaag 720
tcaggacgct gtggcattgc agcagattaa ggagcgtggc gctttaccta tgattgatcg 780
tggtgatatc cgtcaggcaa tcgaccgttg cagcaatatc tgggcttcac tgccgggcgc 840
tggttatggt cagttcgagc ataaggctga cagcctgatt gcaaaattca aagaagcggg 900
cggaacggtc agagagattg atgtatgagc agagtcaccg cgattatctc cgctctggtt 960
atctgcatca tcgtctgcct gtcatgggct gttaatcatt accgtgataa cgccattacc 1020
tacaaagccc agcgcgacaa aaatgccaga gaactgaagc tggcgaacgc ggcaattact 1080
gacatgcaga tgcgtcagcg tgatgttgct gcgctcgatg caaaatacac gaaggagtta 1140
gctgatgcta aagctgaaaa tgatgctctg cgtgatgatg ttgccgctgg tcgtcgtcgg 1200
ttgcacatca aagcagtctg tcagtcagtg cgtgaagcca ccaccgcctc cggcgtggat 1260
aatgcagcct ccccccgact ggcagacacc gctgaacggg attatttcac cctcagagag 1320
aggctgatca ctatgcaaaa acaactggaa ggaacccaga agtatattaa tgagcagtgc 1380
agatagagtt gcccatatcg atgggcaact catgcaatta ttgtgagcaa tacacacgcg 1440
cttccagcgg agtataaatg cctaaagtaa taaaaccgag caatccattt acgaatgttt 1500
gctgggtttc tgttttaaca acattttctg cgccgccaca aattttggct gcatcgacag 1560
ttttcttctg cccaattcca gaaacgaaga aatgatgggt gatggtttcc tttggtgcta 1620
ctgctgccgg tttgttttga acagtaaacg tctgttgagc acatcctgta ataagcaggg 1680
ccagcgcagt agcgagtagc attttttttca tggtgttatt cccgatgctt tttgaagttc 1740
gcagaatcgt atgtgtagaa aattaaacaa accctaaaca atgagttgaa atttcatatt 1800
gttaatattt attaatgtat gtcaggtgcg atgaatcgtc attgtattcc cggattaact 1860
atgtccacag ccctgacggg gaacttctct gcgggagtgt ccgggaataa ttaaaacgat 1920
gcacacaggg tttagcgcgt acacgtattg cattatgcca acgccccggt gctgacacgg 1980
aagaaaccgg acgttatgat ttagcgtgga aagatttgtg tagtgttctg aatgctctca 2040
gtaaatagta atgaattatc aaaggtatag taatatcttt tatgttcatg gatatttgta 2100
acccatcgga aaactcctgc tttagcaaga ttttccctgt attgctgaaa tgtgatttct 2160
cttgatttca acctatcata ggacgtttct ataagatgcg tgtttcttga gaatttaaca 2220
tttacaacct ttttaagtcc ttttattaac acggtgttat cgttttctaa cacgatgtga 2280
atattatctg tggctagata gtaaatataa tgtgagacgt tgtgacgttt tagttcagaa 2340
taaaacaatt cacagtctaa atcttttcgc acttgatcga atatttcttt aaaaatggca 2400
acctgagcca ttggtaaaac cttccatgtg atacgagggc gcgtagtttg cattatcgtt 2460
tttatcgttt caatctggtc tgacctcctt gtgttttgtt gatgatttat gtcaaatatt 2520
aggaatgttt tcacttaata gtattggttg cgtaacaaag tgcggtcctg ctggcattct 2580
ggagggaaat acaaccgaca gatgtatgta aggccaacgt gctcaaatct tcatacagaa 2640
agatttgaag taatatttta accgctagat gaagagcaag cgcatggagc gacaaaatga 2700
ataaagaaca atctgctgat gatccctccg tggatctgat tcgtgtaaaa aatatgctta 2760
atagcaccat ttctatgagt taccctgatg ttgtaattgc atgtatagaa cataaggtgt 2820
ctctggaagc attcagagca attgaggcag cgttggtgaa gcacgataat aatatgaagg 2880
attattccct ggtggttgac tgatcaccat aactgctaat cattcaaact atttagtctg 2940
tgacagagcc aacacgcagt ctgtcactgt caggaaagtg gtaaaactgc aactcaatta 3000
ctgcaatgcc ctcgtaatta agtgaattta caatatcgtc ctgttcggag ggaagaacgc 3060
gggatgttca ttcttcatca cttttaattg atgtatatgc tctcttttct gacgttagtc 3120
tccgacggca ggcttcaatg acccaggctg agaaattccc ggaccctttt tgctcaagag 3180
cgatgttaat ttgttcaatc atttggttag gaaagcggat gttgcgggtt gttgttctgc 3240
gggttctgtt cttcgttgac atgaggttgc cccgtattca gtgtcgctga tttgtattgt 3300
ctgaagttgt ttttacgtta agttgatgca gatcaattaa tacgatacct gcgtcataat 3360
tgattatttg acgtggtttg atggcctcca cgcacgttgt gatatgtaga tgataatcat 3420
tatcacttta cgggtccttt ccggtga 3447

SEQ ID NO: 36 moltype = DNA length = 27
FEATURE Location/Qualifiers
misc_feature 1..27
note = Synthetic Polynucleotide
source 1..27
mol_type = other DNA
organism = synthetic construct
SEQUENCE: 36
ggttgtttct gttggtgctg atattgc 27

SEQ ID NO: 37 moltype = DNA length = 3560
FEATURE Location/Qualifiers
misc_feature 1..3560
note = Synthetic Polynucleotide
source 1..3560
mol_type = other DNA
organism = synthetic construct

```
SEQUENCE: 37
gccatcagat tgtgtttgtt agtcgctttt ttttttgga atttttttt tggaattttt  60
tttttgcgct aacaacctcc tgccgttttg cccgtgcata tcggtcacga acaaatctga  120
ttactaaaca cagtagcctg gatttgttct atcagtaatc gaccttattc ctaattaaat  180
agagcaaatc cccttattgg gggtaagaca tgaagatgcc agaaaaacat gacctgttgg  240
ccgccattct cgcggcaaag gaacaaggca tcggggcaat ccttgcgttt gcaatggcgt  300
accttcgcgg cagatataat ggcggtgcgt ttacaaaaac agtaatcgac gcaacgatgt  360
gcgccattat cgcctagttc attcgtgacc ttctcgactt cgccggacta agtagcaatc  420
tcgcttatat aacgagcgtg tttatcggct acatcggtac tgactcgatt ggttcgctta  480
tcaaacgctt cgctgctaaa aaagccggag tagaagatgg tagaaatcaa taatcaacgt  540
aaggcgttcc tcgatatgct ggcgtggtcg gagggaactg ataacggacg tcagaaaacc  600
agaaatcatg gttatgacgt cattgtaggc ggagagctat ttactgatta ctccgatcac  660
cctcgcaaac ttgtcacgct aaacccaaaa ctcaaatcaa caggcgccgg acgctaccag  720
cttctttccc gttggtggga tgcctaccgc aagcagcttg gcctgaaaga cttctctccg  780
aaaagtcagg acgctgtggc attgcagcag attaaggagc gtggcgcttt acctatgatt  840
gatcgtggtg atatccgtca ggcaatcgac cgttgcagca atatctgggc ttcactgccg  900
ggcgctggtt atggtcagtt cgagcataag gctgacagcc tgattgcaaa attcaaagaa  960
gcgggcggaa cggtcagaga gattgatgta tgagcagagt caccgcgatt atctccgctc  1020
tggttatctg catcatcgtc tgcctgtcat gggctgttaa tcattaccgt gataacgcca  1080
ttacctacaa agcccagcgc gacaaaaatg ccagagaact gaagctggcg aacgcggcaa  1140
ttactgacat gcagatgcgt cagcgtgatg ttgctgcgct cgatgcaaaa tacacgaagg  1200
agttagctga tgctaaagct gaaaatgatg ctctgcgtga tgatgttgcc gctggtcgtc  1260
gtcggttgca catcaaagca gtctgtcagt cagtgcgtga agccaccacc gcctccggcg  1320
tggataatgc agcctccccc cgactggcag acaccgctga acgggattat ttcaccctca  1380
gagagaggct gatcactatg caaaaacaac tggaaggaac ccagaagtat attaatgagc  1440
agtgcagata gagttgccca tatcgatggg caactcatgc aattattgtg agcaatacac  1500
acgcgcttcc agcggagtat aaatgcctaa agtaataaaa ccgagcaatc catttacgaa  1560
tgtttgctgg gtttctgttt taacaacatt ttctgcgccg ccacaaattt tggctgcatc  1620
gacagttttc ttctgcccaa ttccagaaac gaagaaatga tgggtgatgg tttcctttgg  1680
tgctactgct gccggtttgt tttgaacagt aaacgtctgt tgagcacatc ctgtaataag  1740
cagggccagc gcagtagcga gtagcatttt tttcatggtg ttattcccga tgctttttga  1800
agttcgcaga atcgtatgtg tagaaaatta aacaaaccct aaacaatgag ttgaaatttc  1860
atattgttaa tatttattaa tgtatgtcag gtgcgatgaa tcgtcattgt attcccggat  1920
taactatgtc cacagccctg acggggaact tctctgcggg agtgtccggg aataattaaa  1980
acgatgcaca cagggtttag cgcgtacacg tattgcatta tgccaacgcc ccggtgctga  2040
cacggaagaa accggacgtt atgatttagc gtggaaagat ttgtgtagtg ttctgaatgc  2100
tctcagtaaa tagtaatgaa ttatcaaagg tatagtaata tcttttatgt tcatggatat  2160
ttgtaaccca tcggaaaact cctgctttag caagattttc cctgtattgc tgaaatgtga  2220
tttctcttga tttcaaccta tcataggacg tttctataag atgcgtgttt cttgagaatt  2280
taacatttac aacctttta agtcctttta ttaacacggt gttatcgttt tctaacacga  2340
tgtgaatatt atctgtggct agatagtaaa tataatgtga gacgttgtga cgttttagtt  2400
cagaataaaa caattcacag tctaaatctt ttcgcacttg atcgaatatt tctttaaaaa  2460
tggcaacctg agccattggt aaaaccttcc atgtgatacg agggcgcgta gtttgcatta  2520
tcgtttttat cgtttcaatc tggtctgacc tccttgtgtt ttgttgatga tttatgtcaa  2580
atattaggaa tgttttcact taatagtatt ggttgcgtaa caaagtgcgg tcctgctggc  2640
attctggagg gaaatacaac cgacagatgt atgtaaggcc aacgtgctca aatcttcata  2700
cagaaagatt tgaagtaata ttttaaccgc tagatgaaga gcaagcgcat ggagcgacaa  2760
aatgaataaa gaacaatctg ctgatgatcc ctccgtggat ctgattcgtg taaaaaatat  2820
gcttaatagc accatttcta tgagttaccc tgatgttgta attgcatgta tagaacataa  2880
ggtgtctctg gaagcattca gagcaattga ggcagcgttg gtgaagcacg ataataatat  2940
gaaggattat tccctggtgg ttgactgatc accataactg ctaatcattc aaactattta  3000
gtctgtgaca gagccaacac gcagtctgtc actgtcagga aagtggtaaa actgcaactc  3060
aattactgca atgccctcgt aattaagtga atttacaata tcgtcctgtt cggagggaag  3120
aacgcgggat gttcattctt catcactttt aattgatgta tatgctctct tttctgacgt  3180
tagtctccga cggcaggctt caatgaccca ggctgagaaa ttcccggacc ctttttgctc  3240
aagagcgatg ttaatttgtt caatcatttg gttaggaaag cggatgttgc gggttgttgt  3300
tctgcgggtt ctgttcttcg ttgacatgag gttgccccgt attcagtgtc gctgatttgt  3360
attgtctgaa gttgttttta cgttaagttg atgcagatca attaatacga tacctgcgtc  3420
ataattgatt atttgacgtg gtttgatggc ctccacgcac gttgtgatat gtagatgata  3480
atcattatca ctttacgggt cctttccggt gaaaaaaaag gtaccaaaaa aaacatcgtc  3540
gtgagtagtg aaccgtaagc                                               3560

SEQ ID NO: 38           moltype = DNA  length = 1214
FEATURE                 Location/Qualifiers
misc_feature            1..1214
                        note = Synthetic Polynucleotide
source                  1..1214
                        mol_type = other DNA
                        organism = synthetic construct
SEQUENCE: 38
gccatcagat tgtgtttgtt agtcgctttt ttttttgga atttttttt tggaattttt  60
tttttgacgc tcagtaatgt gacgatagct gaaaactgta cgataaacgg tacgctgagg  120
gcggaaaaaa tcgtcgggga cattgtaaag gcggcgagcg cggcttttcc gcgccagcgt  180
gaaagcagtg tggactggcc gtcaggtacc cgtactgtca ccgtgaccga tgaccatcct  240
tttgatcgcc agatagtggt gcttccgctg acgtttcgcg gaagtaagcg tactgtcagc  300
ggcaggacaa cgtattcgat gtgttatctg aaagtactga tgaacggtgc ggtgatttat  360
gatggcgcgg cgaacgaggc ggtacaggtg ttctcccgta ttgttgacat gccagcgggt  420
cggggaaacg tgatcctgac gttcacgctt acgtccacac ggcattcggc agatattccg  480
ccgtatacgt ttgccagcga tgtgcaggtt atggtgatta agaaacaggc gctgggcatc  540
```

```
agcgtggtct gagtgtgcat cgtcgtgagt agtgaaccgt aagcaaaaga gctcaaaagc  600
ttatgaaaac ataagctttt gagctctttt gcttacggtt cactactcac gacgatgcac  660
actcagacca cgctgatgcc cagcgcctgt ttcttaatca ccataacctg cacatcgctg  720
gcaaacgtat acggcggaat atctgccgaa tgccgtgtgg acgtaagcgt gaacgtcagg  780
atcacgtttc cccgacccgc tggcatgtca acaatacggg agaacacctg taccgcctcg  840
ttcgccgcgc catcataaat caccgcaccg ttcatcagta ctttcagata acacatcgaa  900
tacgttgtcc tgccgctgac agtacgctta cttccgcgaa acgtcagcgg aagcaccact  960
atctggcgat caaaaggatg gtcatcggtc acggtgacag tacgggtacc tgacggccag  1020
tccacactgc tttcacgctg gcgcggaaaa gccgcgctcg ccgcctttac aatgtccccg  1080
acgatttttt ccgccctcag cgtaccgttt atcgtacagt tttcagctat cgtcacatta  1140
ctgagcgtca aaaaaaaaat tccaaaaaaa aaattccaaa aaaaaaaagc gactaacaaa  1200
cacaatctga tggc                                                    1214

SEQ ID NO: 39           moltype = DNA  length = 77
FEATURE                 Location/Qualifiers
misc_feature            1..77
                        note = Synthetic Polynucleotide
source                  1..77
                        mol_type = other DNA
                        organism = synthetic construct
SEQUENCE: 39
tttttttttt tttttttttt tttttttttt tttttttttt tttttttttt ggttgtttct  60
gttggtgctg atattgc                                                 77

SEQ ID NO: 40           moltype = DNA  length = 204
FEATURE                 Location/Qualifiers
misc_feature            1..204
                        note = Synthetic Polynucleotide
source                  1..204
                        mol_type = other DNA
                        organism = synthetic construct
SEQUENCE: 40
gacgctcagt aatgtgacga tatacgctga tgaccatcct tttgatcgcc agatagtggt  60
gcttccgctg acgtttcgcg gaagtaagcg tactgtcgtt ttcgacagta cgcttacttc  120
cgcgaaacgt cagcggaagc accactatct ggcgatcaaa aggatggtca tcagcgtata  180
tcgtcacatt actgagcgtc aaaa                                         204

SEQ ID NO: 41           moltype = DNA  length = 616
FEATURE                 Location/Qualifiers
misc_feature            1..616
                        note = Synthetic Polynucleotide
source                  1..616
                        mol_type = other DNA
                        organism = synthetic construct
SEQUENCE: 41
gccatcagat tgtgtttgtt agtcgctttt tttttttgga attttttttt tggaattttt  60
tttttgacgc tcagtaatgt gacgatagct gaaaactgta cgataaacgg tacgctgagg  120
gcggaaaaaa tcgtcgggga cattgtaaag gcggcgagcg cggcttttcc gcgccagcgt  180
gaaagcagtg tggactggcc gtcaggtacc cgtactgtca ccgtgaccga tgaccatcct  240
tttgatcgcc agatagtggt gcttccgctg acgtttcgcg gaagtaagcg tactgtcagc  300
ggcaggacaa cgtattcgat gtgttatctg aaagtactga tgaacggtgc ggtgatttat  360
gatggcgcgg cgaacgaggc ggtacaggtg ttctcccgta ttgttgacat gccagcgggt  420
cggggaaacg tgatcctgac gttcacgctt acgtccacac ggcattcggc agatattccg  480
ccgtatacgt ttgccagcga tgtgcaggtt atggtgatta agaaacaggc gctgggcatc  540
agcgtggtct gagtgtgcat cgtcgtgagt agtgaaccgt aagcaaaaga gctcaaaagc  600
ttatgaaaac ataagc                                                  616

SEQ ID NO: 42           moltype = DNA  length = 29
FEATURE                 Location/Qualifiers
misc_feature            1..29
                        note = Synthetic Polynucleotide
source                  1..29
                        mol_type = other DNA
                        organism = synthetic construct
SEQUENCE: 42
gcaatatcag caccaacaga aacaacctt                                    29

SEQ ID NO: 43           moltype = DNA  length = 50
FEATURE                 Location/Qualifiers
misc_feature            1..50
                        note = Synthetic Polynucleotide
source                  1..50
                        mol_type = other DNA
                        organism = synthetic construct
SEQUENCE: 43
gatcggaaga gcgcatcgtc gtgagtagtg aaccgtaagc gcatgcatca            50

SEQ ID NO: 44           moltype = DNA  length = 14
FEATURE                 Location/Qualifiers
```

-continued

```
misc_feature          1..14
                      note = Synthetic Polynucleotide
source                1..14
                      mol_type = other DNA
                      organism = synthetic construct
SEQUENCE: 44
cgctcttccg atct                                                   14

SEQ ID NO: 45         moltype = DNA  length = 12
FEATURE               Location/Qualifiers
misc_feature          1..12
                      note = Synthetic Polynucleotide
source                1..12
                      mol_type = other DNA
                      organism = synthetic construct
SEQUENCE: 45
tttttttttt tt                                                     12

SEQ ID NO: 46         moltype = DNA  length = 27
FEATURE               Location/Qualifiers
misc_feature          1..27
                      note = Synthetic Polynucleotide
source                1..27
                      mol_type = other DNA
                      organism = synthetic construct
SEQUENCE: 46
gcttacggtt cactactcac gacgatg                                     27

SEQ ID NO: 47         moltype = DNA  length = 3560
FEATURE               Location/Qualifiers
misc_feature          1..3560
                      note = Synthetic Polynucleotide
source                1..3560
                      mol_type = other DNA
                      organism = synthetic construct
SEQUENCE: 47
gcttacggtt cactactcac gacgatgttt tttttggtac cttttttttc accggaaagg  60
acccgtaaag tgataatgat tatcatctac atatcacaac gtgcgtggag gccatcaaac  120
cacgtcaaat aatcaattat gacgcaggta tcgtattaat tgatctgcat caacttaacg  180
taaaaacaac ttcagacaat acaaatcagc gacactgaat acggggcaac ctcatgtcaa  240
cgaagaacag aacccgcaga acaacaaccc gcaacatccg ctttcctaac caaatgattg  300
aacaaattaa catcgctctt gagcaaaaag ggtccgggaa tttctcagcc tgggtcattg  360
aagcctgccg tcggagacta acgtcagaaa agagagcata tacatcaatt aaaagtgatg  420
aagaatgaac atcccgcgtt cttccctccg aacaggacga tattgtaaat tcacttaatt  480
acgagggcat tgcagtaatt gagttgcagt tttaccactt tcctgacagt gacagactgc  540
gtgttggctc tgtcacagac taaatagttt gaatgattag cagttatggt gatcagtcaa  600
ccaccaggga ataatccttc atattattat cgtgcttcac caacgctgcc tcaattgctc  660
tgaatgcttc cagagacacc ttatgttcta tacatgcaat tacaacatca gggtaactca  720
tagaaatggt gctattaagc atatttttta cacgaatcag atccacggag ggatcatcag  780
cagattgttc tttattcatt ttgtcgctcc atgcgcttgc tcttcatcta gcggttaaaa  840
tattacttca aatctttctg tatgaagatt tgagcacgtt ggccttacat acatctgtcg  900
gttgtatttc cctccagaat gccagcagga ccgcactttg ttacgcaacc aatactatta  960
agtgaaaaca ttcctaatat ttgacataaa tcatcaacaa aacacaagga ggtcagacca  1020
gattgaaacg ataaaaacga taatgcaaac tacgcgccct cgtatcacat ggaaggtttt  1080
accaatggct caggttgcca tttttaaaga aatattcgat caagtgcgaa aagatttaga  1140
ctgtgaattg ttttattctg aactaaaacg tcacaacgtc tcacattata tttactatct  1200
agccacagat aatattcaca tcgtgttaga aaacgataac accgtgttaa taaaaggact  1260
taaaaaggtt gtaaatgtta aattctcaag aaacacgcat cttatagaaa cgtcctatga  1320
taggttgaaa tcaagagaaa tcacatttca gcaatacagg gaaaatcttg ctaaagcagg  1380
agttttccga tgggttacaa atatccatga acataaaaga tattactata cctttgataa  1440
ttcattacta tttactgaga gcattcagaa cactacacaa atctttccac gctaaatcat  1500
aacgtccggt ttcttccgtg tcagcaccgg ggcgttggca taatgcaata cgtgtacgcg  1560
ctaaaccctg tgtgcatcgt tttaattatt cccggacact cccgcagaga agttccccgt  1620
cagggctgtg gacatagtta atccgggaat acaatgacga ttcatcgcac ctgacataca  1680
ttaataaata ttaacaatat gaaatttcaa ctcattgttt agggtttgtt taattttcta  1740
cacatacgat tctgcgaact tcaaaaagca tcgggaataa caccatgaaa aaaatgctac  1800
tcgctactgc gctggccctg cttattacag gatgtgctca acagacgttt actgttcaaa  1860
acaaaccggc agcagtagca ccaaaggaaa ccatcaccca tcatttcttc gtttctggaa  1920
ttgggcagaa gaaaactgtc gatgcagcca aaatttgtgg cggcgcagaa aatgttgtta  1980
aaacagaaac ccagcaaaca ttcgtaaatg gattgctcgg ttttattact ttaggcattt  2040
atactccgct ggaagcgcgt gtgtattgct cacaataatt gcatgagttg cccatcgata  2100
tgggcaactc tatctgcact gctcattaat atacttctgg gttccttcca gttgtttttg  2160
catagtgatc agcctctctc tgagggtgaa ataatcccgt tcagcggtgt ctgccagtcg  2220
gggggaggct gcattatcca cgccggaggc ggtggtggct tcacgcactg actgacagac  2280
tgctttgatg tgcaaccgac gacgaccagc ggcaacatca tcacgcagag catcattttc  2340
agctttagca tcagctaact ccttcgtgta ttttgcatcg agcgcagcaa catcacgctg  2400
acgcatctgc atgtcagtaa ttgccgcgtt cgccagcttc agttctctgg catttttgtc  2460
gcgctgggct ttgtaggtaa tggcgttatc acggtaatga ttaacagccc atgacaggca  2520
gacgatgatg cagataacca gagcggagat aatcgcggtg actctgctca tacatcaatc  2580
```

-continued

```
tctctgaccg ttccgcccgc ttctttgaat tttgcaatca ggctgtcagc cttatgctcg  2640
aactgaccat aaccagcgcc cggcagtgaa gcccagatat tgctgcaacg gtcgattgcc  2700
tgacggatat caccacgatc aatcataggt aaagcgccac gctccttaat ctgctgcaat  2760
gccacagcgt cctgactttt cggagagaag tctttcaggc caagctgctt gcggtaggca  2820
tcccaccaac gggaaagaag ctggtagcgt ccggcgcctg ttgatttgag ttttgggttt  2880
agcgtgacaa gtttgcgagg gtgatcggag taatcagtaa atagctctcc gcctacaatg  2940
acgtcataac catgatttct ggttttctga cgtccgttat cagttccctc cgaccacgcc  3000
agcatatcga ggaacgcctt acgttgatta ttgatttcta ccatcttcta ctccggcttt  3060
tttagcagcg aagcgtttga taagcgaacc aatcgagtca gtaccgatgt agccgataaa  3120
cacgctcgtt atataagcga gattgctact tagtccggcg aagtcgagaa ggtcacgaat  3180
gaactaggcg ataatggcgc acatcgttgc gtcgattact gtttttgtaa acgcaccgcc  3240
attatatctg ccgcgaaggt acgccattgc aaacgcaagg attgccccga tgccttgttc  3300
ctttgccgcg agaatggcgg ccaacaggtc atgtttttct ggcatcttca tgtcttaccc  3360
ccaataaggg gatttgctct atttaattag gaataaggtc gattactgat agaacaaatc  3420
caggctactg tgtttagtaa tcagatttgt tcgtgaccga tatgcacggg caaaacggca  3480
ggaggttgtt agcgcaaaaa aaaaattcca aaaaaaaaat tccaaaaaaa aaaagcgact  3540
aacaaacaca atctgatggc                                              3560

SEQ ID NO: 48          moltype = DNA  length = 85
FEATURE                Location/Qualifiers
misc_feature           1..85
                       note = Synthetic Polynucleotide
source                 1..85
                       mol_type = other DNA
                       organism = synthetic construct
SEQUENCE: 48
gccatcagat tgtgtttgtt agtcgctttt tttttttgga atttttttt tggaattttt  60
tttttgcgct aacaacctcc tgccg                                        85

SEQ ID NO: 49          moltype = DNA  length = 85
FEATURE                Location/Qualifiers
misc_feature           1..85
                       note = Synthetic Polynucleotide
source                 1..85
                       mol_type = other DNA
                       organism = synthetic construct
SEQUENCE: 49
gccatcagat tgtgtttgtt agtcgctttt tttttttgga atttttttt tggaattttt  60
tttttgcgct aacaacctcc tgccg                                        85
```